United States Patent
Hagmann et al.

(10) Patent No.: US 9,834,563 B2
(45) Date of Patent: Dec. 5, 2017

(54) ANTIDIABETIC SUBSTITUTED HETEROARYL COMPOUNDS

(71) Applicant: Merck Sharp & Dohme Corp., Rahway, NJ (US)

(72) Inventors: William K. Hagmann, Westfield, NJ (US); Bing Li, Towaco, NJ (US); Jason W. Szewczyk, Collegeville, PA (US); Bowei Wang, Westfield, NJ (US); Dann Parker, Cranford, NJ (US); Timothy Blizzard, Princeton, NJ (US); Hubert Josien, Jersey City, NJ (US); Purakkattle Biju, Westwood, MA (US); Harry Chobanian, Aberdeen, NJ (US); Candido Gude, Staten Island, NY (US); Ravi P. Nargund, East Brunswick, NJ (US); Barbara Pio, West Orange, NJ (US); Qun Dang, Westfield, NJ (US); Linus S. Lin, Shanghai (CN); Bin Hu, Shanghai (CN); Mingxiang Cui, Shanghai (CN); Zhengxia Chen, Shanghai (CN); Meibi Dai, Shanghai (CN); Zaihong Zhang, Shanghai (CN); Ying Lv, Shanghai (CN); Lili Tian, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/039,607

(22) PCT Filed: Dec. 17, 2014

(86) PCT No.: PCT/US2014/070706
§ 371 (c)(1),
(2) Date: May 26, 2016

(87) PCT Pub. No.: WO2015/095256
PCT Pub. Date: Jun. 25, 2015

(65) Prior Publication Data
US 2017/0166578 A1    Jun. 15, 2017

(30) Foreign Application Priority Data
Dec. 19, 2013   (WO) ................ PCT/CN2013/090014

(51) Int. Cl.
*A61K 31/506* (2006.01)
*C07D 493/04* (2006.01)
(Continued)

(52) U.S. Cl.
CPC .......... *C07D 493/04* (2013.01); *A61K 31/437* (2013.01); *A61K 31/438* (2013.01);
(Continued)

(58) Field of Classification Search
CPC .. C07D 493/04; C07D 213/64; C07D 213/74; C07D 221/20; C07D 239/34;
(Continued)

(56) References Cited

U.S. PATENT DOCUMENTS 6,312,662 B1   11/2001   Erion et al.
6,489,476 B1   12/2002   Dang et al.
(Continued)

FOREIGN PATENT DOCUMENTS

DE   3316095 A1   5/1983
EP   0120403 A2   10/1984
(Continued)

OTHER PUBLICATIONS

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.
International Search Report for PCT/US2014/070706 dated Mar. 18, 2015.
Itoh, Y. et al., Free fatty acids regulate insulin secretion from pancreatic B cells through GPR40, Nature, 2003, 173-176, 422.
Kotarsky, K. et al., A human cell surface receptor activated by free fatty acids and thiazolidinedione drugs, Biochemical and Biophysical Research Communications, 2003, 406-410, 301.
Srivastava, A. et. al.; High-resolution structure of the human GPR40 receptor bound to allosteric agonist TAK-875, Nature, vol. 513; pp. 124-127, Sep. 4, 2014.
Takeuchi, M. et. al., FFA 1-selective agonistic activity based on docking simulation using FFA 1 and GPR 120 homology models, British Journal of Pharmacology, 158 (7), pp. 1570-1583.
(Continued)

*Primary Examiner* — Alexander R Pagano
(74) *Attorney, Agent, or Firm* — Baerbel R. Brown; Catherine D. Fitch

(57) ABSTRACT

The present invention relates to a compound represented by formula (I): and pharmaceutically acceptable salts thereof. The compounds of formula I are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

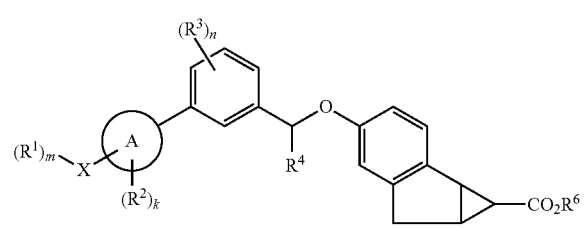

13 Claims, No Drawings

(51) Int. Cl.
A61K 45/06 (2006.01)
C07D 213/64 (2006.01)
A61K 31/44 (2006.01)
C07D 409/12 (2006.01)
A61K 31/4436 (2006.01)
C07D 401/04 (2006.01)
A61K 31/4545 (2006.01)
C07D 471/04 (2006.01)
A61K 31/437 (2006.01)
C07D 405/12 (2006.01)
A61K 31/4433 (2006.01)
C07D 401/12 (2006.01)
A61K 31/4439 (2006.01)
A61K 31/443 (2006.01)
C07D 239/34 (2006.01)
A61K 31/505 (2006.01)
C07D 451/06 (2006.01)
A61K 31/46 (2006.01)
C07D 221/20 (2006.01)
A61K 31/438 (2006.01)
C07D 213/74 (2006.01)
C07D 417/04 (2006.01)

(52) U.S. Cl.
CPC ............ *A61K 31/44* (2013.01); *A61K 31/443* (2013.01); *A61K 31/4433* (2013.01); *A61K 31/4436* (2013.01); *A61K 31/4439* (2013.01); *A61K 31/4545* (2013.01); *A61K 31/46* (2013.01); *A61K 31/505* (2013.01); *A61K 31/506* (2013.01); *A61K 45/06* (2013.01); *C07D 213/64* (2013.01); *C07D 213/74* (2013.01); *C07D 221/20* (2013.01); *C07D 239/34* (2013.01); *C07D 401/04* (2013.01); *C07D 401/12* (2013.01); *C07D 405/12* (2013.01); *C07D 409/12* (2013.01); *C07D 417/04* (2013.01); *C07D 451/06* (2013.01); *C07D 471/04* (2013.01)

(58) Field of Classification Search
CPC .. C07D 401/04; C07D 401/12; C07D 405/12; C07D 409/12; C07D 417/04; C07D 451/06; C07D 471/04; A61K 31/437; A61K 31/438; A61K 31/44; A61K 31/443; A61K 31/4433; A61K 31/4436; A61K 31/4439; A61K 31/4545; A61K 31/46; A61K 31/505; A61K 31/506; A61K 45/06
See application file for complete search history.

(56) References Cited

U.S. PATENT DOCUMENTS

| 8,399,507 | B2* | 3/2013 | Liang | C07C 62/34 |
| | | | | 514/411 |
| 9,273,046 | B2* | 3/2016 | Zhou | C07D 471/04 |
| 9,527,875 | B2* | 12/2016 | Hagmann | C07D 401/14 |
| 2005/0148643 | A1 | 7/2005 | Rui et al. | |
| 2007/0213364 | A1 | 9/2007 | Yasuma et al. | |
| 2007/0265332 | A1 | 11/2007 | Ge et al. | |
| 2010/0216694 | A1* | 8/2010 | Liang | C07C 62/34 |
| | | | | 514/1.1 |
| 2011/0190330 | A1 | 8/2011 | Brown et al. | |
| 2012/0004187 | A1 | 1/2012 | Keil et al. | |
| 2013/0053345 | A1 | 2/2013 | Ye et al. | |
| 2014/0045746 | A1 | 2/2014 | Hagmann et al. | |

FOREIGN PATENT DOCUMENTS

| EP | 0126030 A2 | 11/1984 |
| EP | 0128862 A2 | 12/1984 |
| EP | 0129506 B1 | 12/1984 |
| JP | 6298731 | 10/1994 |
| WO | WO9307124 A1 | 4/1993 |
| WO | WO9529897 A1 | 11/1995 |
| WO | WO9839342 A1 | 9/1998 |
| WO | WO9839343 A1 | 9/1998 |
| WO | WO0003997 A1 | 1/2000 |
| WO | WO0014095 A1 | 3/2000 |
| WO | WO0153272 A1 | 7/2001 |
| WO | WO0153291 A1 | 7/2001 |
| WO | WO0240019 A1 | 5/2002 |
| WO | WO02092575 A1 | 11/2002 |
| WO | WO03018061 A1 | 3/2003 |
| WO | WO2004022551 A1 | 3/2004 |
| WO | WO2004041266 A1 | 5/2004 |
| WO | WO2005002520 A2 | 1/2005 |
| WO | WO2005018672 A1 | 3/2005 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006094209 A2 | 9/2006 |
| WO | WO2006127503 A2 | 11/2006 |
| WO | WO2007013689 A1 | 2/2007 |
| WO | WO2007033002 A1 | 3/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO2009111056 A1 | 9/2009 |
| WO | WO2010036613 A1 | 4/2010 |
| WO | WO2010045258 A2 | 4/2010 |
| WO | WO2010047982 A1 | 4/2010 |
| WO | WO2010051176 A1 | 5/2010 |
| WO | WO2010051206 A1 | 5/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2015089809 A1 | 6/2015 |
| WO | WO2015095256 A1 | 6/2015 |

OTHER PUBLICATIONS

Written Opinion of the International Searching Authority for PCT/CN2013/090014 dated May 13, 2015.

* cited by examiner

ANTIDIABETIC SUBSTITUTED HETEROARYL COMPOUNDS

CROSS-REFERENCE TO RELATED APPLICATIONS

This application is a U.S. National Phase application under 35 U.S.C. §371 of PCT Application PCT/US14/070706, filed Dec. 17, 2014, which claims priority from and the benefit of PCT Application PCT/CN13/090014; filed Dec. 19, 2013.

FIELD OF THE INVENTION

The instant invention relates to novel substituted tetrahydrocyclopropa[a]indene-1-carboxylic acids and pharmaceutically acceptable carboxylic acid derivatives, including pharmaceutically acceptable salts thereof, which are agonists of G-protein-coupled receptor 40 (GPR40) and are useful as therapeutic compounds, particularly in the treatment of Type 2 diabetes mellitus, and of conditions that are often associated with this disease, including obesity and lipid disorders.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion.

There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

Benzimidazole compounds are disclosed in WO 2010/051206; WO 2010/051176; WO 2010/047982; WO 2010/036613; WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. No. 6,312,662; U.S. Pat. No. 6,489,476; US 2005/0148643; DE 3 316 095; JP 6 298 731; EP 0 126 030; EP 0 128 862; EP 0 129 506; and EP 0 120 403.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030618, WO 2008/054674, WO 2008/054675, WO 2008/066097, WO 2008/130514, WO 2009/048527, WO 2009/111056, WO 2010/045258, WO 2010/085522, WO 2010/085525, WO 2010/085528, WO 2010/091176, WO 2010/143733 and WO 2012/0004187.

SUMMARY OF THE INVENTION

The present invention relates to novel substituted compounds of structural formula I:

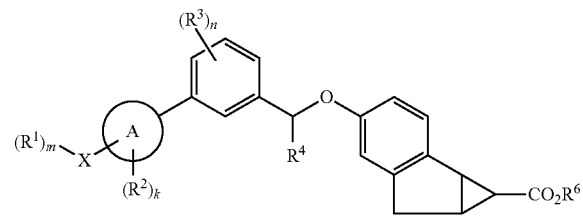

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

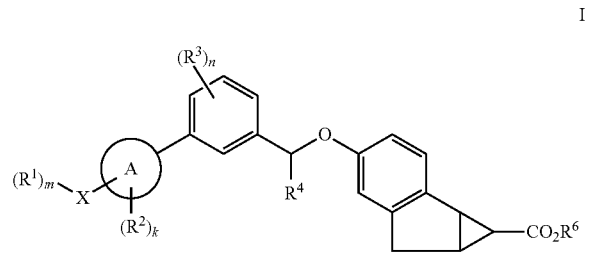

or a pharmaceutically acceptable salt thereof; wherein
ring A is a monocyclic heteroaryl containing 1 to 2 N heteroatoms or a bicyclic heteroaryl containing 1 to 4 heteroatoms independently selected from the group consisting of N, O, and S;
X is
  (1) bond,
  (2) —O—,
  (3) —N(H)—,
  (4) —($C_{1-6}$)alkyl-O—, wherein the alkyl or oxygen attaches to ring A,
  (5) —O—($C_{1-6}$)alkyl-O—, or
  (6) —($C_{1-6}$)alkyl-N(H)—, wherein the alkyl or nitrogen attaches to ring A;
$R^1$ is
  (1) ($C_{3-7}$)cycloalkyl,
  (2) heterocycloalkyl containing 1 to 2 heteroatoms independently selected from the group consisting of N, S, and O,
  (3) heteroaryl containing 1 to 3 heteroatoms independently selected from the group consisting of N, O, and S,
  (4) —S(O)$_2$($C_{1-3}$)alkyl, or
  (5) —(CH$_2$)$_q$-aryl,
wherein each heterocycloalkyl, heteroaryl, aryl, or cycloalkyl groups are unsubstituted or substituted with 1 to 2 substitutents each independently $R^5$;
$R^2$ is
  (1) ($C_{1-6}$)alkyl,
  (2) halo($C_{1-6}$)alkyl,
  (3) hydroxy($C_{1-6}$)alkyl, or
  (4) halo;
$R^3$ is
  (1) ($C_{1-6}$)alkyl, or
  (2) halo;
$R^4$ is
  (1) hydrogen, or
  (2) ($C_{1-3}$)alkyl;
$R^5$ is
  (1) oxo,
  (2) hydroxy,
  (3) ($C_{1-6}$)alkyl, (4) halo($C_{1-6}$)alkyl,
(5) hydroxy($C_{1-6}$)alkyl,
(6) cyano,
(7) phenyl,
(8) —S(O)$_2$($C_{1-3}$)alkyl,
(9) —($C_{1-3}$)alkyl-S(O)$_2$($C_{1-3}$)alkyl, or
(10) —($C_{1-3}$)alkyl-N(H)—S(O)$_2$($C_{1-3}$)alkyl;

$R^6$ is
(1) hydrogen,
(2) ($C_{1-6}$)alkyl, or
(3) ($C_{3-7}$)cycloalkyl;

n is 0, 1, 2, or 3;
m is 0 or 1;
k is 0, 1, 2 or 3; and
q is 0, 1, 2 or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, ring A is a monocyclic heteroaryl containing 1 to 2 N heteroatoms. In one class of this embodiment, $R^1$ is ($C_{3-7}$)cycloalkyl, unsubstituted or substituted with 1 to 2 substituents each independently $R^5$. In one class of this embodiment, $R^1$ is a heterocycloalkyl containing 1 to 2 heteroatoms independently selected from the group consisting of N, S, and O, wherein the heterocycloalkyl is unsubstituted or substituted with 1 to 2 substituents each independently $R^5$. In one class of this embodiment, $R^1$ is a heteroaryl containing 1 to 3 heteroatoms independently selected from the group consisting of N, O, and S, wherein the heteroaryl ring is unsubstituted or substituted by 1 to 2 substituents each independently $R^5$. In one class of this embodiment, $R^1$ is —S(O)$_2$($C_{1-3}$)alkyl. In one class of this embodiment, $R^1$ is —(CH$_2$)q-aryl, unsubstituted or substituted by 1 to 2 substituents each independently $R^5$. In one subclass of this subclass, $R^1$ is a fused aryl, unsubstituted or substituted by 1 to 2 substituents each independently $R^5$. In one sub-subclass of this subclass, $R^1$ is spiro[indene-1,4'-piperidinyl], unsubstituted or substituted by 1 to 2 substituents each independently $R^5$.

In one class of this embodiment, ring A is pyridinyl or pyrimidinyl. In one subclass of this class, $R^1$ is ($C_{3-7}$)cycloalkyl, unsubstituted or substituted with 1 to 2 substituents each independently $R^5$. In one subclass of this class, $R^1$ is a heterocycloalkyl containing 1 to 2 heteroatoms independently selected from the group consisting of N, S, and O, wherein the heterocycloalkyl is unsubstituted or substituted with 1 to 2 substituents each independently $R^5$. In one subclass of this class, $R^1$ is a heteroaryl containing 1 to 3 heteroatoms independently selected from the group consisting of N, O, and S, wherein the heteroaryl ring is unsubstituted or substituted by 1 to 2 substituents each independently $R^5$. In one subclass of this class, $R^1$ is —S(O)$_2$($C_{1-3}$)alkyl. In one subclass of this class, $R^1$ is —(CH$_2$)q-aryl, unsubstituted or substituted by 1 to 2 substituents each independently $R^5$. In one sub-subclass of this subclass, $R^1$ is a fused aryl, unsubstituted or substituted by 1 to 2 substituents each independently $R^5$. In one sub-sub-subclass of this sub-subclass, $R^1$ is spiro[indene-1,4'-piperidinyl], unsubstituted or substituted by 1 to 2 substituents each independently $R^5$.

In another class of this embodiment, ring A is

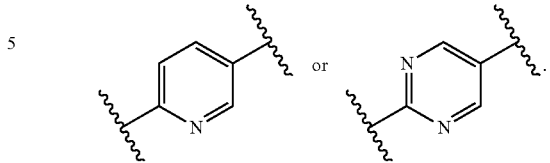

In one subclass of this class, $R^1$ is ($C_{3-7}$)cycloalkyl, unsubstituted or substituted with 1 to 2 substituents each independently $R^5$. In one subclass of this class, $R^1$ is a heterocycloalkyl containing 1 to 2 heteroatoms independently selected from the group consisting of N, S, and O, wherein the heterocycloalkyl is unsubstituted or substituted with 1 to 2 substituents each independently $R^5$. In one subclass of this class, $R^1$ is a heteroaryl containing 1 to 3 heteroatoms independently selected from the group consisting of N, O, and S, wherein the heteroaryl ring is unsubstituted or substituted by 1 to 2 substituents each independently $R^5$. In one subclass of this class, $R^1$ is —S(O)$_2$($C_{1-3}$)alkyl. In one subclass of this class, $R^1$ is —(CH$_2$)q-aryl, unsubstituted or substituted by 1 to 2 substituents each independently $R^5$. In one sub-subclass of this subclass, $R^1$ is a fused aryl, unsubstituted or substituted by 1 to 2 substituents each independently $R^5$. In one sub-sub-subclass of this sub-subclass, $R^1$ is spiro[indene-1,4'-piperidinyl], unsubstituted or substituted by 1 to 2 substituents each independently $R^5$.

In another class of this embodiment, ring A is

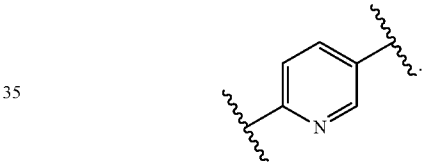

In one subclass of this class, $R^1$ is ($C_{3-7}$)cycloalkyl, unsubstituted or substituted with 1 to 2 substituents each independently $R^5$. In one subclass of this class, $R^1$ is a heterocycloalkyl containing 1 to 2 heteroatoms independently selected from the group consisting of N, S, and O, wherein the heterocycloalkyl is unsubstituted or substituted with 1 to 2 substituents each independently $R^5$. In one subclass of this class, $R^1$ is a heteroaryl containing 1 to 3 heteroatoms independently selected from the group consisting of N, O, and S, wherein the heteroaryl ring is unsubstituted or substituted by 1 to 2 substituents each independently $R^5$. In one subclass of this class, $R^1$ is —S(O)$_2$($C_{1-3}$)alkyl. In one subclass of this class, $R^1$ is —(CH$_2$)q-aryl, unsubstituted or substituted by 1 to 2 substituents each independently $R^5$. In one sub-subclass of this subclass, $R^1$ is a fused aryl, unsubstituted or substituted by 1 to 2 substituents each independently $R^5$. In one sub-sub-subclass of this sub-subclass, $R^1$ is spiro[indene-1,4'-piperidinyl], unsubstituted or substituted by 1 to 2 substituents each independently $R^5$.

In another class of this embodiment, ring A is

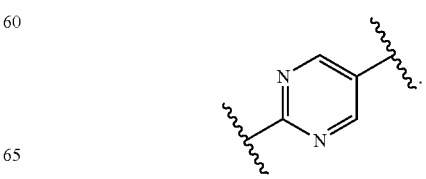

In one subclass of this class, R¹ is (C₃₋₇)cycloalkyl, unsubstituted or substituted with 1 to 2 substituents each independently R⁵. In one subclass of this class, R¹ is a heterocycloalkyl containing 1 to 2 heteroatoms independently selected from the group consisting of N, S, and O, wherein the heterocycloalkyl is unsubstituted or substituted with 1 to 2 substituents each independently R⁵. In one subclass of this class, R¹ is a heteroaryl containing 1 to 3 heteroatoms independently selected from the group consisting of N, O, and S, wherein the heteroaryl ring is unsubstituted or substituted by 1 to 2 substituents each independently R⁵. In one subclass of this class, R¹ is —S(O)₂(C₁₋₃)alkyl. In one subclass of this class, R¹ is —(CH₂)q-aryl, unsubstituted or substituted by 1 to 2 substituents each independently R⁵. In one sub-subclass of this subclass, R¹ is a fused aryl, unsubstituted or substituted by 1 to 2 substituents each independently R⁵. In one sub-sub-subclass of this sub-subclass, R¹ is spiro[indene-1,4'-piperidinyl], unsubstituted or substituted by 1 to 2 substituents each independently R⁵.

In one embodiment of the present invention, ring A is a bicyclic heteroaryl containing 1 to 4 heteroatoms independently selected from the group consisting of N, O, and S. In one class of this embodiment, R¹ is (C₃₋₇)cycloalkyl, unsubstituted or substituted with 1 to 2 substituents each independently R⁵. In one class of this embodiment, R¹ is a heterocycloalkyl containing 1 to 2 heteroatoms independently selected from the group consisting of N, S, and O, wherein the heterocycloalkyl is unsubstituted or substituted with 1 to 2 substituents each independently R⁵. In one class of this embodiment, R¹ is a heteroaryl containing 1 to 3 heteroatoms independently selected from the group consisting of N, O, and S, wherein the heteroaryl ring is unsubstituted or substituted by 1 to 2 substituents each independently R⁵. In one class of this embodiment, R¹ is —S(O)₂(C₁₋₃)alkyl. In one subclass of this class, R¹ is —(CH₂)q-aryl, unsubstituted or substituted by 1 to 2 substituents each independently R⁵. In one sub-subclass of this subclass, R¹ is a fused aryl, unsubstituted or substituted by 1 to 2 substituents each independently R⁵. In one sub-sub-subclass of this sub-subclass, R¹ is spiro[indene-1,4'-piperidinyl], unsubstituted or substituted by 1 to 2 substituents each independently R⁵.

In one class of this embodiment, ring A is a bicyclic heteroaryl containing 1 to 3 heteroatoms independently selected from the group consisting of N, O, and S. In one subclass of this class, R¹ is (C₃₋₇)cycloalkyl, unsubstituted or substituted with 1 to 2 R⁵. In one subclass of this class, R¹ is a heterocycloalkyl containing 1 to 2 heteroatoms independently selected from the group consisting of N, S, and O, wherein the heterocycloalkyl is unsubstituted or substituted with 1 to 2 substituents each independently R⁵. In one subclass of this class, R¹ is a heteroaryl containing 1 to 3 heteroatoms independently selected from the group consisting of N, O, and S, wherein the heteroaryl ring is unsubstituted or substituted by 1 to 2 substituents each independently R⁵. In one subclass of this class, R¹ is —S(O)₂(C₁₋₃)alkyl. In one subclass of this class, R¹ is —(CH₂)q-aryl, unsubstituted or substituted by 1 to 2 substituents each independently R⁵. In one sub-subclass of this subclass, R¹ is a fused aryl, unsubstituted or substituted by 1 to 2 substituents each independently R⁵. In one sub-sub-subclass of this sub-subclass, R¹ is spiro[indene-1,4'-piperidinyl], unsubstituted or substituted by 1 to 2 substituents each independently R⁵.

In one class of this embodiment, ring A is 1H-pyrazolo[4,3-b]pyridinyl, thiazolo[4,5-b]pyridinyl, or 1H-pyrrolo[2,3-b]pyridinyl. In one subclass of this class, R¹ is (C₃₋₇)cycloalkyl, unsubstituted or substituted with 1 to 2 substituents each independently R⁵. In one subclass of this class, R¹ is a heterocycloalkyl containing 1 to 2 heteroatoms independently selected from the group consisting of N, S, and O, wherein the heterocycloalkyl is unsubstituted or substituted with 1 to 2 substituents each independently R⁵. In one subclass of this class, R¹ is a heteroaryl containing 1 to 3 heteroatoms independently selected from the group consisting of N, O, and S, wherein the heteroaryl ring is unsubstituted or substituted by 1 to 2 substituents each independently R⁵. In one subclass of this class, R¹ is —S(O)₂(C₁₋₃)alkyl. In one subclass of this class, R¹ is —(CH₂)q-aryl, unsubstituted or substituted by 1 to 2 substituents each independently R⁵. In one sub-subclass of this subclass, R¹ is a fused aryl, unsubstituted or substituted by 1 to 2 substituents each independently R⁵. In one sub-sub-subclass of this sub-subclass, R¹ is spiro[indene-1,4'-piperidinyl], unsubstituted or substituted by 1 to 2 substituents each independently R⁵.

In one class of this embodiment, ring A is

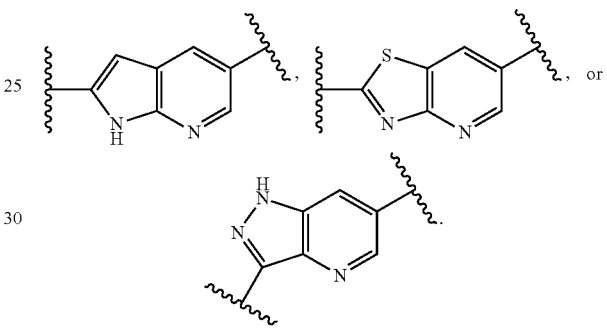

In one subclass of this class, R¹ is (C₃₋₇)cycloalkyl, unsubstituted or substituted with 1 to 2 R⁵. In one subclass of this class, R¹ is a heterocycloalkyl containing 1 to 2 heteroatoms independently selected from the group consisting of N, S, and O, wherein the heterocycloalkyl is unsubstituted or substituted with 1 to 2 substituents each independently R⁵. In one subclass of this class, R¹ is a heteroaryl containing 1 to 3 heteroatoms independently selected from the group consisting of N, O, and S, wherein the heteroaryl ring is unsubstituted or substituted by 1 to 2 substituents each independently R⁵. In one subclass of this class, R¹ is —S(O)₂(C₁₋₃)alkyl. In one subclass of this class, R¹ is —(CH₂)q-aryl, unsubstituted or substituted by 1 to 2 substituents each independently R⁵. In one sub-subclass of this subclass, R¹ is a fused aryl, unsubstituted or substituted by 1 to 2 substituents each independently R⁵. In one sub-sub-subclass of this sub-subclass, R¹ is spiro[indene-1,4'-piperidinyl], unsubstituted or substituted by 1 to 2 substituents each independently R⁵.

In one class of this embodiment, ring A is

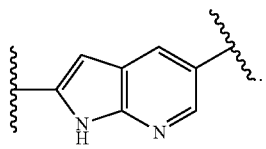 [SMILES: *c1cnc2[nH]c(*)cc2c1]

In one subclass of this class, R¹ is (C₃₋₇)cycloalkyl, unsubstituted or substituted with 1 to 2 substituents each independently R⁵. In one subclass of this class, R¹ is a heterocycloalkyl containing 1 to 2 heteroatoms independently selected from the group consisting of N, S, and O, wherein the heterocycloalkyl is unsubstituted or substituted with 1 to 2 substituents each independently $R^5$. In one subclass of this class, $R^1$ is a heteroaryl containing 1 to 3 heteroatoms independently selected from the group consisting of N, O, and S, wherein the heteroaryl ring is unsubstituted or substituted by 1 to 2 substituents each independently $R^5$. In one subclass of this class, $R^1$ is —S(O)$_2$(C$_{1-3}$)alkyl. In one subclass of this class, $R^1$ is —(CH$_2$)q-aryl, unsubstituted or substituted by 1 to 2 substituents each independently $R^5$. In one sub-subclass of this subclass, $R^1$ is a fused aryl, unsubstituted or substituted by 1 to 2 substituents each independently $R^5$. In one sub-sub-subclass of this sub-subclass, $R^1$ is spiro[indene-1,4'-piperidinyl], unsubstituted or substituted by 1 to 2 substituents each independently $R^5$.

In one class of this embodiment, ring A is

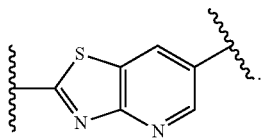 [SMILES: *c1cnc2nc(*)sc2c1]

In one subclass of this class, $R^1$ is (C$_{3-7}$)cycloalkyl, unsubstituted or substituted with 1 to 2 substituents each independently $R^5$. In one subclass of this class, $R^1$ is a heterocycloalkyl containing 1 to 2 heteroatoms independently selected from the group consisting of N, S, and O, wherein the heterocycloalkyl is unsubstituted or substituted with 1 to 2 substituents each independently $R^5$. In one subclass of this class, $R^1$ is a heteroaryl containing 1 to 3 heteroatoms independently selected from the group consisting of N, O, and S, wherein the heteroaryl ring is unsubstituted or substituted by 1 to 2 substituents each independently $R^5$. In one subclass of this class, $R^1$ is —S(O)$_2$(C$_{1-3}$)alkyl. In one subclass of this class, $R^1$ is —(CH$_2$)q-aryl, unsubstituted or substituted by 1 to 2 substituents each independently $R^5$. In one sub-subclass of this subclass, $R^1$ is a fused aryl, unsubstituted or substituted by 1 to 2 substituents each independently $R^5$. In one sub-sub-subclass of this sub-subclass, $R^1$ is spiro[indene-1,4'-piperidinyl], unsubstituted or substituted by 1 to 2 substituents each independently $R^5$.

In another class of this embodiment, ring A is

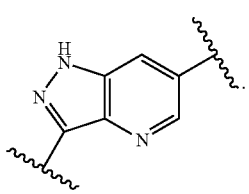 [SMILES: *c1cnc2c(*)n[nH]c2c1]

In one subclass of this class, $R^1$ is (C$_{3-7}$)cycloalkyl, unsubstituted or substituted with 1 to 2 substituents each independently $R^5$. In one subclass of this class, $R^1$ is a heterocycloalkyl containing 1 to 2 heteroatoms independently selected from the group consisting of N, S, and O, wherein the heterocycloalkyl is unsubstituted or substituted with 1 to 2 substituents each independently $R^5$. In one subclass of this class, $R^1$ is a heteroaryl containing 1 to 3 heteroatoms independently selected from the group consisting of N, O, and S, wherein the heteroaryl ring is unsubstituted or substituted by 1 to 2 $R^5$. In one subclass of this class, $R^1$ is —S(O)$_2$(C$_{1-3}$)alkyl. In one subclass of this class, $R^1$ is —(CH$_2$)q-aryl, unsubstituted or substituted by 1 to 2 substituents each independently $R^5$. In one sub-subclass of this subclass, $R^1$ is a fused aryl, unsubstituted or substituted by 1 to 2 substituents each independently $R^5$. In one sub-sub-subclass of this sub-subclass, $R^1$ is spiro[indene-1,4'-piperidinyl], unsubstituted or substituted by 1 to 2 substituents each independently $R^5$.

In one embodiment, $R^1$ is (C$_{3-7}$)cycloalkyl, unsubstituted or substituted with 1 to 2 substituents each independently $R^5$. In one class of this embodiment, $R^1$ is cyclohexyl, cyclobutyl, or cyclopropyl, wherein each ring is unsubstituted or substituted with 1 to 2 substituents each independently $R^5$. In one subclass of this class, $R^1$ is cyclohexyl. In one subclass of this class, $R^1$ is cyclobutyl. In one subclass of this class, $R^1$ is cyclopropyl.

In one embodiment, $R^1$ is a heterocycloalkyl containing 1 to 2 heteroatoms independently selected from the group consisting of N, S, and O, wherein the heterocycloalkyl is unsubstituted or substituted with 1 to 2 substituents each independently $R^5$. In one class of this embodiment, $R^1$ is piperidinyl, piperazinyl, pyrrolidinyl, azetidinyl, tetrahydropyranyl, tetrahydrothiopyran, or hexahydrofuro[3,2-b]furanyl, wherein each ring system is unsubstituted or substituted by 1 to 2 substituents each independently $R^5$. In one subclass of this class, $R^1$ is piperidinyl unsubstituted or substituted by 1 to 2 substituents each independently $R^5$. In one subclass of this class, $R^1$ is piperazinyl unsubstituted or substituted by 1 to 2 substituents each independently $R^5$. In one subclass of this class, $R^1$ is pyrrolidinyl unsubstituted or substituted by 1 to 2 substituents each independently $R^5$. In one subclass of this class, $R^1$ is azetidinyl unsubstituted or substituted by 1 to 2 substituents each independently $R^5$. In one subclass of this class, $R^1$ is tetrahydropyranyl unsubstituted or substituted by 1 to 2 substituents each independently $R^5$. In one subclass of this class, $R^1$ is tetrahydrothiopyran unsubstituted or substituted by 1 to 2 substituents each independently $R^5$. In one subclass of this class, $R^1$ is tetrahydrothiopyran unsubstituted or substituted by 1 to 2 substituents each independently $R^5$. In one subclass of this class, $R^1$ is hexahydrofuro[3,2-b]furanyl unsubstituted or substituted by 1 to 2 substituents each independently $R^5$.

In one embodiment, $R^1$ is a heteroaryl containing 1 to 3 heteroatoms independently selected from the group consisting of N, O, and S, wherein the heteroaryl ring is unsubstituted or substituted by 1 to 2 substituents each independently $R^5$. In one class of this embodiment, $R^1$ is triazolyl, pyrazinyl, pyrimidinyl or pyridinyl. In one class of this embodiment, $R^1$ is triazolyl or pyridinyl.

In one embodiment, $R^1$ is —S(O)$_2$(C$_{1-3}$)alkyl. In one embodiment, $R^1$ is —O—(C$_{1-3}$)alkyl-aryl, wherein the aryl ring is unsubstituted or substituted by 1 to 2 substituents each independently $R^5$.

In one embodiment, $R^1$ is —(CH$_2$)q-aryl, unsubstituted or substituted by 1 to 2 substituents each independently $R^5$. In one class of this embodiment, $R^1$ is —CH$_2$-phenyl, unsubstituted or substituted by 1 to 2 substituents each independently $R^5$. In one class of this embodiment, $R^1$ is a fused aryl, wherein the aryl ring is unsubstituted or substituted by 1 to 2 substituents each independently $R^5$. In one subclass of this class, $R^1$ is spiro[inden-1,4'-piperidinyl], which is unsubstituted or substituted with 1 to 2 substituents each independently $R^5$.

In one embodiment, X is a bond, —O—, —(C$_{1-6}$)alkyl-O—, or —(C$_{1-6}$)alkyl-N(H)—.

In one embodiment, X is a bond, —O—, —N(H)—, —(CH$_2$)$_3$—NH—, —(CH$_2$)$_2$—NH—, —CH$_2$—N(H)—, —(CH$_2$)$_4$—O—, —(CH$_2$)$_3$—O—, —(CH$_2$)$_2$—O—, or —CH$_2$—O—. In a class of this embodiment, X is a bond, —O—, —(CH$_2$)$_3$—NH—, —CH$_2$—N(H)—, —(CH$_2$)$_4$—O—, —(CH$_2$)$_3$—O—, —(CH$_2$)$_2$—O—, or —CH$_2$—O—.

In one embodiment, X is a bond. In one class of this embodiment, R$^1$ is (C$_{3-7}$)cycloalkyl, unsubstituted or substituted with 1 to 2 substituents each independently R$^5$. In one class of this embodiment, R$^1$ is a heterocycloalkyl containing 1 to 2 heteroatoms independently selected from the group consisting of N, S, and O, wherein the heterocycloalkyl is unsubstituted or substituted with 1 to 2 substituents each independently R$^5$. In one class of this embodiment, R$^1$ is a heteroaryl containing 1 to 3 heteroatoms independently selected from the group consisting of N, O, and S, wherein the heteroaryl ring is unsubstituted or substituted by 1 to 2 substituents each independently R$^5$. In one class of this embodiment, R$^1$ is —S(O)$_2$(C$_{1-3}$)alkyl. In one class of this embodiment, R$^1$ is —O—(C$_{1-3}$)alkyl-aryl, wherein the aryl ring is unsubstituted or substituted by 1 to 2 substituents each independently R$^5$. In one class of this embodiment, R$^1$ is —(CH$_2$)q-aryl, unsubstituted or substituted by 1 to 2 substituents each independently R$^5$. In one subclass of this class, R$^1$ is a fused aryl, unsubstituted or substituted by 1 to 2 substituents each independently R$^5$. In one sub-subclass of this subclass, R$^1$ is spiro[indene-1,4'-piperidinyl], unsubstituted or substituted by 1 to 2 substituents each independently R$^5$.

In one embodiment, X is —O—. In one class of this embodiment, R$^1$ is (C$_{3-7}$)cycloalkyl, unsubstituted or substituted with 1 to 2 substituents each independently R$^5$. In one class of this embodiment, R$^1$ is a heterocycloalkyl containing 1 to 2 heteroatoms independently selected from the group consisting of N, S, and O, wherein the heterocycloalkyl is unsubstituted or substituted with 1 to 2 substituents each independently R$^5$. In one class of this embodiment, R$^1$ is a heteroaryl containing 1 to 3 heteroatoms independently selected from the group consisting of N, O, and S, wherein the heteroaryl ring is unsubstituted or substituted by 1 to 2 substituents each independently R$^5$. In one class of this embodiment, R$^1$ is —S(O)$_2$(C$_{1-3}$)alkyl. In one class of this embodiment, R$^1$ is —O—(C$_{1-3}$)alkyl-aryl, wherein the aryl ring is unsubstituted or substituted by 1 to 2 substituents each independently R$^5$. In one class of this embodiment, R$^1$ is —(CH$_2$)q-aryl, unsubstituted or substituted by 1 to 2 substituents each independently R$^5$. In one subclass of this class, R$^1$ is a fused aryl, unsubstituted or substituted by 1 to 2 substituents each independently R$^5$. In one sub-subclass of this subclass, R$^1$ is spiro[indene-1,4'-piperidinyl], unsubstituted or substituted by 1 to 2 substituents each independently R$^5$.

In one embodiment, X is NH. In one class of this embodiment, R$^1$ is (C$_{3-7}$)cycloalkyl, unsubstituted or substituted with 1 to 2 substituents each independently R$^5$. In one class of this embodiment, R$^1$ is a heterocycloalkyl containing 1 to 2 heteroatoms independently selected from the group consisting of N, S, and O, wherein the heterocycloalkyl is unsubstituted or substituted with 1 to 2 substituents each independently R$^5$. In one class of this embodiment, R$^1$ is a heteroaryl containing 1 to 3 heteroatoms independently selected from the group consisting of N, O, and S, wherein the heteroaryl ring is unsubstituted or substituted by 1 to 2 substituents each independently R$^5$. In one class of this embodiment, R$^1$ is —S(O)$_2$(C$_{1-3}$)alkyl. In one class of this embodiment, R$^1$ is —(CH$_2$)q-aryl, unsubstituted or substituted by 1 to 2 substituents each independently R$^5$. In one subclass of this class, R$^1$ is a fused aryl, unsubstituted or substituted by 1 to 2 substituents each independently R$^5$. In one sub-subclass of this subclass, R$^1$ is spiro[indene-1,4'-piperidinyl], unsubstituted or substituted by 1 to 2 substituents each independently R$^5$.

In one embodiment, X is —(C$_{1-6}$)alkyl-O—. In one class of this embodiment, R$^1$ is (C$_{3-7}$)cycloalkyl, unsubstituted or substituted with 1 to 2 substituents each independently R$^5$. In one class of this embodiment, R$^1$ is a heterocycloalkyl containing 1 to 2 heteroatoms independently selected from the group consisting of N, S, and O heteroatoms, wherein the heterocycloalkyl is unsubstituted or substituted with 1 to 2 substituents each independently R$^5$. In one class of this embodiment, R$^1$ is a heteroaryl containing 1 to 3 heteroatoms independently selected from the group consisting of N, O, and S heteroatoms, wherein the heteroaryl ring is unsubstituted or substituted by 1 to 2 substituents each independently R$^5$. In one class of this embodiment, R$^1$ is —S(O)$_2$(C$_{1-3}$)alkyl. In one class of this embodiment, R$^1$ is —(CH$_2$)q-aryl, unsubstituted or substituted by 1 to 2 substituents each independently R$^5$. In one subclass of this class, R$^1$ is a fused aryl, unsubstituted or substituted by 1 to 2 substituents each independently R$^5$. In one sub-subclass of this subclass, R$^1$ is spiro[indene-1,4'-piperidinyl], unsubstituted or substituted by 1 to 2 substituents each independently R$^5$.

In one class of this embodiment, X is —(CH$_2$)$_4$—O—, —(CH$_2$)$_3$—O—, —(CH$_2$)$_2$—O—, —CH$_2$—O—, —O—(CH$_2$)$_3$—O—. In one subclass of this class, X is —O—(CH$_2$)$_4$—. In one subclass of this class, X is —O—(CH$_2$)$_3$—. In one subclass of this class, X is —O—(CH$_2$)$_2$—. In one subclass of this class, X is —O—CH$_2$—. In one subclass of this class, X is —O—(CH$_2$)$_3$—O—.

In one embodiment, X is —(C$_{1-6}$)alkyl-N(H)—. In one class of this embodiment, R$^1$ is (C$_{3-7}$)cycloalkyl, unsubstituted or substituted with 1 to 2 R$^5$. In one class of this embodiment, R$^1$ is a heterocycloalkyl containing 1 to 2 heteroatoms independently selected from the group consisting of N, S, and O, wherein the heterocycloalkyl is unsubstituted or substituted with 1 to 2 substituents each independently R$^5$. In one class of this embodiment, R$^1$ is a heteroaryl containing 1 to 3 heteroatoms independently selected from the group consisting of N, O, and S, wherein the heteroaryl ring is unsubstituted or substituted by 1 to 2 R$^5$. In one class of this embodiment, R$^1$ is —S(O)$_2$(C$_{1-3}$)alkyl. In one class of this embodiment, R$^1$ is —(CH$_2$)q-aryl, unsubstituted or substituted by 1 to 2 substituents each independently R$^5$. In one subclass of this class, R$^1$ is a fused aryl, unsubstituted or substituted by 1 to 2 substituents each independently R$^5$. In one sub-subclass of this subclass, R$^1$ is spiro[indene-1,4'-piperidinyl], unsubstituted or substituted by 1 to 2 substituents each independently R$^5$.

In one class of this embodiment, X is —(CH$_2$)$_3$—NH—, —(CH$_2$)$_2$—NH—, or —CH$_2$—N(H)—. In one subclass of this class, X is —(CH$_2$)$_3$—NH—, or —CH$_2$—N(H)—. In one subclass of this class, X is —(CH$_2$)$_3$—NH—. In one subclass of this class, X is —(CH$_2$)$_2$—NH—. In one subclass of this class, X is —CH$_2$—N(H)—.

In one embodiment, R$^1$—X— is

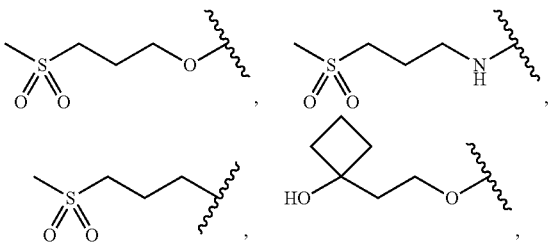

In one embodiment, $R^2$ is methyl, hydroxymethyl, or fluoro.

In one embodiment, $R^3$ is $(C_{1-6})$alkyl. In one embodiment, $R^3$ is halo. In one embodiment, $R^3$ is fluoro or methyl. In one class of this embodiment, $R^3$ is fluoro. In another class of this embodiment, $R^3$ is methyl.

In one embodiment, $R^4$ is $(C_{1-6})$alkyl. In one embodiment, $R^4$ is hydrogen or methyl. In one class of this embodiment, $R^4$ is hydrogen. In one class of this embodiment, $R^4$ is methyl.

In one embodiment, $R^6$ is hydrogen. In one embodiment, $R^6$ is $(C_{1-6})$alkyl. In one embodiment, $R^6$ is $(C_{3-7})$cycloalkyl.

In one embodiment, n is 0. In one embodiment, n is 1. In one embodiment, n is 2. In one embodiment, n is 3.

In one embodiment, m is 0. In one embodiment, m is 1.

In one embodiment, k is 0. In one embodiment, k is 1. In one embodiment, k is 2. In one embodiment, k is 3.

In one embodiment, q is 0. In one embodiment, q is 1. In one embodiment, q is 2. In one embodiment, q is 3.

In one embodiment, the invention relates to compounds of formula I-A:

I-A or a pharmaceutically acceptable salt thereof, wherein $R^1$, $R^2$, $R^3$, $R^4$, $R^5$, X, m, n, k, and q are as previously defined.

In one embodiment, the invention relates to compounds of formula I-B:

I-B or a pharmaceutically acceptable salt thereof, wherein R¹, R², R³, R⁴, R⁵, X, m, n, k, and q are as previously defined.

In one embodiment, the invention relates to compounds of formula I-C:

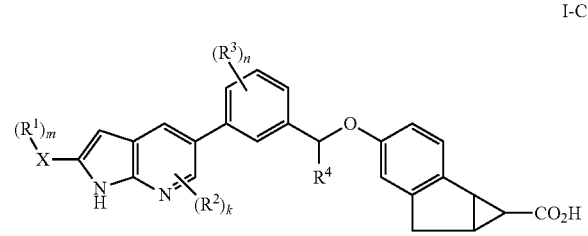

I-C or a pharmaceutically acceptable salt thereof, wherein R¹, R², R³, R⁴, R⁵, X, m, n, k, and q are as previously defined.

In one embodiment, the invention relates to compounds of formula I-D:

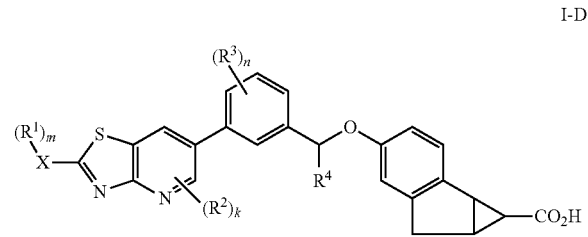

I-D or a pharmaceutically acceptable salt thereof, wherein R¹, R², R³, R⁴, R⁵, X, m, n, k, and q are as previously defined.

In one embodiment, the invention relates to compounds of formula I-E:

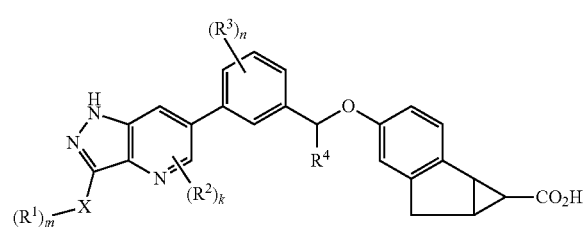

I-E or a pharmaceutically acceptable salt thereof, wherein R¹, R², R³, R⁴, R⁵, X, m, n, k, and q are as previously defined.

Although specific stereochemistries described above are noted, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

As used herein the following definitions are applicable.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. The number of carbon atoms may be specified, for example $(C_{1-3})$alkyl. When no number of carbon atoms is specified, $C_{1-6}$ is intended. Examples of alkyl groups include methyl, ethyl, propyl, isopropyl, butyl, sec- and tert-butyl, pentyl, hexyl, heptyl, octyl, nonyl, and the like.

"Cycloalkyl" means a saturated carbocyclic ring, having a specified number of carbon atoms. The term may also be used to describe a carbocyclic ring fused to an aryl group. The number of carbon atoms in may be specified, for example $(C_{3-8})$cycloalkyl. Examples of cycloalkyl include cyclopropyl, cyclopentyl, cyclohexyl, cycloheptyl, and the like. Cycloalkenyl rings comprise a double bond in the ring. The cycloalkyl group may be fused with another cycloalkyl group, which could also be fused with other cycloalkyl groups. The fusion may form a bridged cycloalkyl group with another cycloalkyl group, which could also be fused with other cycloalkyl groups. The cycloalkyl group could form spiro fusion with another cycloalkyl group, which could also be fused with other cycloalkyl groups. If cycloalkyl is fused with an aryl group, it will be defined as an aryl group. If cycloalkyl is fused with a heteroaryl, it will be defined as a heteroaryl. If the cycloalkyl group is fused with a heterocycloalkyl group, it will be defined as a heterocycloalkyl group.

"Aryl" is commonly used to refer to carbocyclic aromatic structures. The most common aryl groups are phenyl and naphthyl. Phenyl is generally the most preferred aryl group. Aryl can be fused with other groups such as cycloalkyl and heterocyloalkyl. The fusion may be bridged or spiro. An example of a spiro fused aryl is spiro[indene-1,4'-piperidine]. If aryl is fused with a heteroaryl group, it will be defined as a heteroaryl group.

"Heterocyloalkyl" means a saturated or partly unsaturated ring or ring system containing at least one heteroatom selected from N, S and O, wherein the number of heteroatoms and the ring size and the degree of unsaturation (if any) are defined herein. Examples of heterocycles include tetrahydrofuran, piperazine, piperidine, morpholine, oxetane (4-membered cyclic ether), and tetrahydropyran (6-membered cyclic ether). The heterocycloalkyl group may be fused with another group such as a heterocycloalkyl, cycloalkyl, or cyclohexenyl groups, which could also be fused with other ring systems. An example of a fused heterocycloalkyl group is (3aR,6aR)-hexahydrofuro[3,2-b]furan. The fusion may form a bridged heterocycloalkyl group with another group such as a heterocycloalkyl, cycloalkyl, or cyclohexenyl groups, which could also be fused with other ring systems. An example of a bridged heterocycloalkyl group is (1R,5S)-8-azabicyclo[3.2.1]octan-3-ol. The heterocycloalkyl group could form spiro fusion with another group such as a heterocycloalkyl, cycloalkyl, or cyclohexenyl groups, which could also be fused with other ring systems. If heterocycloalkyl is fused with an aryl group, it will be defined as an aryl group. If heterocycloalkyl is fused with a heteroaryl, it will be defined as a heteroaryl.

"Heteroaryl" means a heteroaromatic ring containing at least one ring heteroatom selected from N, O and S (including SO and SO$_2$), as defined more specifically herein. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, indazolyl, benzofuranyl, benzothiophene (including S-oxide and dioxide), furo(2,3-b)pyridyl, quinolyl, indolyl, isoquinolyl, quinazolinyl, dibenzofuranyl, and the like. The heteroaryl group may be fused with other groups such as cycloalkyl, cycloalkenyl, heterocycloalkyl, aryl or other heteroaryl groups. The fusions may form bridges and spiro groups.

"Halogen" includes fluorine, chlorine, bromine and iodine.

"Hydroxyalkyl" means "alkyl" as defined above wherein one or more of the hydrogen of the alkyl group are replaced with hydroxy groups.

"Haloalkyl" means "alkyl" as defined above wherein one or more of the hydrogen atoms are replaced with a halogen. Examples include bromomethane, trifluoromethane, and chloroethane.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In a specific embodiment, the pharmaceutically acceptable salt are ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases:

(1) non-insulin dependent diabetes mellitus (Type 2 diabetes);
(2) hyperglycemia;
(3) Metabolic Syndrome/syndrome X;
(4) obesity;
(5) ischemia and myocardial infarction;
(6) neurological disorders such as Alzheimer's disease, schizophrenia, and impaired cognition;
(7) hypercholesterolemia;
(8) hypertriglyceridemia (elevated levels of triglyceride-rich-lipoproteins);
(9) mixed or diabetic dyslipidemia;
(10) low HDL cholesterol;
(11) high LDL cholesterol;
(12) hyperapo-beta-liproteinemia;
(13) atherosclerosis;
(14) inflammation related disorders;
(15) type 1 diabetes; and
(16) insulin resistance.

Preferred uses of the compounds may be for the treatment of one or more of the following diseases by administering a therapeutically effective amount to a patient in need of treatment. The compounds may be used for manufacturing a medicament for the treatment of one or more of these diseases:

(1) Type 2 diabetes, and specifically hyperglycemia associated with Type 2 diabetes;
(2) Metabolic Syndrome;
(3) obesity; and
(4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hyperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The compounds described herein and combinations comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease ("CHD") event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the compounds and combinations of the present invention to a dyslipidemic subject. Prevention of dyslipidemia refers to the administration of the compounds and the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dyslipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver, cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk or diagnostic factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Additionally, in the treatment or prevention of conditions which require agonism of GPR40 receptor activity, an appropriate dosage level will generally be about 0.01 to 500 mg per kg patient body weight per week, which can be administered in single or multiple doses. Preferably, the dosage level will be about 0.1 to about 250 mg/kg per week; more preferably about 0.5 to about 100 mg/kg per week. A suitable dosage level may be about 0.01 to 250 mg/kg per week, about 0.05 to 100 mg/kg per week, or about 0.1 to 50 mg/kg per week. Within this range the dosage may be 0.05 to 0.5, 0.5 to 5 or 5 to 50 mg/kg per week. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may also be administered on a regimen of 1 to 4 times per week, preferably once or twice per week.

When treating or preventing diabetes mellitus and/or hyperglycemia or hypertriglyceridemia or other diseases for which compounds of the present invention are indicated, generally satisfactory results are obtained when the compounds of the present invention are administered at a weekly dosage of from about 0.1 mg to about 100 mg per kilogram of animal body weight, preferably given as a single weekly dose or in divided doses two to six times a week, or in sustained release form. For most large mammals, the total weekly dosage is from about 1.0 mg to about 1000 mg, preferably from about 1 mg to about 50 mg. In the case of a 70 kg adult human, the total weekly dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds of formula I or the other drugs may have utility, where the combination of the drugs together are safer or more effective than either drug alone. Such other drug(s) may be administered, by a route and in an amount commonly used therefore, contemporaneously or sequentially with a compound of formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on the same or different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I.

Examples of other active ingredients that may be administered separately or in the same pharmaceutical composition in combination with a compound of the formulas described herein include, but are not limited to:

(1) dipeptidyl peptidase-IV (DPP-4) inhibitors (e.g., sitagliptin, alogliptin, omarigliptin, linagliptin, vildagliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., MK-3577, MK-0893, LY-2409021 and KT6-971);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, torcetrapib, and AT-03);

(18) inhibitors of fructose 1,6-bisphosphatase, (e.g., MB-07803, and such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators (e.g., MB-11055);

(21) other agonists of the G-protein-coupled receptors: (i) GPR-109, (ii) GPR-119 (e.g., MBX2982 and PSN821), and (iii) GPR-120 (e.g., KDT-501);

(22) SSTR3 antagonists (e.g., pasireotide, and such as those disclosed in WO 2009/011836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., LIK-066, ASP1941, SGLT-3, ertugliflozin, empagliflozin, dapagliflozin, canagliflozin, BI-10773, PF-04971729, remogliflozin, luseogliflozin, tofogliflozin, ipragliflozin, and LX-4211);

(27) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2;

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR) (eg., sodium taurocholate);

(31) ileal bile acid transporter inhibitors (eg., elobixibat);

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies and inhibitors, (e.g., gevokizumab, canakinumab, danazol, AC-201, and BLX-1002); and

(36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), omarigliptin, trelagliptin, teneligliptin, bisegliptin, anagliptin, LC15-0444, vildagliptin, saxagliptin, alogliptin, melogliptin, linagliptin, gosogliptin, evogliptin, gemigliptin, and pharmaceutically acceptable salts thereof, and fixed-dose combinations of these compounds with metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein include, but are not limited to:

(1) (2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2) (2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(3) (2R,3S,5R)-2-(2,5-difluorophenyl)tetrahydro-5-(4,6-dihydropyrrolo[3,4-c]pyrazol-5(1H)-yl)tetrahydro-2H-pyran-3-amine;

(4) (3R)-4-[(3R)-3-amino-4-(2,4,5-trifluorophenyl)butanoyl]-hexahydro-3-methyl-2H-1,4-diazepin-2-one;

(5) 4-[(3R)-3-amino-4-(2,5-difluorophenyl)butanoyl]hexahydro-1-methyl-2H-1,4-diazepin-2-one hydrochloride; and (6) (3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Antiobesity compounds that can be combined with compounds of formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $β_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging anti-obesity drugs," *Expert Opin. Emerging Drugs*, 8: 217-237 (2003); J. A. Fernandez-Lopez, et al., "Pharmacological Approaches for the Treatment of Obesity," *Drugs*, 62: 915-944 (2002); and K. M. Gadde, et al., "Combination pharmaceutical therapies for obesity," *Exp. Opin. Pharmacother.*, 10: 921-925 (2009).

Glucagon receptor antagonists that can be used in combination with the compounds of formula I include, but are not limited to:

(1) (S)-3-(4-(1-(3-(2-fluoro-5-(trifluoromethyl)phenyl)-5-(6-methoxynaphthalen-2-yl)-1H-pyrazol-1-yl)ethyl)benzamido)propanoic acid;

(2) 3-(4-(1-(3-(2-fluoro-5-(trifluoromethyl)phenyl)-5-(6-methoxynaphthalen-2-yl)-1H-pyrazol-1-yl)ethyl)benzamido)propanoic acid;

(3) 3-(4-(1-((4'-(tert-butyl)-2,6-dimethyl-[1,1'-biphenyl]-4-yl)oxy)-4,4,4-trifluorobutyl)benzamido)propanoic acid;

(4) 3-(4-(1-(2,6-dimethyl-4'-(trifluoromethyl)-[1,1'-biphenyl]-4-yl)oxy)-4,4-dimethylpentyl)benzamido)propanoic acid;

(5) (S)-3-(4-(1-(3-(3,5-dichlorophenyl)-5-(6-methoxynaphthalen-2-yl)-1H-pyrazol-1-yl)ethyl)benzamido)propanoic acid;

(6) 3-(4-(1-(3-(3,5-dichlorophenyl)-5-(6-methoxynaphthalen-2-yl)-1H-pyrazol-1-yl)ethyl)benzamido)propanoic acid;

(7) 3-(4-((1R,2S)-1-(4-chlorophenyl)-1-(7-fluoro-5-methyl-1H-indol-3-yl)pentan-2-yl)benzamido)propanoic acid;

(8) 3-(4-(1-(4-chlorophenyl)-1-(7-fluoro-5-methyl-1H-indol-3-yl)pentan-2-yl)benzamido)propanoic acid;

(9) 3-(4-((1R,2S)-1-(4-chlorophenyl)-1-(5,7-dichloro-1H-indol-3-yl)pentan-2-yl)benzamido)propanoic acid;
(10) 3-(4-(1-(4-chlorophenyl)-1-(5,7-dichloro-1H-indol-3-yl)pentan-2-yl)benzamido)propanoic acid;
(11) 3-(4-(1-((4'-(tert-butyl)-2,6-dimethyl-[1,1'-biphenyl]-4-yl)oxy)-2-methylpropyl)benzamido)propanoic acid;
(12) N-((2H-tetrazol-5-yl)methyl)-4-((1R)-1-(8-(tert-butyl)-3-(3,5-dichlorophenyl)-2-oxo-1,4-diazaspiro[4.5]dec-3-en-1-yl)-4,4-dimethylpentyl)benzamide;
(13) N-((2H-tetrazol-5-yl)methyl)-4-(1-(8-(tert-butyl)-3-(3,5-dichlorophenyl)-2-oxo-1,4-diazaspiro[4.5]dec-3-en-1-yl)-4,4-dimethylpentyl)benzamide;
(14) (S)-3-(4-(1-(3-(2-ethoxy-5-(trifluoromethyl)phenyl)-5-(6-methoxynaphthalen-2-yl)-1H-pyrazol-1-yl)ethyl)benzamido)propanoic acid;
(15) 3-(4-(1-(3-(2-ethoxy-5-(trifluoromethyl)phenyl)-5-(6-methoxynaphthalen-2-yl)-1H-pyrazol-1-yl)ethyl)benzamido)propanoic acid;
(16) 3-(4-((1R,2S)-1-(6-chloro-8-methylquinolin-4-yl)-1-(4-chlorophenyl)pentan-2-yl)benzamido)propanoic acid; and
(17) 3-(4-(1-(6-chloro-8-methylquinolin-4-yl)-1-(4-chlorophenyl)pentan-2-yl)benzamido)propanoic acid; and pharmaceutically acceptable salts thereof.

In another aspect of the invention, a pharmaceutical composition is disclosed which comprises one or more of the following agents:
(a) a compound of structural formula I;
(b) one or more compounds selected from the group consisting of:
(1) dipeptidyl peptidase-IV (DPP-4) inhibitors;
(2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814;
(3) sulfonylurea and non-sulfonylurea insulin secretagogues, (e.g., tolbutamide, glyburide, glipizide, glimepiride, mitiglinide, and meglitinides, such as nateglinide and repaglinide);
(4) α-glucosidase inhibitors (e.g., acarbose, voglibose and miglitol);
(5) glucagon receptor antagonists;
(6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA: cholesterol acyltransferase inhibitors (e.g., avasimibe);
(7) HDL-raising drugs, such as niacin or a salt thereof and extended-release versions thereof; MK-524A, which is a combination of niacin extended-release and the DP-1 antagonist MK-524; and nicotinic acid receptor agonists;
(8) antiobesity compounds;
(9) agents intended for use in inflammatory conditions, such as aspirin, non-steroidal anti-inflammatory drugs (NSAIDs), glucocorticoids, and selective cyclooxygenase-2 (COX-2) inhibitors;
(10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers);
(11) glucokinase activators (GKAs) (e.g., AZD6370, GKM-001, TMG-123, HMS-5552, DS-7309, PF-04937319, TTP-399, ZYGK-1);
(12) inhibitors of 11β-hydroxysteroid dehydrogenase type 1 (e.g., such as those disclosed in U.S. Pat. No. 6,730,690; WO 03/104207; and WO 04/058741);
(13) inhibitors of cholesteryl ester transfer protein (CETP), (e.g., torcetrapib, anacetrapib, and AT-03);
(14) inhibitors of fructose 1,6-bisphosphatase (e.g., MB-07803, and such as those disclosed in U.S. Pat. Nos. 6,054,587; 6,110,903; 6,284,748; 6,399,782; and 6,489,476);
(15) inhibitors of acetyl CoA carboxylase-1 or 2 (ACC1 or ACC2);
(16) AMP-activated Protein Kinase (AMPK) activators (e.g., MB-11055);
(17) agonists of the G-protein-coupled receptors: (i) GPR-109, (ii) GPR-119 (e.g., MBX2982, and PSN821), and (iii) GPR-120 (e.g., KDT-501);
(18) SSTR3 antagonists (e.g., pasireotide, and such as those disclosed in WO 2009/011836);
(19) neuromedin U receptor agonists (e.g., such as those disclosed in WO2009/042053, including, but not limited to, neuromedin S (NMS));
(20) inhibitors of stearoyl-coenzyme A delta-9 desaturase (SCD);
(21) GPR-105 antagonists (e.g., such as those disclosed in WO 2009/000087);
(22) inhibitors of glucose uptake, such as sodium-glucose transporter (SGLT) inhibitors and its various isoforms, such as SGLT-1; SGLT-2 (e.g., LIK-066, ertuglifozin, ASP1941, luseogliflozin, BI10773, tofogliflozin, LX4211, canagliflozin, dapagliflozin and remogliflozin; and SGLT-3);
(23) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2;
(24) inhibitors of fatty acid synthase;
(25) inhibitors of acyl coenzyme A:monoacylglycerol acyltransferase 1 and 2 (MGAT-1 and MGAT-2);
(26) agonists of the TGR5 receptor (also known as GPBAR1, BG37, GPCR19, GPR131, and M-BAR) (eg., sodium taurocholate);
(28) bromocriptine mesylate and rapid-release formulations thereof, and
(29) IL-1b antibodies and inhibitors (e.g., gevokizumab, canakinumab, danazol, AC-201, and BLX-1002); and
(c) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s). The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs, cats, and horses.

The weight ratio of the compound of the Formula I to the second active ingredient may be varied and will depend upon the effective dose of each ingredient. Generally, an effective dose of each will be used. Thus, for example, when a compound of the Formula I is combined with a DPP-IV inhibitor the weight ratio of the compound of the Formula I to the DPP-IV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The following Examples are provided to illustrate the invention and are not to be construed as limiting the invention in any manner. The scope of the invention is defined by the appended claims.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formulae I, or I-A through I-E. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

List of Abbreviations

Ac is acetyl; ACN is acetonitrile; AcO is acetoxy; Alk is alkyl; APCI is atmospheric pressure chemical ionization; aq or aq. is aqueous; Ar is aryl; Boc is tert-butoxycarbonyl; br is broad; t-BuOK is potassium tert-butoxide; ° C. is degrees celsius; Cbz is benzyloxycarbonyl; CH$_2$Cl$_2$ is dichloromethane; conc or conc. is concentrated; d is doublet; DAST is (diethylamino)sulfur trifluoride; DIAD is diisopropyl azodicarboxylate; DCM is dichloromethane; DIPEA is N,N-diisopropylethylamine; DMAP is 4-dimethylaminopyridine; DMF is N,N-dimethylformamide; DMSO is dimethylsulfoxide; dppf is 1,1'-bis(diphenyl-phosphino)ferrocene; ESI is electrospray ionization; EA or EtOAc is ethyl acetate; Et is ethyl; EtMgBr is ethyl magnesium bromide; EtOH is ethanol; g or gm is gram(s); h or hr or hrs is hour(s); HPLC is high pressure liquid chromatography; HOAc or AcOH is acetic acid; kg is kilogram(s); KOH is potassium hydroxide; KOAc is potassium acetate; L is liter; LC is liquid chromatography; LC-MS is liquid chromatography-mass spectroscopy; LDA is lithium diisopropyl amide; LiOH is lithium hydroxide; m is multiplet; m-CPBA, MCPBA, or mCPBA is meta-chloroperbenzoic acid; mL is milliliter; min or mins is minute(s); mol is mole(s); mmol is mmole(s); mg is milligram(s); MeMgBr is methyl magnesium bromide; MeOH is methyl alcohol; MgSO$_4$ is magnesium sulfate; MS is mass spectroscopy; MsCl or Ms-Cl is methane sulfonyl chloride; N is normal; Na(AcO)$_3$BH is sodium triacetoxy borohydride; NaOH is sodium hydroxide; Na$_2$SO$_4$ is sodium sulfate; NH$_4$OAc is ammonium acetate; NBS is N-bromo succinamide; NIS is N-iodo succinamide; NMO is 4-methyl morpholine N-oxide; NMP is 1-methyl-2-pyrrolidinone; NMR is nuclear magnetic resonance spectroscopy; PE is petroleum ether; PG is protecting group; P(Cy)$_3$ is tricyclohexyl phosphine; Pd$_2$(dba)$_3$ is tris(dibenzylideneacetone) dipalladium(0); Pd[P(t-Bu)$_3$]$_2$ is bis(tri-tert-butylphosphine) palladium (0); Pd(dppf)Cl$_2$ is [1,1'-bis(diphenylphosphino) ferrocene]dichloro-palladium (II); PMB is para-methoxybenzyl; PMBCl is para-methoxybenzyl chloride; preparative is preparative; prep. SFC is supercritical-fluid chromatography; TLC or prep-TLC, or preparative TCL is preparative thin layer chromatography; RBF is round bottom flask; RCM is ring closing metathesis reaction; rt or r.t. or RT is room temperature; s is singlet; s-phos is 2-Dicyclohexylphosphino-2',6'-dimethoxybiphenyl; t is triplet; TBTU is N,N,N',N'-Tetramethyl-O-(benzotriazol-1-yl)uronium tetrafluoroborate; TEA is triethyl amine; THF istetrahydrofuran; Ti(OiPr)$_4$ is titanium isopropoxide; TFA is trifluoroacetic acid; TLC is thin-layer chromatography; TosCl is p-toluene sulfonyl chloride; pTSA or TsOH is p-toluenesulfonic acid, and xphos is 2-dicyclohexylphosphino-2',4',6'-triisopropylbiphenyl.

Several methods for preparing the compounds of this invention are illustrated in the following Schemes and Examples. Starting materials are either commercially available or made by known procedures in the literature or as illustrated. The present invention further provides processes for the preparation of compounds of structural formulae I and I-A through I-E as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention. All temperatures are degrees Celsius unless otherwise noted.

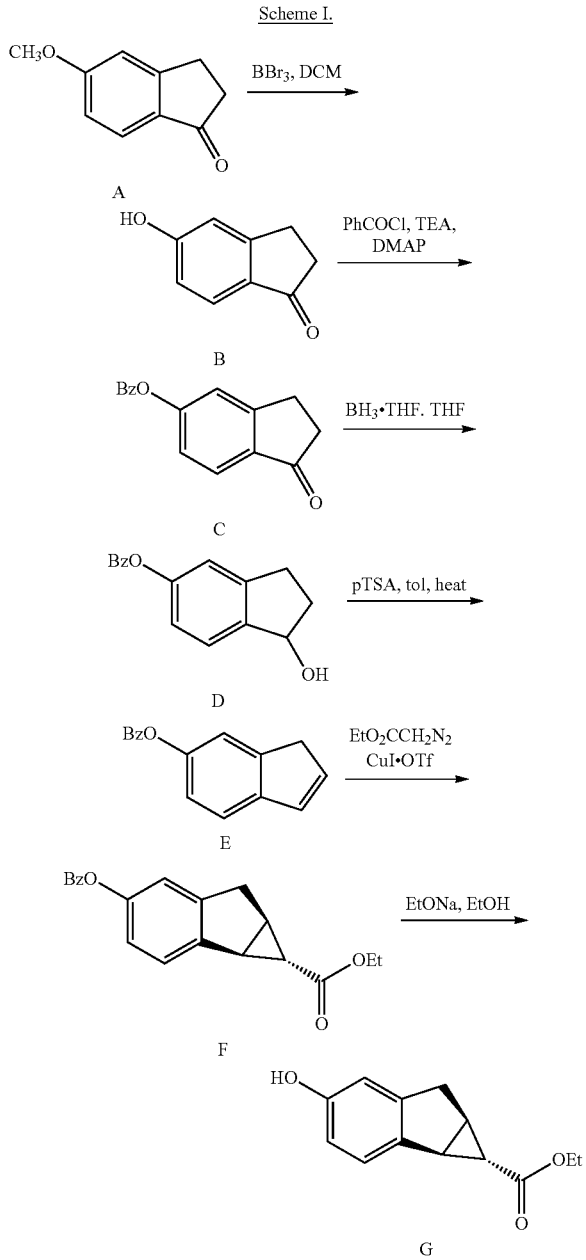

In Scheme I, methoxy-indanone A is demethylated with boron tribromide to afford phenol B. The phenol in B is acylated with benzoyl chloride in the presence of triethylamine and 4-DMAP to give ester C. The ketone in C is reduced with borane-THF complex to alcohol D which is dehydrated in the presence of pTSA in refluxing toluene to yield indene E. Reaction of E with ethyl diazoacetate in the presence of copper(I)iodide-triflate affords tricyclic ester F. Hydrolysis of the phenyl ester with sodium ethoxide in ethanol yields key intermediate G.

Scheme II.

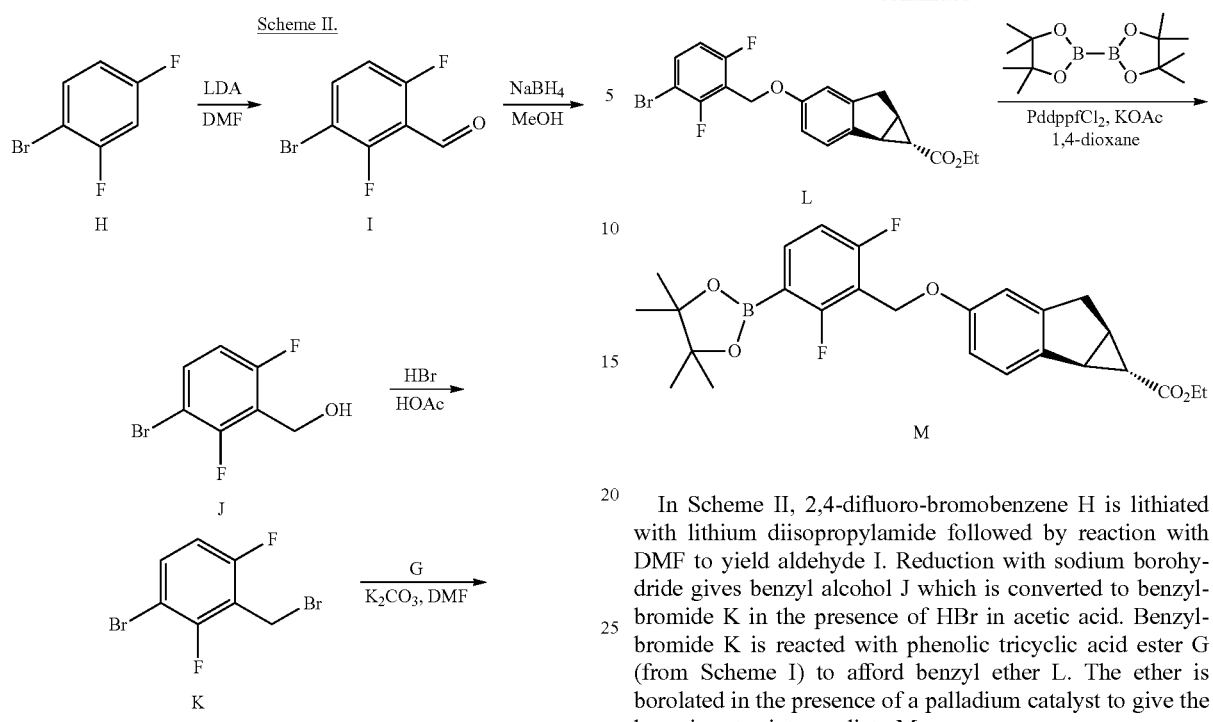

In Scheme II, 2,4-difluoro-bromobenzene H is lithiated with lithium diisopropylamide followed by reaction with DMF to yield aldehyde I. Reduction with sodium borohydride gives benzyl alcohol J which is converted to benzyl-bromide K in the presence of HBr in acetic acid. Benzyl-bromide K is reacted with phenolic tricyclic acid ester G (from Scheme I) to afford benzyl ether L. The ether is borolated in the presence of a palladium catalyst to give the boronic ester intermediate M.

Scheme III.

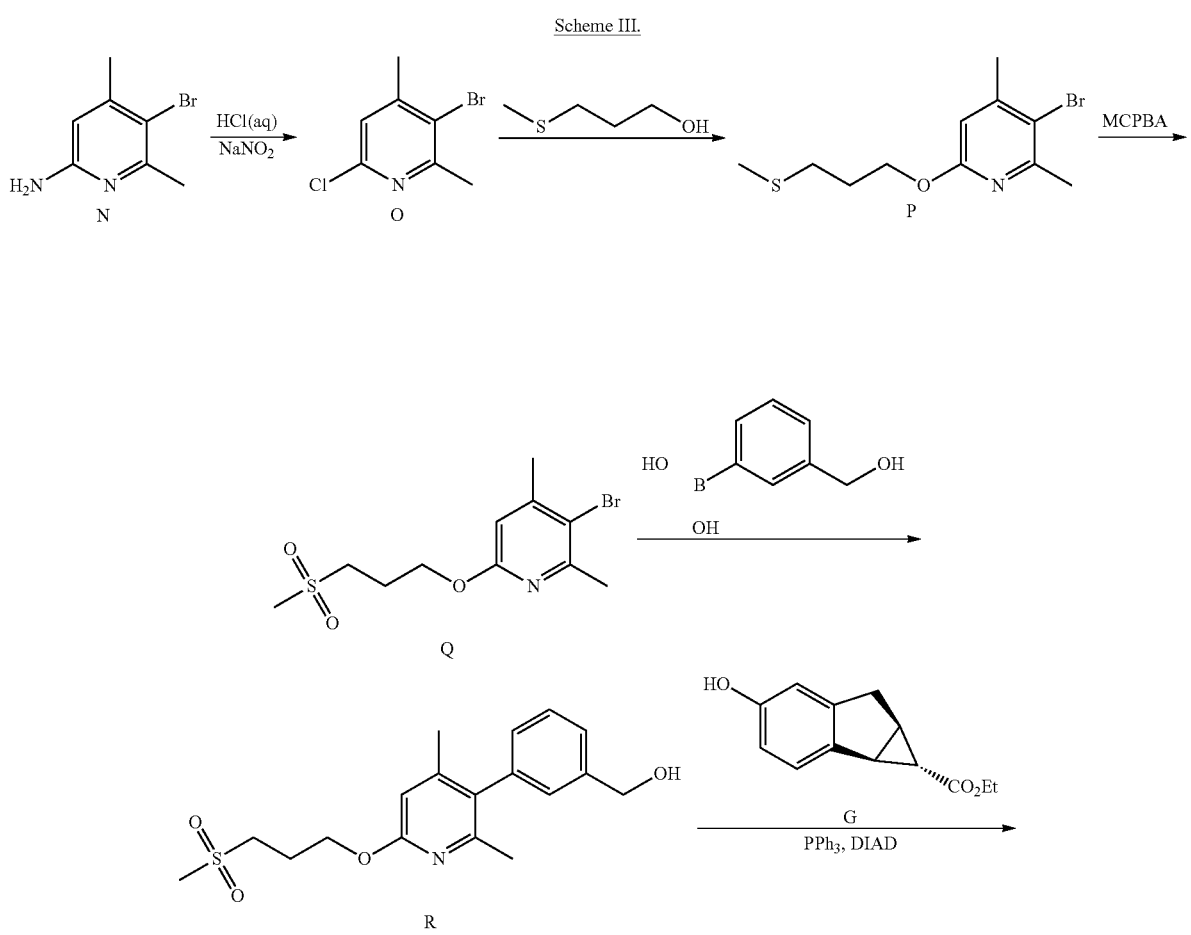

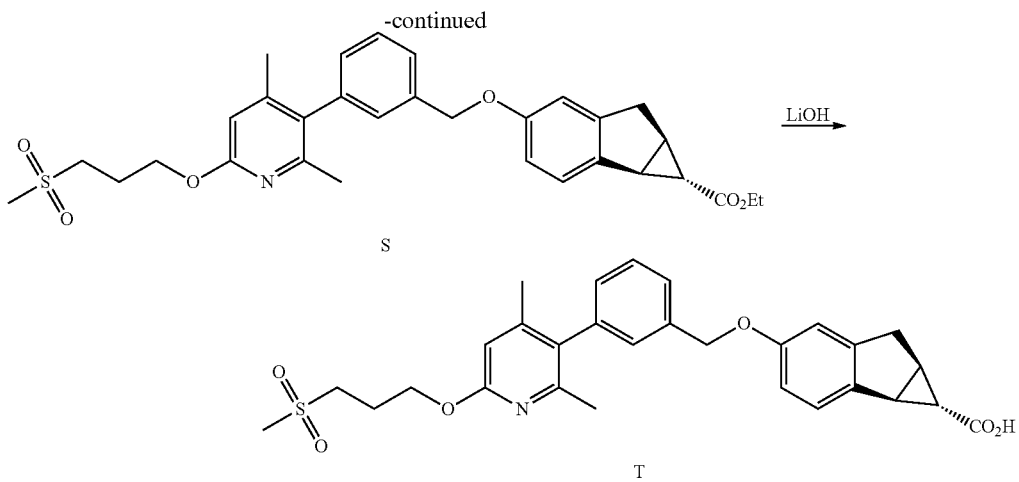

Compounds of the current invention may be prepared according to the methodology outlined in Scheme III. 2-Amino-5-bromo-4,6-dimethylpyridine N is diazotized with sodium nitrite in the presence of HCl to afford 5-bromo-2-chloro-4,6-dimethylpyridine O. Reaction of O with 3-methylthio-n-propanol gives ether P which is subsequently oxidized with peracid to afford methylsulfonyl-propyloxy-pyridine derivative Q. C—C coupling of bromo-pyridine Q with hydroxymethylphenyl boronic acid in the presence of a catalyst yields biarylmethyl alcohol R. Reaction of tricyclic phenol G under Mitsunobu conditions affords ester S. Subsequent hydrolysis gives fully elaborated acid T.

Scheme IV

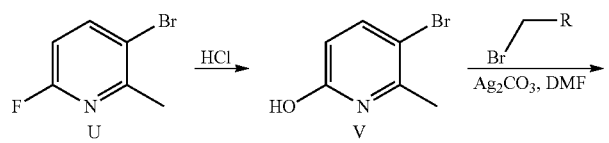

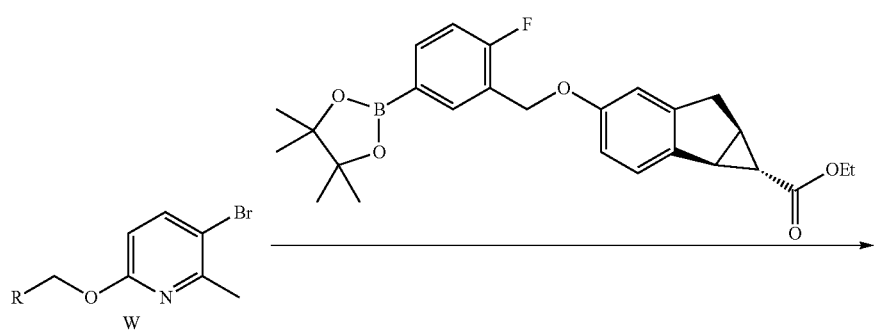

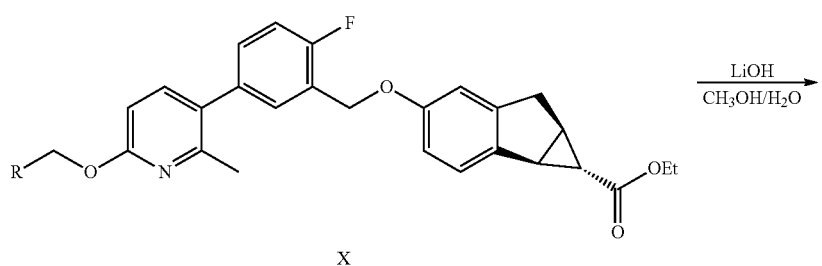

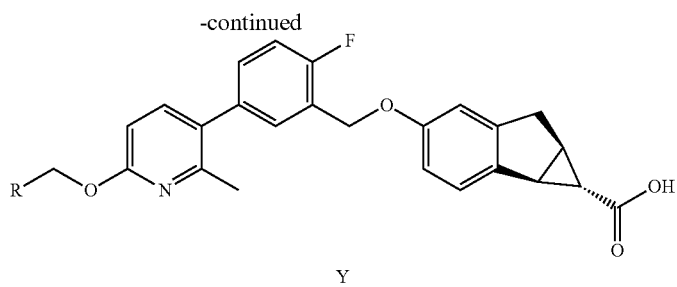

Y

As outlined in Scheme IV, 3-bromo-6-fluoro-2-methyl-pyridine U is treated with aqueous hydrochloric acid to yield hydroxypyridine V which is reacted with an alkylhalide in the presence of silver carbonate to yield ether W. The bromine in W is reacted under Suzuki C—C coupling conditions to give ester X which is hydrolyzed in the presence of aqueous base to yield the desired acid Y.

Aminopyridine analogues are prepared by the method outlined in Scheme V. Fluoropyridine A' is reacted with an amine to afford substituted aminopyridine B'. The bromide in B' is reacted under Suzuki C—C coupling conditions to yield ester C' which is subsequently hydrolyzed to yield target acid D'.

Scheme V

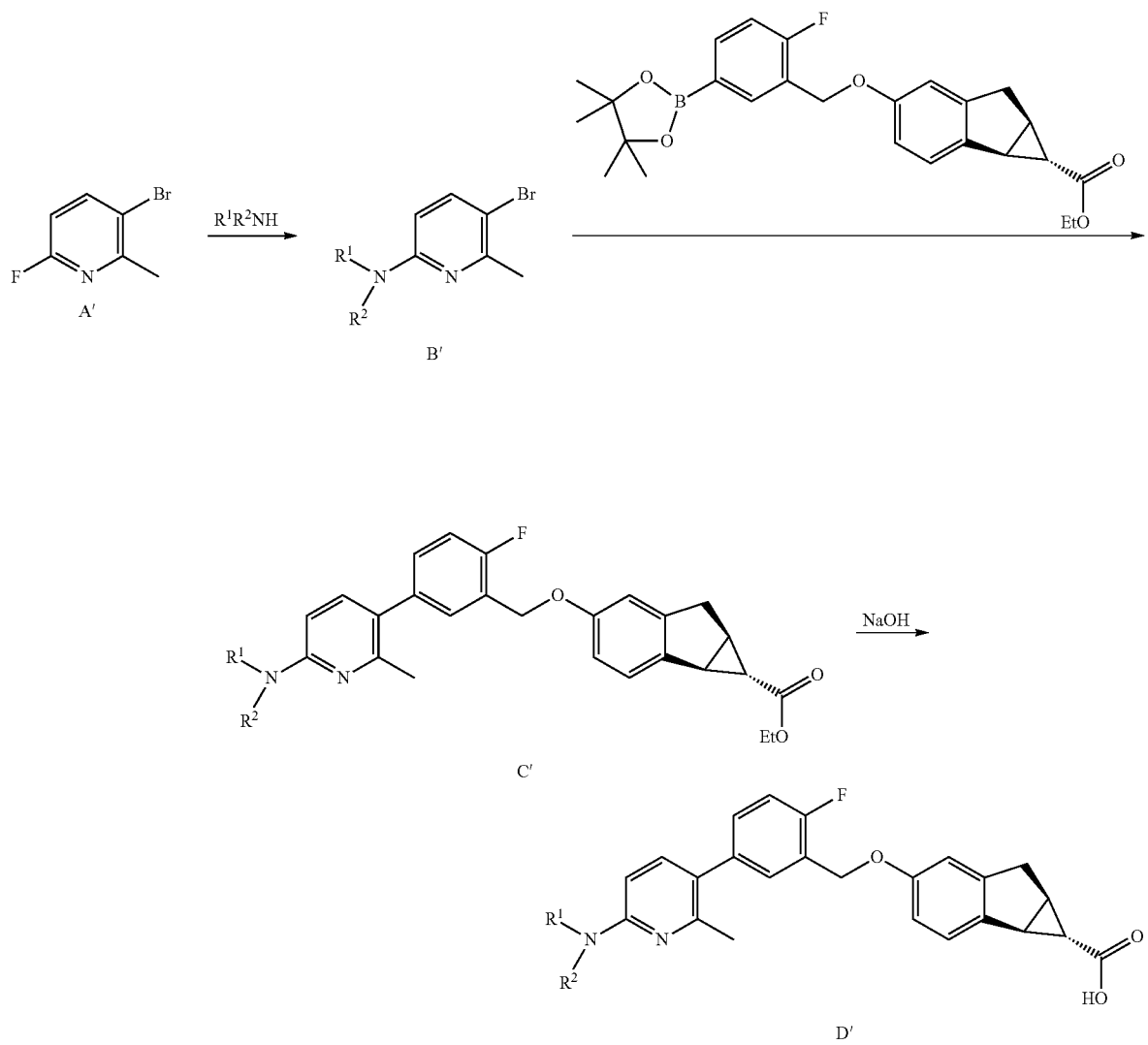

Reference Example 1

(1S,1aS,6aR)-4-hydroxy-1,1a,6,6a-tetrahydrocyclo-propa[a]indene-1-carboxylic acid, ethyl ester

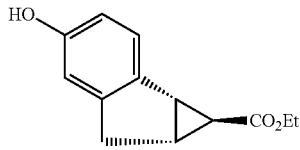 [SMILES: CCOC(=O)[C@H]1[C@@H]2Cc3cc(O)ccc3[C@@H]21]

Step A. 5-Hydroxyindan-1-one

To a mixture of 5-methoxyindan-1-one (200 g, 1.235 mol) in 2 L of anhydrous dichloromethane was added BBr$_3$ (234 mL, 2.469 mol) slowly at −78° C. The mixture was warmed slowly to rt and stirred overnight. Then the mixture was poured slowly into ice-water (2 L) with vigorous stirring for 30 min. The result mixture was filtered to give a solid. The filtrate was separated, and the aqueous phase was extracted with EtOAc (2×500 mL). The combined organic phases were washed with brine (1 L) and dried over Na$_2$SO$_4$ and concentrated to dryness to obtain another batch of solid. The combined solids were dried in vacuo to give the title compound. $^1$H-NMR (400 MHz, MeOD): δ 7.55 (d, J=8.1 Hz, 1H), 6.78-6.84 (m, 2H), 3.03-3.06 (m, 2H), 2.60-2.63 (m, 2H) ppm.

Step B. 1-Oxo-2,3-dihydro-1H-inden-5-yl benzoate

Benzoyl chloride (126.9 g, 0.900 mol) was added slowly to a stirred mixture of the product of Step A (121 g, 0.818 mol), triethylamine (99.1 g, 0.982 mol) and catalytic amount of DMAP (1 g, 8.18 mmol) in dichloromethane (1 L) at rt under nitrogen. The mixture was stirred overnight and diluted with dichloromethane (1 L). Then the solution was washed with water, hydrochloric acid (0.5 M, 2×1 L), and brine. The organic layer was dried over MgSO$_4$, filtered and the solvent was evaporated under reduced pressure. The residue was dried in vacuo to give the tile compound. $^1$H-NMR (400 MHz, CDCl$_3$): δ 8.19-8.22 (m, 2H), 7.83 (d, J=8.1 Hz, 1H), 7.65-7.69 (m, 1H), 7.52-7.55 (m, 2H), 7.37 (s, 1H), 7.22 (dd, J=8.1 Hz, J=2.0 Hz, 1H), 3.17-3.20 (m, 2H), 2.73-2.76 (m, 2H) ppm.

Step C. 1-Hydroxy-2,3-dihydro-1H-inden-5-yl benzoate

BH$_3$·THF (1 M solution in THF, 773.8 mL, 773.8 mmol) was added dropwise to a stirred mixture of the product of Step B (195 g, 773.8 mmol) in anhydrous THF at 0° C. under nitrogen, and the reaction mixture was stirred at rt overnight. The mixture was cooled to 0° C. and carefully quenched with methanol (500 mL). Cooling bath was removed, and the solution was stirred until bubbling stopped. The solvent was evaporated under reduce pressure. The residue was purified by column chromatography on silica gel (EtOAc:PE=1:10) to give the title compound. $^1$H-NMR (400 MHz, CDCl$_3$): δ 8.19-8.22 (m, 2H), 7.62-7.66 (m, 1H), 7.52 (t, J=7.6 Hz, 2H), 7.45 (d, J=8.1 Hz, 1H), 7.06-7.10 (m, 2H), 5.25 (t, J=6.1 Hz, 1H), 3.05-3.12 (m, 1H), 2.81-2.89 (m, 1H), 2.49-2.58 (m, 1H), 1.96-2.04 (m, 2H) ppm.

Step D. 1H-Inden-6-yl benzoate

TsOH (850 mg, 9.449 mmol) was added to a stirred mixture of 1-hydroxy-2,3-dihydro-1H-inden-5-yl benzoate (120 g, 472.441 mmol) and MgSO$_4$ (113.4 g, 944.882 mmol) in toluene at rt under nitrogen, and the reaction mixture was stirred at 90-100° C. overnight. The solid was filtered off and the filtrate was concentrated under reduced pressure. The residue was purified by column chromatography (PE) to give the title compound. $^1$H-NMR (400 MHz, CDCl$_3$): δ 8.22-8.24 (m, 2H), 7.62-7.66 (m, 1H), 7.50-7.54 (m, 2H), 7.42 (d, J=8.1 Hz, 1H), 7.34 (d, J=1.2 Hz, 1H), 7.12 (dd, J=8.1 Hz, J=2.0 Hz, 1H), 6.88-6.90 (m, 1H), 6.57-6.59 (m, 1H), 3.44 (s, 2H) ppm.

Step E (1S,1aS,6aR)-4-(benzoyloxy)-1,1a,6,6a-tetra-hydrocyclopropa[a]indene-1-carboxylic acid, ethyl ester (+)-2,2'-Isopropylidenebis[(4R)-4-phenyl-2-oxazoline (849 mg, 2.542 mmol) was added to a stirring solution of 1H-inden-6-yl benzoate from Step D (30 g, 127.119 mmol) and Cu(I) triflate (657 mg, 1.271 mmol) in dichloromethane (300 mL) at rt under nitrogen. The solution was stirred at rt for 4 h. A solution of ethyl diazoacetate (29 g, 254.237 mmol) in dichloromethane (100 mL) was added at rt through a syringe pump over a period of 72 h. Solvent was removed under reduce pressure, and the residue was purified by column chromatography on silica gel (PE) to give the title compound (about 50% enantiomeric excess). MS: m/z 323.2 (M+1)$^+$.

Step F. (1S,1aS,6aR)-4-hydroxy-1,1a,6,6a-tetrahy-drocyclopropa[a]indene-1-carboxylic acid, ethyl ester The benzoyl ester from Step E (30 g, 93.168 mmol) was dissolved in anhydrous ethanol (300 mL) and cooled to 0° C. under nitrogen. A solution of EtONa in EtOH (46.6 mL, 93.200 mmol) was slowly added. The resulting solution was stirred at room temperature for 4 hr. Most of the solvent was removed and the residue was carefully partitioned between ethyl acetate (200 mL) and HCl (aq, 0.5 M, 300 mL) and extracted with ethyl acetate (200 mL). The combined organic solution was washed with brine (200 mL), dried with sodium sulfate, and evaporated. The crude product was purified on silica gel column (EtOAc/PE=1:20) and then chiral prep-HPLC to obtain the pure title compound (enantiomeric excess: >95%). MS: m/e 219.0 (M+1)$^+$.

Reference Example 2

3-Bromo-2,4-dimethyl-6-(3-(methylsulfonyl)propoxy)pyridine

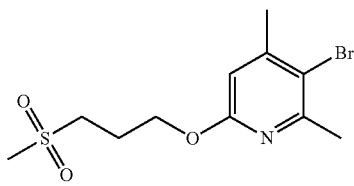 [SMILES: Cc1cc(OCCCS(C)(=O)=O)nc(C)c1Br]

Step A. 3-Bromo-6-chloro-2,4-dimethylpyridine

To a mixture of 2-amino-5-bromo-4,6-dimethylpyridine (5.03 g, 25 mmol) in conc HCl (30 mL) which was cooled to −5° C., was added a solution of sodium nitrite (5.18 g, 75 mmol) in water (20 mL) dropwise over 30 min, while maintaining the temperature of the reaction between −5° C. and 5° C. After the addition was complete, the reaction was stirred for 1 h, and then the cooling bath was removed and the reaction was warmed to room temperature and stirred for 24 hrs. The reaction was poured into ice and 5N NaOH was added to adjust the PH of solution to 7. The mixture was extracted with EtOAc for three times. The combined organic layers were dried over anhydrous $Na_2SO_4$, filtered and concentrated. The residue was purified by flash chromatography on silica gel with PE:EA=20:1 to the title compound. MS (ESI) m/e (M+H$^+$): 222.0/220.0.

Step B. 3-bromo-2,4-dimethyl-6-(3-(methylthio)propoxy)pyridine

A mixture of 3-methylsulfanyl-propan-1-ol (212 mg, 2.0 mmol) and 3-bromo-6-chloro-2,4-dimethylpyridine (440 mg, 2.0 mmol), t-BuOK (250 mg, 2.2 mmol) in anhydrous THF was heated to reflux for 2 hrs. The mixture was partitioned with water and EtOAc, separated and the aqueous solution was extracted with EtOAc two times. The organic layers were concentrated to afford a residue, which was purified by flash chromatography on silica gel to give the title compound. MS (ESI) m/e (M+H$^+$): 292.0/290.0.

Step C. 3-bromo-2,4-dimethyl-6-(3-(methylsulfonyl)propoxy)pyridine

To a solution of 3-bromo-2,4-dimethyl-6-(3-(methylthio)propoxy)pyridine (378 mg, 1.3 mmol) in dry DCM (12 mL) with ice-bath cooling was added MCPBA (580 mg, 2.86 mmol). The resulting mixture was stirred at 0° C. for 2 hrs. Then the reaction was quenched by aqueous solution of $NaHSO_3$, and the DCM layer was washed with $Na_2CO_3$ (aq.), water and brine respectively, and concentrated to afford a residue, which was purified by flash chromatography on silica gel to give the title compound. MS (ESI) m/e (M+H$^+$): 324.0/222.0.

The following compounds were prepared in a similar manner to Reference Example 2 using the appropriate commercially available starting materials:

| Ref. Exp. # | Structure | Compound Name | MS observed [M + H]+ |
|---|---|---|---|
| Ref 3 | 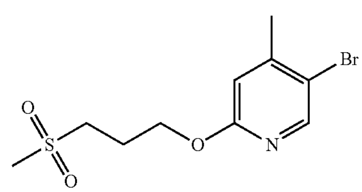 [SMILES: Cc1cc(OCCCS(C)(=O)=O)ncc1Br] | 5-bromo-4-methyl-2-(3-(methylsulfonyl)propoxy)pyridine | 308.0/310.0 |
| Ref 4 | 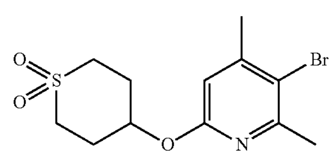 [SMILES: Cc1cc(OC2CCS(=O)(=O)CC2)nc(C)c1Br] | 3-Bromo-6-(1,1-dioxo-hexahydro-l16-thiopyran-4-yloxy)-2,4-dimethyl-pyridine | 334.2/336.2 |
| Ref 5 | 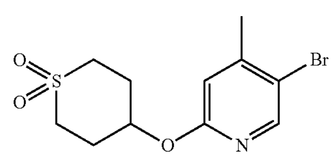 [SMILES: Cc1cc(OC2CCS(=O)(=O)CC2)ncc1Br] | 5-Bromo-2-(1,1-dioxo-hexahydro-l16-thiopyran-4-yloxy)-4-methyl-pyridine | 320.2/322.2 |
| Ref 6 | 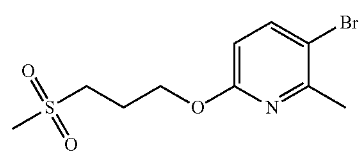 | 3-Bromo-6-(3-methanesulfonyl-propoxy)-2-methyl-pyridine | 308.0/310.0 |
| Ref 7 | 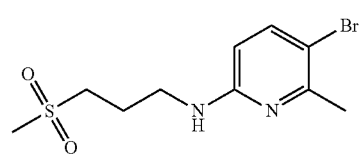 | (5-Bromo-6-methyl-pyridin-2-yl)-(3-methanesulfonyl-propyl)-amine | 307.0/309.0 |

| Ref. Exp. # | Structure | Compound Name | MS observed [M + H]+ |
|---|---|---|---|
| Ref 8 | 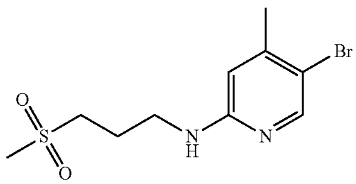 [SMILES: Cc1cc(NCCCS(C)(=O)=O)ncc1Br] | (5-Bromo-4-methyl-pyridin-2-yl)-(3-methanesulfonyl-propyl)-amine | 307.0/309.0 |
| Ref 9 | 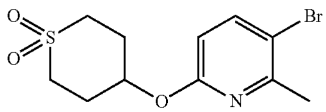 [SMILES: Cc1nc(OC2CCS(=O)(=O)CC2)ccc1Br] | 3-Bromo-6-(1,1-dioxo-hexahydro-1l6-thiopyran-4-yloxy)-2-methyl-pyridine | 320.0/322.0 |

Reference Example 10

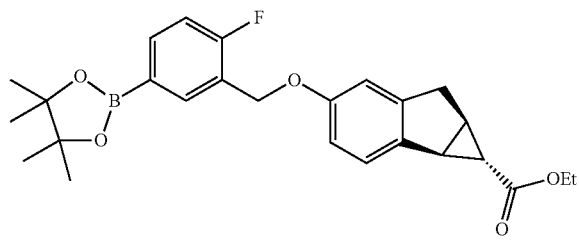 [SMILES: CCOC(=O)[C@H]1[C@@H]2Cc3cc(OCc4cc(B5OC(C)(C)C(C)(C)O5)ccc4F)ccc3[C@@H]21]

Step A. 5-Bromo-2-fluoro-phenyl-methanol

To a mixture of 5-bromo-2-fluoro-benzaldehyde (25 g, 125 mmol) in THF/MeOH (100 mL/20 mL) with ice-bath cooling was carefully added NaBH$_4$ (4.75 g, 125 mmol) portionwise and the resulting mixture was stirred at 0° C. for 2 hrs. The reaction mixture was added 50 mL of H$_2$O and partitioned with EA. The aqueous phase was extracted with ethyl acetate twice and the combined organic layer was washed with brine, dried over anhydrous Na$_2$SO$_4$ and concentrate. The residue was purified by short column chromatography on silica gel (PE/EA=8/1) to give the title compound.

Step B. 4-Bromo-2-bromomethyl-1-fluoro-benzene

To a cooled and stirred solution of compound 5-Bromo-2-fluoro-phenyl-methanol (20 g, 100 mmol) in anhydrous DCM (100 mL) was added PBr$_3$ (10.8 g, 40 mmol) dropwise at 0° C. and the resulting mixture was stirred at room temperature for 2 hrs. The reaction mixture was diluted with DCM and the organic phase was washed with water and brine, dried over anhydrous Na$_2$SO$_4$ and concentrate. The residue was purified by column chromatography on silica gel eluting with PE/EA=20/1~10/1 to give the title compound.

Step C. 4-(5-Bromo-2-fluoro-benzyloxy)-1,1a,6,6a-tetrahydro-cyclopropa[a]indene-1-carboxylic acid, ethyl ester To a mixture of (1S,1aS,6aR)-4-hydroxy-1,1a,6,6a-tetrahydrocyclopropa[a]indene-1-carboxylic acid, ethyl ester from Reference Example 1(2.2 g, 10 mmol) and anhydrous K$_2$CO$_3$ (1.6 g, 12 mmol) in DMF (20 mL) was added a solution of 4-Bromo-2-bromomethyl-1-fluoro-benzene (2.9 g, 11 mmol) in 2 mL of DMF dropwise at 0° C. and the resulting mixture was stirred at room temperature overnight. After the reaction was complete, the mixture was filtered off the insoluble part and the filtrate was diluted with EA. The organic layer was washed with water and brine, dried over anhydrous Na$_2$SO$_4$ and concentrated. The residue was purified by column chromatography on silica gel (EA/PE=10/1) to give the title compound.

Step D. 4-[2-Fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester A mixture of 4-(5-bromo-2-fluoro-benzyloxy)-1,1a,6,6a-tetrahydro-cyclopropa[a]indene-1-carboxylic acid, ethyl ester (8.1 g, 20 mmol), 4,4,5,5-tetramethyl-2-(4,4,5,5-tetramethyl-1,3,2-dioxaborolan-2-yl)-1,3,2-dioxaborolane (10.1 g, 40 mmol), potassium acetate (4.9 g, 50 mmol), Pd(dppf)Cl$_2$ (0.7 g, 1.0 mmol) in DMF (60 mL) was heated to 90° C. for 6 hrs under nitrogen atmosphere. After cooling to room temperature, the mixture was filtered off the insoluble part and the filtrate was diluted with EA. The organic layer was washed with water and brine, dried over anhydrous Na$_2$SO$_4$ and concentrate. The residue was purified by column chromatography on silica gel eluting with PE/EA=10/1~5/1 to give the title compound. MS (ESI) m/e (M+H$^+$): 453.1/455.1.

The following Reference Examples 11-12 were prepared in a similar manner to Reference Example 10 using the appropriate intermediates and commercially available starting materials.

| Ref. Ex. # | Structure | Compound Name | MS observed [M + 1]+ |
|---|---|---|---|
| Ref 11 | 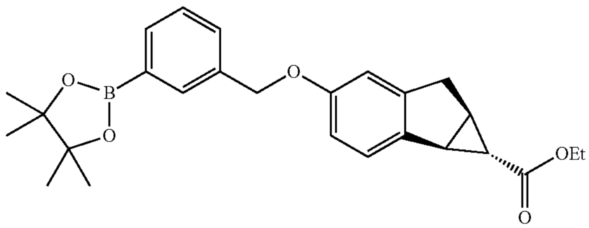 [SMILES: CCOC(=O)[C@H]1[C@@H]2Cc3cc(OCc4cccc(B5OC(C)(C)C(C)(C)O5)c4)ccc3[C@@H]21] | 4-[3-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester | 435.1 |
| Ref 12 | 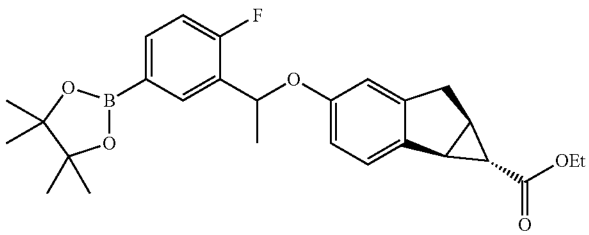 [SMILES: CCOC(=O)[C@H]1[C@@H]2Cc3cc(OC(C)c4cc(B5OC(C)(C)C(C)(C)O5)ccc4F)ccc3[C@@H]21] | 4-{1-[2-fluoro-5-(4,4,5,5-tetramethyl-[1,3,2]dioxaborolan-2-yl)-phenyl]-ethoxy}-1,1a,6,6a-tetrahydro-cyclopropa[a]indene-1-carboxylic acid, ethyl ester | 467.2 |

Reference Example 13

4-[2,6-Difluoro-3-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester

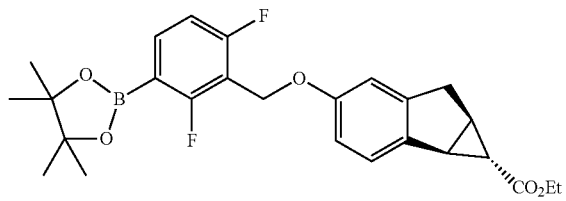 [SMILES: CCOC(=O)[C@H]1[C@@H]2Cc3cc(OCc4c(F)ccc(B5OC(C)(C)C(C)(C)O5)c4F)ccc3[C@@H]21]

Step A. 3-bromo-2,6-difluorobenzaldehyde

To a solution of diisopropylamine (5.56 g, 55 mmol) in dry THF (150 mL) was added solution of n-BuLi (2.5 M, 22 mL, 55 mmol) as dropwise at −55° C. under nitrogen atmosphere. The reaction mixture was stirred for 30 min at this temperature. Then a solution of 1-bromo-2,4-difluorobenzene (9.65 g, 50 mmol) was added dropwise. After stirring at −55° C. for 1 hour, dry DMF (7.3 g, 100 mmol) was added dropwise, and the resulting mixture was stirred at this temperature for 2 hrs. The reaction mixture was warmed to −20° C. slowly, and the reaction was quenched with water. The resulting mixture was neutralized by aqueous solution of HCl (2N) to pH=7. The organic layer was separated and collected, and the aqueous solution was extracted with ethyl acetate two times. The organic layerlayerlayerlayer was washed with brine, dried over Na$_2$SO$_4$ and concentrated to afford a residue, which was purified by silica gel chromatography on silica gel (PE/EA=10/1) to obtain the title compound.

Step B. (3-bromo-2,6-difluorophenyl)methanol

To a mixture of 3-bromo-2,6-difluorobenzaldehyde (10.5 g, 47.5 mmol) in MeOH (200 mL) with ice-bath cooling was added NaBH$_4$ (3.61 g, 95 mmol). The resulting mixture was stirred at 0° C. for 2 hrs. Added H$_2$O to quenched the reaction and the mixture was acidified by HCl (2N). The mixture was extracted with ethyl acetate for three times. The organic layers was washed with brine, dried over Na$_2$SO$_4$ and concentrated to afford a residue, which was purified by silica gel chromatography on silica gel (PE/EA=8/1) to obtain the title compound.

Step C. 4-(3-Bromo-2,6-difluoro-benzyloxy)-1,1a,6,6a-tetrahydro-cyclopropa[a]indene-1-carboxylic acid, ethyl ester Compound (3-bromo-2,6-difluorophenyl)methanol (9.86 g, 44.2 mmol), (1S,1aS,6aR)-4-hydroxy-1,1a,6,6a-tetrahydrocyclopropa[a]indene-1-carboxylic acid, ethyl ester from Reference Example 1 (9.65 g, 44.2 mmol) and triphenylphosphine (13.9 g, 53.1 mmol) were dissolved in dry DCM (150 mL) and cooled to 0° C. under N$_2$ for 20 min. The DIAD (10.72 g, 53.1 mmol) was added dropwise. The reaction solution was stirred 0° C. for 1 hr, and the mixture was warmed to 20° C. and stirring for 16 hrs. The reaction mixture was concentrated in vacuo to give a the crude product, which was purified by flash chromatography on silica gel (PE/EA=8/1) to afford the title compound. MS (ESI) m/e (M+H$^+$): 423.0/425.0

Step D. 4-[2,6-Difluoro-3-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester A mixture of 4-(3-bromo-2,6-difluoro-benzyloxy)-1,1a,6,6a-tetrahydro-cyclopropa[a]indene-1-carboxylic acid, ethyl ester (5.08 g, 12 mmol), 4,4,5,5-tetramethyl-2-(4,4,5,5-tetramethyl-1,3,2-dioxaborolan-2-yl)-1,3,2-dioxaborolane (3.36 g, 13.2 mmol), potassium acetate (2.60 g, 26.4 mmol), and Pd(dppf)Cl$_2$ (878 mg, 1.2 mmol) in dioxane (100 mL) was heated to 100° C. for 12 hrs under nitrogen atmosphere. After cooling to room temperature, the mixture was filtered to give off the insoluble part, and the filtrate was diluted with EA. The organic layer was washed with water, dried and concentrated in vacuo to give the crude product, which was purified by flash chromatography on silica gel (PE/EA=5/1) to yield the title compound. MS (ESI) m/e (M+H⁺): 471.2.

Reference Example 14

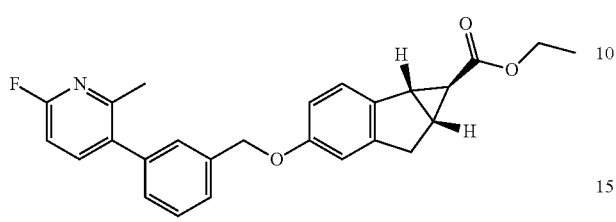

(1S,1aS,6aR)-ethyl 4-((3-(6-fluoro-2-methylpyridin-3-yl)benzyl)oxy)-1,1a,6,6a-tetrahydrocyclopropa[a]indene-1-carboxylate A mixture of (1S,1aS,6aR)-ethyl 4-((3-(4,4,5,5-tetramethyl-1,3,2-dioxaborolan-2-yl)benzyl)oxy)-1,1a,6,6a-tetrahydrocyclopropa[a]indene-1-carboxylate (1.8 g, 4.14 mmol), 3-bromo-6-fluoro-2-methylpyridine (0.95 g, 4.97 mmol), potassium carbonate (2.0 g, 14.5 mmol), and Tetrakis(triphenylphosphine)palladium(0) (479 mg, 0.414 mmol) in DME (20 mL) and water (10 ml) were degassed three times and heated to 90° C. for 2 hrs under nitrogen atmosphere. After cooling to room temperature, the reaction mixture was added 40 mL of H₂O and partitioned with EA (150 ml). The aqueous phase was extracted with ethyl acetate twice and the combined organic layer was washed with brine, dried over anhydrous Na₂SO₄ and concentrated in vacuo. The residue was purified by short column chromatography on silica gel 0%-50% hexane/EA to yield the title compound. MS (ESI) m/e (M+H⁺): 417.98.

Example 1

(1S,1aS,6aR)-4-[(2-fluoro-5-{2-methyl-6-[3-(methylsulfonyl)propoxy]pyridin-3-yl}benzyl)oxy]-1,1a,6,6a-tetrahydrocyclopropa[a]indene-1-carboxylic acid

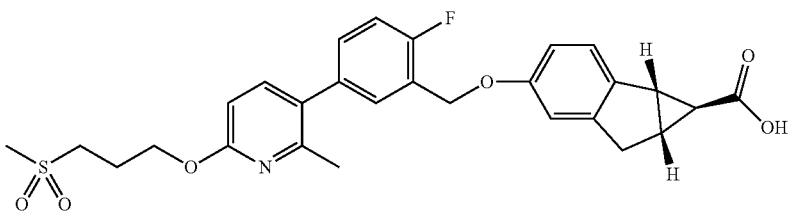 [SMILES: Cc1nc(OCCCS(C)(=O)=O)ccc1-c1ccc(F)c(COc2ccc3c(c2)C[C@H]2[C@H](C(=O)O)[C@@H]32)c1]

Step A. (1S,1aS,6aR)-4-[(5-bromo-2-fluorobenzyl)oxy]-1,1a,6,6a-tetrahydrocyclopropa[a]indene-1-carboxylic acid, ethyl ester To a solution of (1S,1aS,6aR)-4-hydroxy-1,1a,6,6a-tetrahydrocyclopropa[a]indene-1-carboxylic acid, ethyl ester from Reference Example 1 (2.5 g, 11.45 mmol) and 4-bromo-2-(bromomethyl)-1-fluorobenzene (3.1 g, 11.45 mmol) in DMF (50 ml) was added potassium carbonate (3.2 g, 22.91 mmol). The reaction mixture was stirred at room temperature overnight. The mixture was diluted with ethyl acetate (300 ml), washed with aqueous sodium hydrogen carbonate (saturated, 3×100 mL) and brine, dried (Na₂SO₄), filtered and the solvent was evaporated under reduced pressure. The residue was purified by column chromatography on silica gel BIOTAGE (Uppsala, Sweden) 40M, eluting with EtOAc/isohexane 0-50% to afford the title compound. LC/MS: m/e 407.0 (M+H).

Step B. (1S,1aS,6aR)-4-{[2-fluoro-5-(6-fluoro-2-methylpyridin-3-yl)benzyl]oxy}-1,1a,6,6a-tetrahydrocyclopropa[a]indene-1-carboxylic acid, ethyl ester To a solution of (1S,1aS,6aR)-4-[(5-bromo-2-fluorobenzyl)oxy]-1,1a,6,6a-tetrahydrocyclopropa[a]indene-1-carboxylic acid, ethyl ester (4.5 g, 11.1 mmol) in THF (33 ml) and water (11 ml) was added 6-fluoro-2-methyl-3-(4,4,5,5-tetramethyl-1,3,2-dioxaborolan-2-yl)pyridinepyridinepyridinepyridine (3.16 g, 13.3 mmol), potassium phosphate tribasic (4.71 g, 22.1 mmol), palladium (II) acetate (0.25 g, 1.11 mmol) and 2-dicyclohexylphosphino-2',6'-dimethoxybiphenyl (0.68 g, 1.67 mmol). The mixture was degassed three times and heated to 70° C. for two hours. The mixture was cooled, diluted with ethyl acetate (300 ml), washed with aqueous sodium hydrogen carbonate (saturated, 3×100 mL) and brine, dried (Na₂SO₄), filtered and the solvent was evaporated under reduced pressure. The residue was purified by column chromatography on silica gel BIOTAGE (Uppsala, Sweden) 40M, eluting with EtOAc/isohexane 0-50% to afford the title compound. LC/MS: m/e 436.1 (M+H).

Step C. (1S,1aS,6aR)-4-[(2-fluoro-5-{2-methyl-6-[3-(methylsulfonyl)propoxy]pyridin-3-yl}benzyl)oxy]-1,1a,6,6a-tetrahydrocyclopropa[a]indene-1-carboxylic acid To a solution of 3-(methylsulfonyl)propan-1-ol (63.5 mg, 0.46 mmol) in DMF (2 ml) at 0° C. was added sodium hydride (60%, 23.0 mg, 0.574 mmol). The reaction mixture was stirred at 0° C. for approximately 30 mins. (1S,1aS,6aR)-4-{[2-fluoro-5-(6-fluoro-2-methylpyridin-3-yl)benzyl]oxy}-1,1a,6,6a-tetrahydrocyclopropa[a]indene-1-carboxylic acid, ethyl ester (100 mg, 0.23 mmol) was added to the reaction. The mixture was stirred at room temperature overnight. 1 ml of LiOH (1M) was added to the reaction and irradiated with microwaves at 100° C. for 1 hour. The pH of the mixture was adjusted to 7.0 with 1 N HCl. The residue was purified by preparative HPLC reverse phase (C-8), eluting with acetonitrile/water with 0.1% of TFA to give the title compound. LC/MS: m/e 526.2 (M+H).

Example 2

(1S,1aS,6aR)-4-[(5-{6-[(1,1-dioxidotetrahydro-2H-thiopyran-4-yl)oxy]-2-methylpyridin-3-yl}-2-fluorobenzyl]oxy}-1,1a,6,6a-tetrahydrocyclopropa[a]indene-1-carboxylic acid

Step A. (1S,1aS,6aR)-4-({2-fluoro-5-[2-methyl-6-(tetrahydro-2H-thiopyran-4-yloxy)pyridin-3-yl]benzyl}oxy)-1,1a,6,6a-tetrahydrocyclopropa[a]indene-1-carboxylic acid To a solution of tetrahydro-2H-thiopyran-4-ol (56.6 mg, 0.48 mmol) in DMF (2 ml) at 0° C. was added sodium hydride (60%, 19.2 mg, 0.48 mmol). The reaction mixture was stirred at 0° C. for approximately 30 mins. (1S,1aS,6aR)-4-{[2-fluoro-5-(6-fluoro-2-methylpyridin-3-yl)benzyl]oxy}-1,1a,6,6a-tetrahydrocyclopropa[a]indene-1-carboxylic acid, ethyl ester from Example 1, Step B (100 mg, 0.24 mmol) was added to the reaction. The mixture was stirred at room temperature overnight. 1 ml of LiOH (1M) was added to the reaction and irradiated microwaves at 100° C. for 1 hour. The pH of the mixture was adjusted to 7.0 with 1 N HCl. The residue was purified by preparative HPLC reverse phase (C-8), eluting with Acetonitrile/Water with 0.1% of TFA to give the title compound. MS: m/e 488.1 (M+H).

Step B. (1S,1aS,6aR)-4-[(5-{6-[(1,1-dioxidotetrahydro-2H-thiopyran-4-yl)oxy]-2-methylpyridin-3-yl)-2-fluorobenzyl]oxy)-1,1a,6,6a-tetrahydrocyclopropa[a]indene-1-carboxylic acid A solution of (1S,1aS,6aR)-4-({2-fluoro-5-[2-methyl-6-(tetrahydro-2H-thiopyran-4-yloxy)pyridin-3-yl]benzyl}oxy)-1,1a,6,6a-tetrahydrocyclopropa[a]indene-1-carboxylic acid (98 mg, 0.20 mmol) in $CH_2Cl_2$ (2 ml) was added mCPBA (69 mg, 0.2 mmol) at 0° C. The reaction was stirred at room temperature for 30 mins. The residue was purified by preparative HPLC reverse phase (C-8), eluting with Acetonitrile/Water with 0.1% of TFA to give the title compound. MS: m/e 538.2 (M+H).

Example 3

(1S,1aS,6aR)-4-((3-(2-Methyl-6-(4-(methylsulfonyl)piperidin-1-yl)pyridin-3-yl)benzyl)oxy)-1,1a,6,6a-tetrahydrocyclopropa[a]indene-1-carboxylic acid

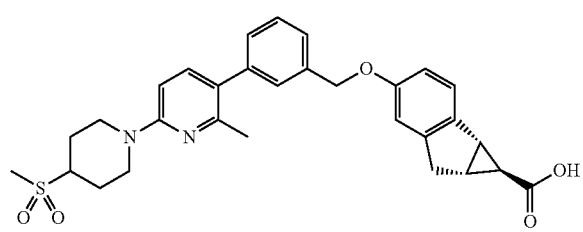 [SMILES: Cc1nc(N2CCC(S(C)(=O)=O)CC2)ccc1-c1cccc(COc2ccc3c(c2)C[C@H]2[C@H](C(=O)O)[C@@H]32)c1]

A solution of (1S,1aS,6aR)-ethyl 4-((3-(6-fluoro-2-methylpyridin-3-yl)benzyl)oxy)-1,1a,6,6a-tetrahydrocyclopropa[a]indene-1-carboxylate from Reference Example 14 (20 mg, 0.05 mmol) in dimethyl acetamide (0.5 mL) was added to a reaction vial containing 4-(methylsulfonyl)piperidin-1-ium chloride (30 mg, 0.15 mmol). Potassium carbonate (33 mg, 0.24 mmol) was added and the reaction mixture was heated at 130° C. for approximately 18 hours. Triethylamine (0.033 mL, 0.24 mmol) was added and the reaction mixture heated to 150° C. for two hours. After cooling to room temperature, tetrahydrofuran (0.5 mL), methanol (0.3 mL) and aqueous lithium hydroxide (2 N, 0.2 mL) were added and the resulting mixture was heated to 60° C. for two hours. After cooling to room temperature, the reaction mixture was partitioned between ethyl acetate (1.7 mL) and aqueous hydrochloric acid (2 N, 0.5 mL). The organic fraction was separated then concentrated in vacuo. The residue was dissolved in dimethyl sulfoxide (0.7 mL), filtered (0.45 μm ACRODISC filter), and the filtrate purified by reverse phase mass-directed HPLC to give the title compound as a formate salt. LCMS: 533.19 (M+1), 0.75 min.

Column: Waters ACQUITY ULTRA PERFORMANCE LC BEH C18, 2.1×50 mm, 1.7 um. Flow: 1 ml/min. Gradient: 5%-100% acetonitrile in 1.4 mins. Column Temp: 55 C. Mobile Phase: A: 0.1% $NH_4OH$ in HPLC grade Water; B: HPLC grade acetonitrile. LCMS conditions. Samples were analyzed by LCMS (Waters XTERRA C18, 3.5 μm, 2.1×20 mm, 1.5 mL/min, acetonitrile/water 10:90 to 98:2 in 3.25 min).

Example 4

(1S,1aS,6aR)-4-[(3-{2,4-dimethyl-6-[3-(methylsulfonyl)propoxy]pyridin-3-yl}benzyl)oxy]-1,1a,6,6a-tetrahydrocyclopropa[a]indene-1-carboxylic acid

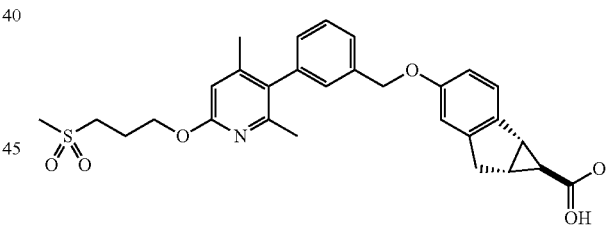

Method A

Step A. (1S,1aS,6aR)-4-[(3-bromobenzyl)oxy]-1,1a,6,6a-tetrahydrocyclopropa[a]indene-1-carboxylic acid, ethyl ester (1S,1aS,6aR)-4-Hydroxy-1,1a,6,6a-tetrahydrocyclopropa[a]indene-1-carboxylic acid, ethyl ester from Example 1, Step B (3.44 g, 13.75 mmol) and potassium carbonate (3.80 g, 27.5 mmol) were placed in a 250 ml RBF, DMF (27.5 ml) added and the slurry stirred at RT. 1-bromo-3-(bromomethyl)benzene (3.44 g, 13.75 mmol) was added dropwise and the mixture stirred at 60 C for 3 hours. The mixture was diluted with water (500 ml), extracted with EtOAc (3×150 ml), the organics combined, washed with brine, dried over sodium sulfate, filtered and the volatiles removed in vacuo. The reside was purified by column chromatography on silica gel using a BIOTAGE (Uppsala, Sweden) KP cartridge (50 g) using a gradient eluant of 0-30% EtOAc:hexanes to afford the title compound. MS (m/z): 387 (M+H)⁺.

Step B. (1S,1aS,6aR)-4-[(3-Bromobenzyl)oxy]-1,1a, 6,6a-tetrahydrocyclopropa[a]indene-1-carboxylic acid (1S,1aS,6aR)-4-[(3-bromobenzyl)oxy]-1,1a,6,6a-tetrahydrocyclopropa[a]indene-1-carboxylic acid, ethyl ester (4.6 g, 11.88 mmol) was dissolved in THF (16 ml), and ethanol (16 ml) was added. A solution of lithium hydroxide (2.492 g, 59.4 mmol, aq) was added and the mixture stirred at RT overnight. The mixture was diluted with water (100 ml), acetic acid (3 ml) and EtOAc (100 ml). The mixture was shaken and the layers separated. The aqueous phase was extracted with EtOAc (2×50 ml). The organics fractions were combined, washed with brine, dried over sodium sulfate, filtered and the volatiles removed in vacuo to afford the title compound. MS (m/z): 359 (M+H)⁺.

Step C. (1S,1aS,6aR)-4-{[3-(4,4,5,5-tetramethyl-1,3, 2-dioxaborolan-2-yl)benzyl]oxy}-1,1a,6,6a-tetrahydrocyclopropa[a]indene-1-carboxylic acid (1S,1aS,6aR)-4-[(3-Bromobenzyl)oxy]-1,1a,6,6a-tetrahydrocyclopropa[a]indene-1-carboxylic acid (1 g, 2.78 mmol)), bis(pinacolato)diboron (1.414 g, 5.57 mmol), potassium acetate (0.820 g, 8.35 mmol), and 1,1'-bis(diphenylphosphino)ferrocene-palladium(II)dichloride dichloromethane complex (0.227 g, 0.278 mmol), were combined in a 50 ml RBF. The vial was sealed and degassed (3×) with nitrogen. Dioxane (6.96 ml, sparged with nitrogen) was added and the mixture degassed (3×). The mixture was heated in a microwave at 100 C for 15 min. The mixture was diluted with 1:1:1 brine:water:saturated sodium bicarbonate (30 ml) and extracted with EtOAc (3×30 ml). The organic fractions were combined, washed with brine, dried over sodium sulfate, filtered, and the volatiles removed in vacuo. The crude oil was purified by column chromatagraphy on silica gel, BIOTAGE (Uppsala, Sweden) KP 25 g), using a gradient eluant of 0-20% acetone:DCM+1% acetic acid to afford the title compound. MS (m/z): 407 (M+H)⁺.

Step D. 3-iodo-2,4-dimethyl-6-[3-(methylsulfonyl) propoxy]pyridine 3-(Methylsulfonyl)propan-1-ol (102 mg, 0.737 mmol) was dissolved in DMF (1.0 ml) and sodium hydride (44.2 mg, 1.106 mmol) was added at RT. The mixture was stirred for 10 minutes. The mixture was cooled to 0° C. and a solution of 6-bromo-3-iodo-2,4-dimethylpyridine (230 mg, 0.737 mmol) in DMF (0.5 ml) was added dropwise. The mixture was stirred for 10 minutes, the bath removed and the mixture warmed to RT over 1 hour. The mixture was diluted with saturated ammonium chloride (1 ml, aq), further diluted with 4:1 water:saturated sodium bicarbonate (50 ml), and the mixture extracted with EtOAc (3×40 ml). The organic fractions were combined, washed with brine, dried over sodium sulfate, filtered and the volatiles removed in vacuo. The crude oil was purified by column chromatagraphy on silica gel (Biotage HP 25 g) using a gradient eluant of 5-100% EtOAc:Hexanes to afford the title compound. MS (m/z): 370 (M+H)⁺.

Step E. (1S,1aS,6aR)-4-[(3-{2,4-dimethyl-6-[3-(methylsulfonyl)propoxy]pyridin-3-yl}benzyl)oxy]-1,1a,6,6a-tetrahydrocyclopropa[a]indene-1-carboxylic acid (1S,1aS,6aR)-4-{[3-(4,4,5,5-tetramethyl-1,3,2-dioxaborolan-2-yl)benzyl]oxy}-1,1a,6,6a-tetrahydrocyclopropa[a]indene-1-carboxylic acid (77 mg, 0.190 mmol), 3-iodo-2,4-dimethyl-6-[3-(methylsulfonyl)propoxy]pyridine (50 mg, 0.135 mmol), palladium acetate (1.216 mg, 5.42 μmol), 2-dicyclohexylphosphino-2',6'-dimethoxybiphenyl (3.34 mg, 8.13 μmol)), and potassium phosphate, dibasic (70.8 mg, 0.406 mmol) were combined in a 1.5 ml microwave vial. The vial was sealed, degassed (3×) with nitrogen, and 3:1 dioxane:water (677 μl, sparged with nitrogen) was added. The mixture was shaken then heated at 75° C. for 3 hrs. The mixture was diluted with 1:1 brine:water:(30 ml), acidified with acetic acid and extracted with ethyl acetate (3×30 ml). The combined organic fractions were washed with brine, dried over sodium sulfate, filtered, and the volatiles removed in vacuo. The crude oil was purified by column chromatography on silica gel, BIOTAGE (Uppsala, Sweden) HP 10 g, using a gradient eluant of 5-80% EtOAc: Hexanes to afford the title compound. MS (m/z): 522 (M+H)⁺.

Method B

Step A. (3-(2,4-dimethyl-6-(3-(methylsulfonyl) propoxy)pyridin-3-yl)phenyl)methanol A mixture of 3-bromo-2,4-dimethyl-6-(3-(methylsulfonyl)propoxy)pyridine from Reference Example 2 (193 mg, 0.6 mmol), 3-(hydroxymethyl)phenylboronic acid (137 mg, 0.9 mmol), $K_3PO_4$ (468 mg, 1.8 mmol), $Pd_2(dba)_3$ (55 mg, 0.06 mmol), and s-phos (49 mg, 0.12 mmol) in a co-solvent of THF (6 mL)/$H_2O$ (1.5 mL) was heated at 100° C. for 3 hrs under nitrogen atmosphere. After cooling to room temperature, the mixture was filtered to remove the insoluble part. The filtrate was partitioned by ethyl acetate and water, and the ethyl acetate layer was washed with brine, dried and concentrated in vacuo to obtain the crude product, which was purified by flash chromatography on silica gel to afford the title compound. MS (ESI) m/e (M+H⁺): 350.1.

Step B. 4-{3-[6-(3-Methanesulfonyl-propoxy)-2,4-dimethyl-pyridin-3-yl]-benzyloxy}-1,1a,6,6a-tetrahydro-cyclopropa[a]indene-1-carboxylic acid, ethyl ester To a stirred and cooled solution of (3-(2,4-dimethyl-6-(3-(methylsulfonyl)propoxy)pyridin-3-yl)phenyl)methanol (126 mg, 0.36 mmol), (1S,1aS,6aR)-4-hydroxy-1,1a,6,6a-tetrahydrocyclopropa[a]indene-1-carboxylic acid, ethyl ester from Reference Example 1 (75 mg, 0.36 mmol) and triphenylphosphine (114 mg, 0.43 mmol) in dry DCM (5 mL) under $N_2$ was added DIAD (88 mg, 0.43 mmol) as one portion. The reaction solution was stirred 0° C. for 1 h and the mixture was warmed to 20° C. for 16 hrs. The mixture was concentrated directly to give the crude product, which was purified by flash chromatography to afford the title compound. MS m/e (M+H⁺): 550.2

Step C. 4-{3-[6-(3-Methanesulfonyl-propoxy)-2,4-dimethyl-pyridin-3-yl]-benzyloxy}-1,1a,6,6a-tetrahydro-cyclopropa[a]indene-1-carboxylic acid To a mixture of 4-{3-[6-(3-methanesulfonyl-propoxy)-2,4-dimethyl-pyridin-3-yl]-benzyloxy}-1,1a,6,6a-tetrahydro-cyclopropa[a]indene-1-carboxylic acid, ethyl ester (84 mg, 0.15 mmol) in a co-solvent THF (2 mL), MeOH (2 mL) and $H_2O$ (1 mL) was added NaOH (100 mg, 2.5 mmol) stirred at room temperature for 2 hrs. The resulting mixture was acidified by HCl (2 N) to pH=2, and extracted with ethyl acetate (2×10 mL). The combined organic layer was washed with water, brine, dried over Na₂SO₄ and concentrated in vacuo to afford the crude product, which was purified by prep-HPLC to give the title compound. MS m/e (M+H⁺): 522.2; ¹H-NMR (CDCl₃ 400 MHz): δ 7.38-7.31 (m, 2H), 7.17 (t, J=8.4 Hz, 1H), 7.09 (s, 1H), 7.00 (d, J=7.2 Hz, 1H), 6.72 (s, 1H), 6.78 (m, 1H), 6.40 (s, 1H), 4.99 (s, 2H), 4.37 (t, J=6.0 Hz, 2H), 3.20-3.15 (m, 3H), 2.94 (m, 1H), 2.89 (s, 3H), 2.43-2.39 (m, 1H), 2.30-2.23 (m, 2H), 2.06 (s, 3H), 1.89 (s, 3H), 1.10 (m, 1H).

The following compounds were prepared in a similar manner to Example 4, Method B from the corresponding bromide intermediates in Reference Examples 3-9:

| Ex. No. | Structure | Compound Name | MS observed [M + H]+ |
|---|---|---|---|
| 5 | 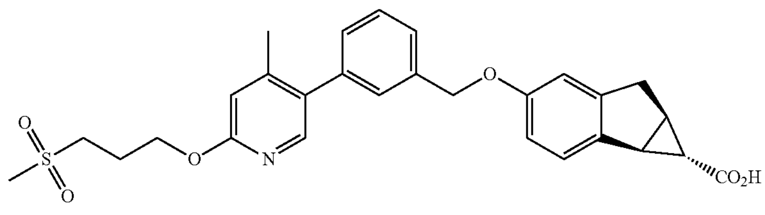 [SMILES: Cc1cc(OCCCS(C)(=O)=O)ncc1-c1cccc(COc2ccc3c(c2)C[C@H]2[C@H](C(=O)O)[C@@H]32)c1] | 4-{2-[6-(3-Methanesulfonyl-propoxy)-4-methyl-pyridin-3-yl]-benzyloxy}-1,1a,6,6a-tetrahydro-cyclopropa[a]indene-1-carboxylic acid | 508.2 |
| 6 | 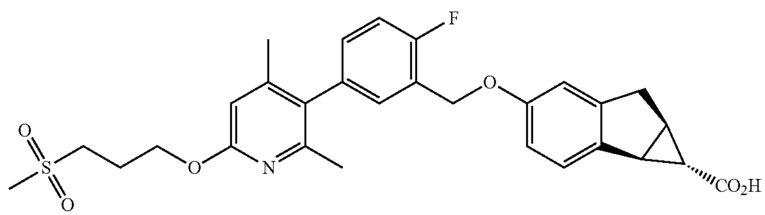 [SMILES: Cc1cc(OCCCS(C)(=O)=O)nc(C)c1-c1ccc(F)c(COc2ccc3c(c2)C[C@H]2[C@H](C(=O)O)[C@@H]32)c1] | 4-{2-Fluoro-5-[6-(3-methanesulfonyl-propoxy)-2,4-dimethyl-pyridin-3-yl]-benzyloxy}-1,1a,6,6a-tetrahydro-cyclopropa[a]indene-1-carboxylic acid | 540.2 |
| 7 | 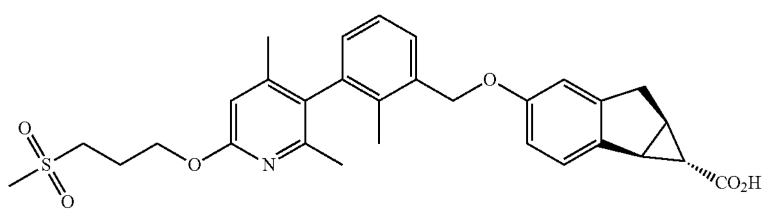 [SMILES: Cc1cc(OCCCS(C)(=O)=O)nc(C)c1-c1cccc(COc2ccc3c(c2)C[C@H]2[C@H](C(=O)O)[C@@H]32)c1C] | 4-{3-[6-(3-Methane-sulfonyl-propoxy)-2,4-dimethyl-pyridin-3-yl]-2-methyl-benzyloxy}-1,1a,6,6a-tetrahydro-cyclopropa[a]indene-1-carboxylic acid | 536.2 |
| 8 | 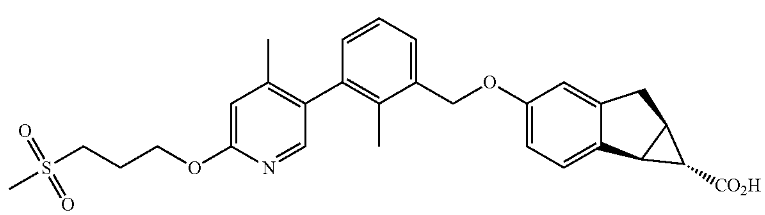 [SMILES: Cc1cc(OCCCS(C)(=O)=O)ncc1-c1cccc(COc2ccc3c(c2)C[C@H]2[C@H](C(=O)O)[C@@H]32)c1C] | 4-{3-[6-(3-Methanesulfonyl-propoxy)-4-methyl-pyridin-3-yl]-2-methyl-benzyloxy}-1,1a,6,6a-tetrahydro-cyclopropa[a]indene-1-carboxylic acid | 522.2 |
| 9 | 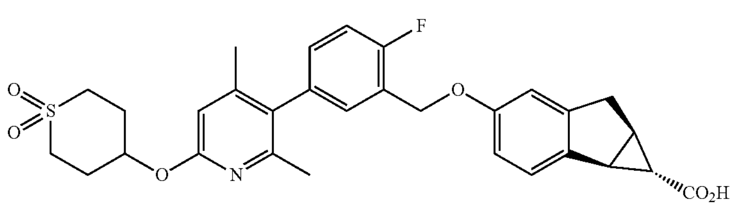 [SMILES: Cc1cc(OC2CCS(=O)(=O)CC2)nc(C)c1-c1ccc(F)c(COc2ccc3c(c2)C[C@H]2[C@H](C(=O)O)[C@@H]32)c1] | 4-{5-[6-(1,1-Dioxo-hexahydro-l16-thiopyran-4-yloxy)-2,4-dimethyl-pyridin-3-yl]-2-fluoro-benzyloxy}-1,1a,6,6a-tetrahydro-cyclopropa[a]indene-1-carboxylic acid | 552.2 |
| 10 | 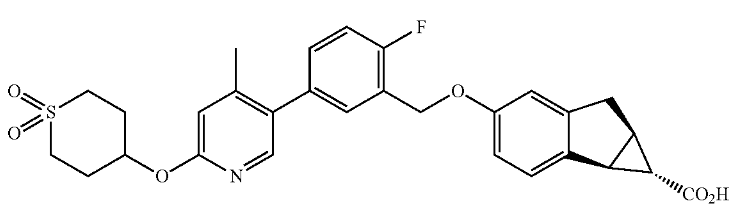 [SMILES: Cc1cc(OC2CCS(=O)(=O)CC2)ncc1-c1ccc(F)c(COc2ccc3c(c2)C[C@H]2[C@H](C(=O)O)[C@@H]32)c1] | 4-{5-[6-(1,1-Dioxo-hexahydro-l16-thiopyran-4-yloxy)-4-methyl-pyridin-3-yl]-2-fluoro-benzyloxy}-1,1a,6,6a-tetrahydro-cyclopropa[a]indene-1-carboxylic acid | 538.2 |

| Ex. No. | Structure | Compound Name | MS observed [M + H]+ |
|---|---|---|---|
| 11 | 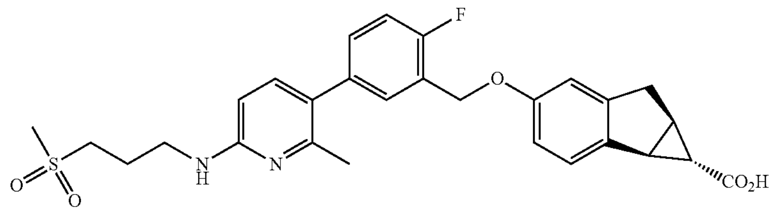 [SMILES: Cc1nc(NCCCS(C)(=O)=O)ccc1-c1ccc(F)c(COc2ccc3c(c2)C[C@H]2[C@H](C(=O)O)[C@@H]32)c1] | 4-{2-Fluoro-5-[6-(3-methanesulfonyl-propylamino)-2-methyl-pyridin-3-yl]-benzyloxy}-1,1a,6,6a-tetrahydro-cyclopropa[a]indene-1-carboxylic acid | 525.2 |
| 12 | 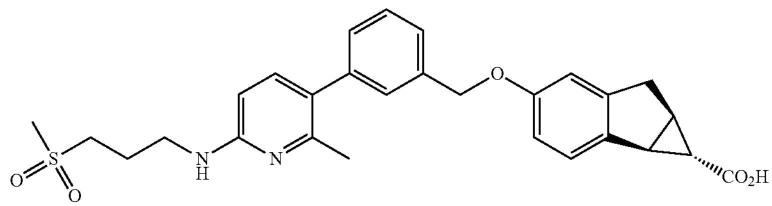 [SMILES: Cc1nc(NCCCS(C)(=O)=O)ccc1-c1cccc(COc2ccc3c(c2)C[C@H]2[C@H](C(=O)O)[C@@H]32)c1] | 4-{3-[6-(3-Methanesulfonyl-propylamino)-2-methyl-pyridin-3-yl]-benzyloxy}-1,1a,6,6a-tetrahydro-cyclopropa[a]indene-1-carboxylic acid | 507.2 |
| 13 | 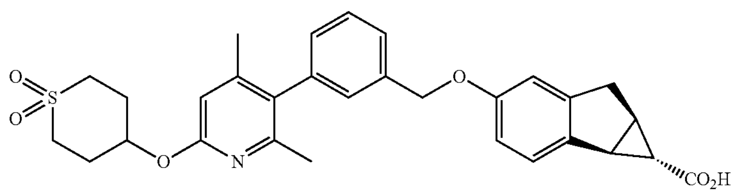 [SMILES: Cc1cc(OC2CCS(=O)(=O)CC2)nc(C)c1-c1cccc(COc2ccc3c(c2)C[C@H]2[C@H](C(=O)O)[C@@H]32)c1] | 4-{3-[6-(1,1-Dioxo-hexahydro-l16-thiopyran-4-yloxy)-2,4-dimethyl-pyridin-3-yl]-benzyloxy}-1,1a,6,6a-tetrahydro-cyclopropa[a]indene-1-carboxylic acid | 534.2 |
| 14 | 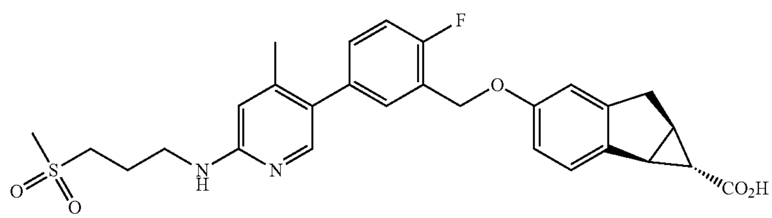 [SMILES: Cc1cc(NCCCS(C)(=O)=O)ncc1-c1ccc(F)c(COc2ccc3c(c2)C[C@H]2[C@H](C(=O)O)[C@@H]32)c1] | 4-{2-Fluoro-5-[6-(3-methanesulfonyl-propylamino)-4-methyl-pyridin-3-yl]-benzyloxy}-1,1a,6,6a-tetrahydro-cyclopropa[a]indene-1-carboxylic acid | 525.2 |
| 15 | 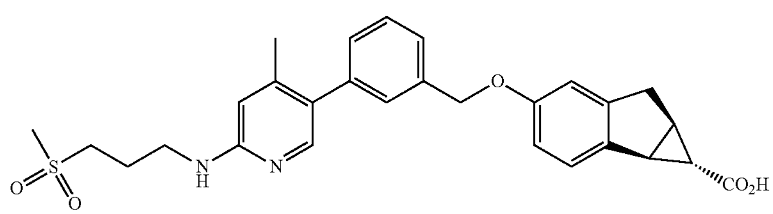 [SMILES: Cc1cc(NCCCS(C)(=O)=O)ncc1-c1cccc(COc2ccc3c(c2)C[C@H]2[C@H](C(=O)O)[C@@H]32)c1] | 4-{3-[6-(3-Methanesulfonyl-propylamino)-4-methyl-pyridin-3-yl]-benzyloxy}-1,1a,6,6a-tetrahydro-cyclopropa[a]indene-1-carboxylic acid | 507.2 |
| 16 | 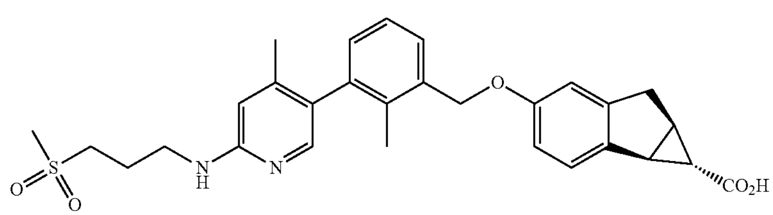 [SMILES: Cc1cc(NCCCS(C)(=O)=O)ncc1-c1cccc(COc2ccc3c(c2)C[C@H]2[C@H](C(=O)O)[C@@H]32)c1C] | 4-{3-[6-(3-Methanesulfonyl-propylamino)-4-methyl-pyridin-3-yl]-2-methyl-benzyloxy}-1,1a,6,6a-tetrahydro-cyclopropa[a]indene-1-carboxylic acid | 521.2 |
| 17 | 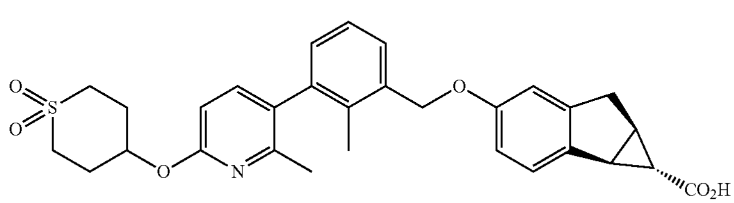 [SMILES: Cc1nc(OC2CCS(=O)(=O)CC2)ccc1-c1cccc(COc2ccc3c(c2)C[C@H]2[C@H](C(=O)O)[C@@H]32)c1C] | 4-{3-[6-(1,1-Dioxo-hexahydro-l16-thiopyran-4-yloxy)-2-methyl-pyridin-3-yl]-2-methyl-benzyloxy}-1,1a,6,6a-tetrahydro-cyclopropa[a]indene-1-carboxylic acid | 534.2 |

| Ex. No. | Structure | Compound Name | MS observed [M + H]+ |
|---|---|---|---|
| 18 | 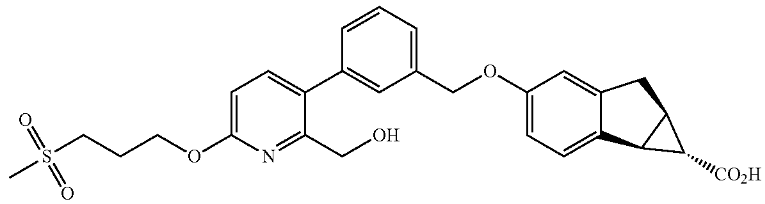 [SMILES: CS(=O)(=O)CCCOc1ccc(-c2cccc(COc3ccc4c(c3)C[C@H]3[C@H](C(=O)O)[C@@H]43)c2)c(CO)n1] | 4-{3-[2-Hydroxymethyl-6-(3-methanesulfonyl-propoxy)-pyridin-3-yl]-benzyloxy}-1,1a,6,6a-tetrahydro-cyclopropa[a]indene-1-carboxylic acid | 524.2 |

Example 19

(1S,1aS,6aR)-4-[(2-fluoro-5-{4-methyl-6-[3-(methylsulfonyl)propoxy]pyridin-3-yl}benzyl)oxy]-1,1a,6,6a-tetrahydrocyclopropa[a]indene-1-carboxylic acid

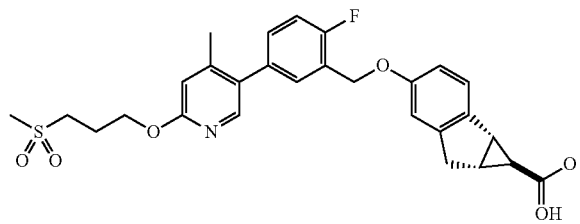 [SMILES: Cc1cc(OCCCS(C)(=O)=O)ncc1-c1ccc(F)c(COc2ccc3c(c2)C[C@H]2[C@H](C(=O)O)[C@@H]32)c1]

Step A. (1S,1aS,6aR)-4-[(5-bromo-2-fluorobenzyl)oxy]-1,1a,6,6a-tetrahydro-cyclopropa[a]indene-1-carboxylic acid, ethyl ester (1S,1aS,6aR)-4-hydroxy-1,1a,6,6a-tetrahydrocyclopropa[a]indene-1-carboxylic acid, ethyl ester, from reference Example 1 (2.0 g, 9.2 mmol), (5-bromo-2-fluorophenyl)methanol (2.7 g, 10.1 mmol), and triphenyphosphine (2.9 g, 11.0 mmol), were dissolved in toluene (30 ml). Diisopropyl azodicarboxylate (DIAD) (2.2 g, 11.0 mmol) was added and the mixture stirred at RT overnight. The mixture was diluted with EtOAc (150 ml), washed with water, and brine. The organic fraction was dried over sodium sulfate, filtered and the volatiles removed in vacuo. The reside was purified by column chromatography on silica gel using a BIOTAGE (Uppsala, Sweden) KP cartridge (50 g) using a gradient eluant of 0-100% EtOAc:hexanes to afford the title compound. MS (m/z): 446 (M+CH$_3$CN)$^+$.

Step B. (1S,1aS,6aR)-4-{[2-fluoro-5-(4,4,5,5-tetramethyl-1,3,2-dioxaborolan-2-yl)benzyl]oxy}-1,1a,6,6a-tetrahydrocyclopropa[a]indene-1-carboxylic acid, ethyl ester (1S,1aS,6aR)-4-[(5-bromo-2-fluorobenzyl)oxy]-1,1a,6,6a-tetrahydrocyclopropa[a]indene-1-carboxylic acid, ethyl ester (1.5 g, 3.7 mmol)), bis (pinacolato)diboron (1.4 g, 5.5 mmol), potassium acetate (1.1 g, 11.1 mmol), and 1,1'-bis(diphenylphosphino)ferrocene-palladium(II)dichloride dichloromethane complex (0.30 g, 0.37 mmol), were combined in a 50 ml RBF. The vial was sealed degassed (3×) with nitrogen, dioxane (15 ml, sparged with nitrogen) added and mixture degassed (3×). The mixture was heated at 100° C. for 14 hours. The mixture was diluted with 1:1:1 brine:water:saturated sodium bicarbonate (100 ml) and extracted with EtOAc (3×100 ml). The organic fractions were combined, washed with brine, dried over sodium sulfate, filtered, and the volatiles removed in vacuo. The crude oil was purified by column chromatagraphy on silica gel, BIOTAGE (Uppsala, Sweden) KP 25 g, using a gradient eluant of 0-40% EtOAc:hexanes to the title compound. MS (m/z): 453 (M+H)$^+$.

Step C. 3-(Methylsulfonyl)propyl 4-methylbenzenesulfonate 3-(Methylsulfonyl)propan-1-ol (102 mg, 0.737 mmol), DMAP (0.88 g, 7.2 mmol), and TEA (6.1 ml, 43.4 mmol) were dissolved in THF (29.0 ml). Tosyl chloride (6.1 g, 31.8 mmol) was added and the mixture heated at 50° C. for 14 hours. The mixture was cooled to RT, diluted with water (300 ml), and extracted with EtOAc (3×150 ml). The organic fractions were combined, washed with brine, dried over magnesium sulfate, filtered and the volatiles removed in vacuo. The crude product was purified by column chromatagraphy on silica gel, BIOTAGE (Uppsala, Sweden) HP 340 g, using a gradient eluant of 5-100% EtOAc:Hexanes to the title compound. MS Ret: (m/z): 293 (M+H)$^+$.

Step D. 5-Bromo-4-methyl-2-[3-(methylsulfonyl)propoxy]pyridine 3-(Methylsulfonyl)propyl 4-methylbenzenesulfonate (1.1 g, 3.7 mmol) was dissolved in DMF (5.0 ml). TEA (0.52 ml, 3.7 mmol) and 5-bromo-4-methylpyridin-2-ol (0.52 ml, 3.7 mmol) were added and the mixture stirred at RT for 14 hours. The mixture was diluted with EtOAc (100 ml), washed with water (3×50 ml), brine, dried over magnesium sulfate, filtered and the volatiles removed in vacuo. The crude oil was purified by column chromatagraphy on silica gel, BIOTAGE (Uppsala, Sweden) HP 25 g, using a gradient eluant of 5-100% EtOAc:Hexanes to afford the title compound. MS (m/z): 325 (M+H$_2$O))$^+$.

Step E. (1S,1aS,6aR)-4-[(2-fluoro-5-{4-methyl-6-[3-(methylsulfonyl)propoxy]pyridin-3-yl}benzyl)oxy]-1,1a,6,6a-tetrahydrocyclopropa[a]indene-1-carboxylic acid Ethyl (1S,1aS,6aR)-4-{[2-fluoro-5-(4,4,5,5-tetramethyl-1,3,2-dioxaborolan-2-yl)benzyl]oxy}-1,1a,6,6a-tetrahydrocyclopropa[a]indene-1-carboxylate (205 mg, 0.45 mmol), 5-bromo-4-methyl-2-[3-(methylsulfonyl)propoxy]pyridine (140 mg, 0.45 mmol), Pd(PPh$_3$)$_4$ (53 mg, 0.045 mmol), and potassium carbonate (157 mg, 1.1 mmol) were combined in a 50 ml RBF. The vessel was sealed, degassed (3×) with nitrogen, and 4:1 dioxane:water (5 ml, sparged with nitrogen) was added and the vessel degassed (3×). The mixture was heated at 100° C. for 5 hrs. The mixture was diluted with 1:1 brine:water:(50 ml), acidified with acetic acid and extracted with ethyl acetate (3×50 ml). The combined organic fractions were washed with brine, dried over sodium sulfate, filtered, and the volatiles removed in vacuo. The crude product was purified by column chromatagraphy on silica gel, BIOTAGE (Uppsala, Sweden) HP 25 g, using a gradient eluant of 0-100% EtOAc:Hexanes to afford the title compound. MS (m/z): 526 (M+H)$^+$.

Example 20

4-(2,6-Difluoro-3-[6-(3-methanesulfonyl-propoxy)-2-methyl-pyridin-3-yl]-benzyloxy)-1,1a,6,6a-tetrahydro-cyclopropa[a]indene-1-carboxylic acid

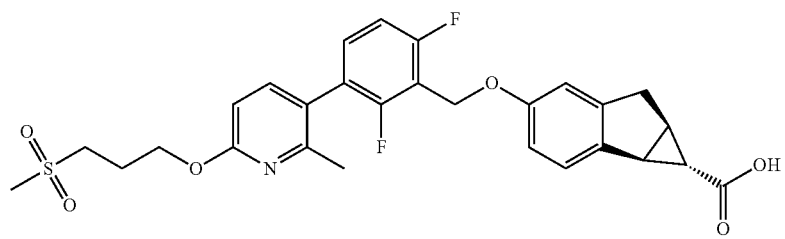 [SMILES: Cc1nc(OCCCS(C)(=O)=O)ccc1-c1ccc(F)c(COc2ccc3c(c2)C[C@H]2[C@H](C(=O)O)[C@@H]32)c1F]

Step A. 2,6-Difluoro-3-[6-(3-methanesulfonyl-propoxy)-2-methyl-pyridin-3-yl]-benzaldehyde A mixture of 3-bromo-6-(3-methanesulfonyl-propoxy)-2-methyl-pyridine from Reference Example 6 (400 mg, 1.25 mmol), boric acid (350 mg, 1.5 eq), Pd$_2$(dba)$_3$ (60 mg, 0.05 eq), s-Phos (53 mg, 0.1 eq) and K$_3$PO$_4$ (930 mg, 3 eq) in a co-solvent of toluene (8 mL) and water (3 mL) was refluxed at 110° C. under N$_2$ atmosphere overnight. The mixture was cooled to rt, partitioned by ethyl acetate and water. The aqueous layer was extracted with ethyl acetate twice and the combined organic phase was washed with a saturated aqueous solution of sodium bicarbonate and brine, dried over anhydrous Na$_2$SO$_4$, and concentrated. The residue was purified by flash column chromatography to afford the title compound. MS m/e (M+H$^+$): 370.

Step B. (2,6-Difluoro-3-[6-(3-methanesulfonyl-propoxy)-2-methyl-pyridin-3-yl]-phenyl)-methanol To a solution of 2,6-difluoro-3-[6-(3-methanesulfonyl-propoxy)-2-methyl-pyridin-3-yl]-benzaldehyde from Step A (140 mg, 0.38 mmol) in MeOH (1 mL) was added NaBH$_4$ (18 mg, 1.2 eq) at 0° C. portion-wise. Then the mixture was allowed to warm to rt and stirred for 1 h, diluted with H$_2$O (5 ml), extracted with DCM (5 mL×3). The combined extract was washed with water and brine, dried (Na$_2$SO$_4$), filtered and evaporated to give the title compound as the crude product. MS m/e (M+H$^+$): 372.3.

Step C. 4-(2,6-Difluoro-3-[6-(3-methanesulfonyl-propoxy)-2-methyl-pyridin-3-yl]-benzyloxy)-1,1a,6,6a-tetrahydro-cyclopropa[a]indene-1-carboxylic acid, ethyl ester To a solution of (2,6-difluoro-3-[6-(3-methanesulfonyl-propoxy)-2-methyl-pyridin-3-yl]-phenyl)-methanol from Step B (75 mg, 0.2 mmol), (1S,1aS,6aR)-4-hydroxy-1,1a,6,6a-tetrahydrocyclopropa[a]indene-1-carboxylic acid, ethyl ester from Reference Example 1 (57 mg, 1.3 eq) and PPh$_3$ (70 mg, 1.3 eq) in dry DCM (1.5 mL) was added a solution of DIAD (60 mg, 1.5 eq) in 0.5 mL of DCM at 0° C. dropwise. The resulting solution was stirred at rt overnight, diluted with H$_2$O, and extracted with DCM (5 ml×3). The combined extract was washed with water and brine, dried (Na$_2$SO$_4$), filtered and evaporated. The residue was purified by flash column chromatography to afford the title compound. MS m/e (M+H$^+$): 572.5.

Step D. 4-(2,6-Difluoro-3-[6-(3-methanesulfonyl-propoxy)-2-methyl-pyridin-3-yl]-benzyloxy-1,1a,6,6a-tetrahydro-cyclopropa[a]indene-1-carboxylic acid To a solution of 4-(2,6-difluoro-3-[6-(3-methanesulfonyl-propoxy)-2-methyl-pyridin-3-yl]-benzyloxy)-1,1a,6,6a-tetrahydro-cyclopropa[a]indene-1-carboxylic acid, ethyl ester (60 mg, 0.1 mmol) in MeOH (2 mL) was added an aqueous solution of LiOH (1N, 1.5 eq) in 1 mL H$_2$O at 0° C. dropwise. The resulting solution was allowed to warm to RT, and stirred overnight, then cooled to 0° C. again, acidified with 3 N HCl to pH=3. The aqueous layer was extracted with ethyl acetate (5 ml×3). The combined extracts were washed with water and brine, dried (Na$_2$SO$_4$), filtered and evaporated. The residue was purified by prep-HPLC to afford the title compound. MS m/e (M+H$^+$): 544 (M+H)$^+$; $^1$H NMR (MeOD, 400 MHz): δ 7.55 (d, J=8.4 Hz, 1H), 7.32 (m, 1H), 7.22 (d, J=8.4 Hz, 1H), 7.09 (t, J=8.8 Hz, 1H), 6.83 (s, 1H), 6.78 (m, 2H), 5.10 (s, 2H), 4.45 (t, J=6.0 Hz, 2H), 3.30 (m, 2H), 3.21 (m, 1H), 2.99 (m, 4H), 2.83 (d, J=6.0 Hz, 1H), 2.39 (m, 1H), 2.37-2.25 (m, 5H), 1.03 (m, 1H).

The following compounds were prepared in a similar manner to Example 20 and appropriate commercially available reagents.

| Ex. No. | Structure | Compound Name | MS observed [M + H]+ |
|---|---|---|---|
| 21 | 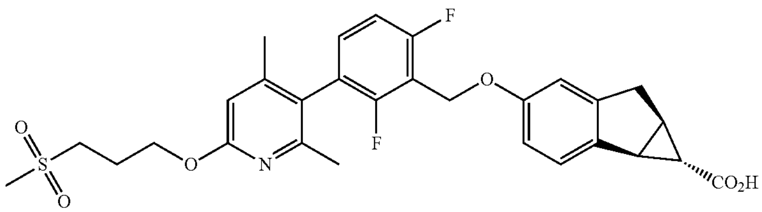 [SMILES: Cc1cc(OCCCS(C)(=O)=O)nc(C)c1-c1ccc(F)c(COc2ccc3c(c2)C[C@H]2[C@H](C(=O)O)[C@@H]32)c1F] | 4-(2,6-difluoro-3-[6-(3-methanesulfonyl-propoxy)-2,4-dimethyl-pyridin-3-yl]-benzyloxy)-1,1a,6,6a-tetrahydro-cyclopropa[a]indene-1-carboxylic acid | 558.6 |
| 22 | 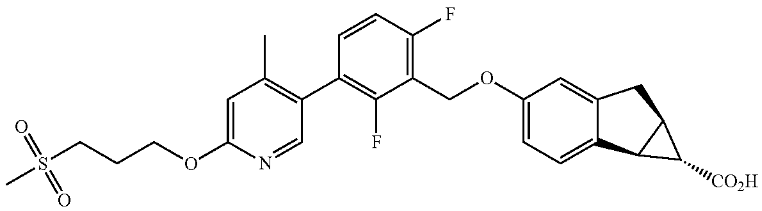 [SMILES: Cc1cc(OCCCS(C)(=O)=O)ncc1-c1ccc(F)c(COc2ccc3c(c2)C[C@H]2[C@H](C(=O)O)[C@@H]32)c1F] | 4-(2,6-difluoro-3-[6-(3-methanesulfonyl-propoxy)-4-methyl-pyridin-3-yl]-benzyloxy)-1,1a,6,6a-tetrahydro-cyclopropa[a]indene-1-carboxylic acid | 544.2 |

Example 23

(1S,1aS,6aR)-4-((4-methyl-3-(1-(3-(methylsulfonyl)propyl)-1H-pyrrolo[2,3-b]pyridin-5-yl)benzyl)oxy)-1,1a,6,6a-tetrahydrocyclopropa[a]indene-1-carboxylic acid

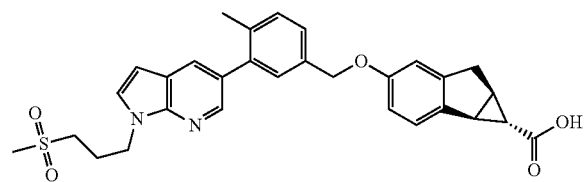 [SMILES: Cc1ccc(COc2ccc3c(c2)C[C@H]2[C@H](C(=O)O)[C@@H]32)cc1-c1cnc2c(ccn2CCCS(C)(=O)=O)c1]

Step A. (3-bromo-4-methylphenyl)methanol

To a solution of 3-bromo-4-methylbenzoic acid (5.0 g, 0.02 mol) in THF (40 mL) was added dropwise BH₃—(CH₃)₂ S (14 mL, 10M) slowly at 0° C. The resulting mixture was stirred at 25° C. for 18 hours. LCMS showed compound 3-bromo-4-methylbenzoic acid was consumed completely. The solution was quenched with HCl (1M), extracted with EtOAc (30 mL×3). The combined organic layer was washed with brine, dried, and concentrated to give the residue, which was purified by silica gel column to give the title compound. ¹HNMR (400 MHz, CDCl₃) δ 7.54 (s, 1H), 7.21-7.38 (m, 2H), 4.63 (s, 2H), 2.48 (s, 3H), 2.09 (s, 1H), 1.79-1.96 (m, 1H).

Step B. (1S,1aS,6aR)-ethyl 4-((3-bromo-4-methyl-benzyl)oxy)-1,1a,6,6a-tetrahydro-cyclopropa[a]indene-1-carboxylic acid, ethyl ester To a solution of (3-bromo-4-methylphenyl)methanol from Reference Example 1 (500 mg, 2.49 mmol) in THF (2.0 mL) was added (1S,1aS,6aR)-4-hydroxy-1,1a,6,6a-tetrahydrocyclopropa[a]indene-1-carboxylic acid, ethyl ester from reference Example 1(452 mg, 2.07 mmol), PPh₃ (814 mg, 3.11 mmol), DIAD (628 mg, 3.11 mmol). The resulting mixture was stirred at rt. for 1 hour. LCMS showed the compound (3-bromo-4-methylphenyl)methanol was consumed completely. The solution was concentrated to give the residue, which was purified by silica gel column to give the title compound. MS m/z: 401, 403 (M+H)⁺.

Step C. (1S,1aS,6aR)-ethyl 4-((4-methyl-3-(4,4,5,5-tetramethyl-1,3,2-dioxaborolan-2-yl)benzyl)oxy)-1,1a,6,6a-tetrahydrocyclopropa[a]indene-1-carboxylic acid, ethyl ester To a solution of (1S,1aS,6aR)-ethyl 4-((3-bromo-4-methylbenzyl)oxy)-1,1a,6,6a-tetrahydrocyclopropa[a]indene-1-carboxylic acid, ethyl ester (200 mg, 0.50 mmol) in dioxane (5.0 mL) was added Pinacol diester (190 mg, 0.75 mmol), KOAc (98 mg, 1.0 mmol) and Pd(dppf)₂Cl₂ (37 mg, 0.05 mmol) in N₂. The resulting mixture was stirred at 100° C. for 18 hours. TLC showed compound (1S,1aS,6aR)-ethyl 4-((3-bromo-4-methylbenzyl)oxy)-1,1a,6,6a-tetrahydrocyclopropa[a]indene-1-carboxylic acid, ethyl ester was consumed completely. The solution was filtered and the filtrate was concentrated to give the residue, which was purified by preparative TLC to give the title compound. ¹H-NMR (400 MHz, CDCl₃) δ 7.77 (s, 1H), 7.35-7.38 (m, 1H), 7.16-7.21 (m, 2H), 6.73-6.77 (m, 2H), 4.94 (s, 2H), 4.14 (dd, 2H, J₁=J₂=7.2 Hz), 3.21-3.26 (m, 1H), 2.96-3.01 (m, 1H), 2.87 (d, 1H, J=6.4 Hz), 2.52 (s, 3H), 2.35-2.42 (m, 1H), 1.55 (s, 1H), 1.33 (s, 12H), 1.25 (t, 3H, J=7.2 Hz), 1.17-1.18 (m, 1H).

Step D. (1S,1aS,6aR)-ethyl 4-((4-methyl-3-(1H-pyrrolo[2,3-b]pyridin-5-yl)benzyl)oxy)-1,1a,6,6a-tetrahydrocyclopropa[a]indene-1-carboxylic acid, ethyl ester To a solution of compound (1S,1aS,6aR)-ethyl 4-((4-methyl-3-(4,4,5,5-tetramethyl-1,3,2-dioxaborolan-2-yl)benzyl)oxy)-1,1a,6,6a-tetrahydrocyclopropa[a]indene-1-carboxylic acid, ethyl ester (750 mg, 1.68 mmol) in THF (9.0 mL) and H₂O (3.0 mL) was added compound 5-bromo-1H-pyrrolo[2,3-b]pyridine (300 mg, 1.15 mmol), K₃PO₄ (967 mg, 4.56 mmol) and Pd(dppf)₂Cl₂ (146 mg, 0.20 mmol) in N₂. The resulting mixture was sealed and heated to 100° C. by microwave irradiation for 10 mins. The solution was filtered and the filtrate was concentrated to give the residue, which was purified by p-TLC to give the title compound. MS m/z: 439 (M+H)+

Step E. (1S,1aS,6aR)-ethyl 4-((4-methyl-3-(1-(3-(methylsulfonyl)propyl)-1H-pyrrolo[2,3-b]pyridin-5-yl)benzyl)oxy)-1,1a,6,6a-tetrahydrocyclopropa[a]indene-1-carboxylic acid, ethyl ester To a solution of (1S,1aS,6aR)-ethyl 4-((4-methyl-3-(1H-pyrrolo[2,3-b]pyridin-5-yl)benzyl)oxy)-1,1a,6,6a-tetrahydrocyclopropa[a]indene-1-carboxylic acid, ethyl ester (200 mg, 0.46 mmol) in DMF (5.0 mL) was added NaH (55 mg, 0.37 mmol), the resulting mixture was stirred at RT for 15 mins, then 3-(methylsulfonyl)propyl 4-methylbenzenesulfonate (201 mg, 0.49 mmol) was added and stirred for 2 hours. TLC showed 3-(methylsulfonyl)propyl 4-methylbenzenesulfonate was consumed completely. The solution was quenched with H₂O and extracted with EtOAc (3×10 mL). The combined organic layer was washed with brine, dried and concentrated to give the residue, which was purified by preparative TLC to give the title compound. MS m/z: 559 (M+H)+

Step F. (1S,1aS,6aR)-4-((4-methyl-3-(1-(3-(methylsulfonyl)propyl)-1H-pyrrolo[2,3-b]pyridin-5-yl)benzyl)oxy)-1,1a,6,6a-tetrahydrocyclopropa[a]indene-1-carboxylic acid To a solution of (1S,1aS,6aR)-ethyl 4-((4-methyl-3-(1-(3-(methylsulfonyl)propyl)-1H-pyrrolo[2,3-b]pyridin-5-yl)benzyl)oxy)-1,1a,6,6a-tetrahydrocyclopropa[a]indene-1-carboxylic acid, ethyl ester (150 mg, 0.27 mmol) in THF (9.0 mL), MeOH (3.0 mL), H₂O (3.0 mL) was added LiOH.H₂O (45 mg, 1.07 mmol). The resulting mixture was stirred at rt. for 4 hours. LCMS showed compound (1S,1aS, 6aR)-ethyl 4-((4-methyl-3-(1-(3-(methylsulfonyl)propyl)-1H-pyrrolo[2,3-b]pyridin-5-yl)benzyl)oxy)-1,1a,6,6a-tetrahydrocyclopropa[a]indene-1-carboxylic acid, ethyl ester was consumed completely. H₂O was added and the solution was acidified with HCl (1M) to pH=2.5, and extracted with EtOAc (10 mL×3). The combined organic layer and washed with brine, dried and concentrated to give the residue, which was purified by p-HPLC to give the title compound. MS m/z: 531 (M+H)+. ¹HNMR (400 MHz, CDCl₃) δ: 8.45 (s, 1H), 8.16 (s, 1H), 7.40-7.41 (m, 1H), 7.37-7.39 (m, 1H), 7.33-7.34 (m, 1H), 7.25-7.29 (m, 1H), 7.22-7.25 (m, 2H), 6.80 (s, 1H), 6.75-6.77 (m, 1H), 6.67-6.68 (m, 1H), 5.02 (s, 2H), 4.59-4.63 (m, 2H), 3.27-3.29 (m, 1H), 3.17-3.24 (m, 2H), 3.13-3.15 (m, 1H), 2.95 (s, 4H), 2.49-2.53 (m, 3H), 2.23 (s, 1H), 1.19 (s, 1H).

Example 24 was prepared in a similar manner to Example 23 using the appropriate intermediates and commercially available starting materials:

| Ex. No. | Structure | Compound Name | MS observed [M + H]+ |
|---|---|---|---|
| 24 | 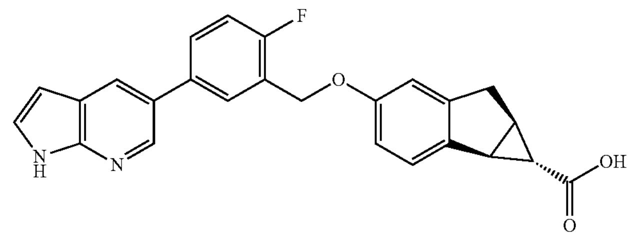 [SMILES: O=C(O)[C@H]1[C@@H]2Cc3cc(OCc4cc(-c5cnc6[nH]ccc6c5)ccc4F)ccc3[C@@H]21] | (1S,1aS,6aR)-4-((2-fluoro-5-(1H-pyrrolo[2,3-b]pyridin-5-yl)benzyl)oxy)-1,1a,6,6a-tetrahydrocyclopropa[a]indene-1-carboxylic acid | 415.3 |

Example 25

(1S,1aS,6aR)-4-((2-fluoro-5-(2-methyl-6-(((1S,2R)-2-(methylsulfonyl)cyclohexyl)methoxy)pyridin-3-yl)benzyl)oxy)-1,1a,6,6a-tetrahydrocyclopropa[a]indene-1-carboxylic acid

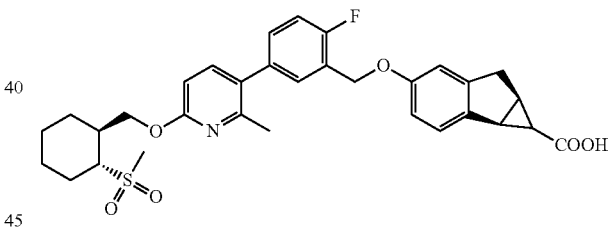

Step A. 2-(Hydroxymethyl)cyclohexanol

To a solution of lithium aluminum hydride (5.4 g, 0.15 mol) in THF (30 mL) with N₂ was added ethyl 2-oxocyclohexanecarboxylate (8.0 g, 0.05 mmol) dissolved in THF (20 mL) slowly at 0° C. The resulting mixture was stirred at 0° C. for 1 hour. TLC showed ethyl 2-oxocyclohexanecarboxylate was consumed completely. The solution was quenched with H₂O (6 mL), NaOH (15%, 6 mL), stirred for 15 mins. Then H₂O (0.6 mL) was added, the solution was filtered and the filtrate was concentrated in vacuo to give the title compound.

Step B. 2-((5-Bromo-6-methylpyridin-2-yloxy)methyl)cyclohexanol

To a solution of 2-(hydroxymethyl)cyclohexanol (4.7 g, 36 mmol) in DMSO (50 mL) was added 3-bromo-6-fluoro-2-methylpyridine (2.3 g, 12 mol), KOH (2.8 g, 0.05 mol). The resulting mixture was stirred at rt. for 4 hours. TLC showed 2-(hydroxymethyl)cyclohexanol was consumed completely. The solution was acidified with HCl (1M) to pH=7, extracted with EtOAc (30 mL×3). The combined organic layer was washed with brine (50 mL), dried, and concentrated in vacuo to give the residue, which was purified by column chromatography on silica gel (PE/EA=1/1) to give the title compound. $^1$HNMR (400 MHz, CDCl$_3$) δ: 7.63 (d, 1H, J=8.4 Hz), 6.48 (d, 1H, J=8.8 Hz), 4.86-4.89 (m, 1H), 4.45 (s, 1H), 4.04 (dd, 1H, J$_1$=3.2 Hz, J$_2$=3.6 Hz), 3.22-3.27 (m, 1H), 2.54 (s, 3H), 1.97-2.04 (m, 1H), 1.69-1.80 (m, 4H), 1.53-1.59 (m, 1H), 1.20-1.34 (m, 5H).

Step C. 2-((5-Bromo-6-methylpyridin-2-yloxy)methyl)cyclohexyl methanesulfonate

To a solution of 2-((5-bromo-6-methylpyridin-2-yloxy)methyl)cyclohexanol (2 g, 6.67 mmol) in DCM (15 mL) was added Et$_3$N (2.1 g, 0.02 mol), MsCl (1.5 g, 0.01 mol) slowly at 0° C. The resulting mixture was warmed to rt. and stirred for 1 hour. TLC showed 2-((5-bromo-6-methylpyridin-2-yloxy)methyl)cyclohexanol was consumed completely. The solution was quenched with H$_2$O, and extracted with DCM (15 mL×3). The combined organic layer was dried and concentrated in vacuo to give the title compound. MS m/z: 379, 381 (M+H)$^+$.

Step D. 3-Bromo-2-methyl-6-((2-(methylthio)cyclohexyl)methoxy)pyridine

To a solution of 2-((5-bromo-6-methylpyridin-2-yloxy)methyl)cyclohexyl methanesulfonate (3 g, 7.94 mmol) in MeOH (20 mL) was added compound NaSCH$_3$ (2.3 g, 0.03 mol). The resulting mixture was stirred at 80° C. for 18 hours. TLC showed 2-((5-bromo-6-methylpyridin-2-yloxy)methyl)cyclohexyl methanesulfonate was consumed completely. The solution was concentrated in vacuum to remove the solvent, then H$_2$O was added and the solution was extracted with EtOAc (3×15 mL). The combined organic layer was washed with brine (20 mL), dried and concentrated in vacuo to give the title compound along with some 3-bromo-2-methyl-6-((1-cyclohexenyl)methoxy)pyridine and 3-bromo-2-methyl-6-((3-cyclohexenyl)methoxy)pyridine. MS m/z: 331, 333 (M+H)$^+$.

Step E. 3-Bromo-2-methyl-6-(((1S,2S)-2-(methylsulfonyl)cyclohexyl)methoxy)pyridine To a solution of 3-bromo-2-methyl-6-((2-(methylthio)cyclohexyl)methoxy)pyridine (600 mg, 1.82 mmol) in DCM (5.0 mL) was added mCPBA (944 mg, 5.54 mmol) at 0° C. The resulting mixture was warmed to rt. and stirred for 18 hours. TLC showed 3-bromo-2-methyl-6-((2-(methylthio)cyclohexyl)methoxy)pyridine was consumed completely. Water was added and the solution was separated with DCM (15 mL×3). The combined organic layer was dried and concentrated in vacuo to give the residue, which was purified by column chromatography on silica gel (PE/EA=2/1) to give the title compound. $^1$HNMR (400 MHz, CDCl$_3$) δ: 7.60 (d, 1H, J=8.4 Hz), 6.45 (d, 1H, J=8.4 Hz), 4.73-4.77 (m, 1H), 4.38-4.43 (m, 1H), 3.16-3.20 (m, 1H), 2.98 (s, 1H), 2.75-2.80 (m, 1H), 2.51 (s, 3H), 2.13-2.17 (m, 1H), 1.94-2.03 (m, 3H), 1.51-1.64 (m, 3H), 1.38-1.46 (m, 2H).

Step E. 3-Bromo-2-methyl-6-(((1S,2R)-2-(methylsulfonyl)cyclohexyl)methoxy)pyridine To a solution of 3-bromo-2-methyl-6-(((1S,2S)-2-(methylsulfonyl)cyclohexyl)methoxy)pyridine (300 mg, 0.83 mmol) in DMF (8 mL) was added NaH (133 mg, 3.32 mmol). The resulting mixture was stirred at rt. for 4 hours. TLC showed 3-bromo-2-methyl-6-(((1S,2S)-2-(methylsulfonyl)cyclohexyl)methoxy)pyridine (300 mg, 0.83 mmol) was consumed completely. The solution was quenched with H$_2$O, and extracted with EtOAc (10 mL×3). The combined organic layer was washed with brine, dried and concentrated in vacuo to give the residue, which was purified in prep. silica TLC (PE/EA=1/1) to give the title compound. $^1$HNMR (400 MHz, CDCl$_3$) δ: 7.60 (d, 1H, J=8.8 Hz), 6.44 d, 1H, J=8.4 Hz), 5.28 (m, 1H), 4.54-4.58 (m, 2H), 4.38-4.32 (m, 1H), 3.03-3.05 (m, 1H), 2.88 (s, 3H), 2.50 (s, 3H), 2.24-2.29 (m, 2H), 1.72-1.92 (m, 1H), 1.46-1.76 (m, 9H), 0.78-0.89 (m, 3H).

Step F. (1S,1aS,6aR)-4-((2-fluoro-5-(2-methyl-6-(((1S,2R)-2-(methylsulfonyl)cyclohexyl)methoxy)pyridin-3-yl)benzyl)oxy)-1,1a,6,6a-tetrahydrocyclopropa[a]indene-1-carboxylic acid, ethyl ester To a solution of 3-bromo-2-methyl-6-(((1S,2R)-2-(methylsulfonyl)cyclohexyl)methoxy)pyridine (140 mg, 0.39 mmol) in THF (3.0 mL) and H$_2$O (1.0 mL) was added (1S,1aS,6aR)-4-((2-fluoro-5-(4,4,5,5-tetramethyl-1,3,2-dioxaborolan-2-yl)benzyl)oxy)-1,1a,6,6a-tetrahydrocyclopropa[a]indene-1-carboxylic acid, ethyl ester (211 mg, 0.46 mmol), Na$_2$CO$_3$ (108 mg, 0.48 mmol) and Pd(dppf)$_2$Cl$_2$ (30 mg, 0.04 mmol) in N$_2$. The resulting mixture was stirred at 100° C. for 2 hours. TLC showed that bromo-2-methyl-6-(((1S,2R)-2-(methylsulfonyl)cyclohexyl)methoxy)pyridine was consumed completely. The solution was filtered and the filtrate was concentrated in vacuo to give the residue, which was purified by prep.silica TLC (PE/EA=1/1) to give the title compound. MS m/z: 608 (M+H)$^+$ Step G. (1S,1aS,6aR)-4-((2-fluoro-5-(2-methyl-6-(((1S,2R)-2-(methylsulfonyl)cyclohexyl)methoxy)pyridin-3-yl)benzyl)oxy)-1,1a,6,6a-tetrahydrocyclopropa[a]indene-1-carboxylic acid To a solution of (1S,1aS,6aR)-4-((2-fluoro-5-(2-methyl-6-(((1S,2R)-2-(methylsulfonyl)cyclohexyl)methoxy)pyridin-3-yl)benzyl)oxy)-1,1a,6,6a-tetrahydrocyclopropa[a]indene-1-carboxylic acid, ethyl ester (70 mg, 0.12 mmol) in THF (3.0 mL), MeOH (1.0 mL) and H$_2$O (1.0 mL) were added LiOH.H$_2$O (42 mg, 0.48 mmol). The resulting mixture was stirred at rt. for 4 hours. LCMS showed (1S,1aS,6aR)-4-((2-fluoro-5-(2-methyl-6-(((1S,2R)-2-(methylsulfonyl)cyclohexyl)methoxy)pyridin-3-yl)benzyl)oxy)-1,1a,6,6a-tetrahydrocyclopropa[a]indene-1-carboxylic acid, ethyl ester was consumed completely. H$_2$O (3 mL) was added and the solution was acidified with HCl (1 M) to pH=2.5, extracted with EtOAc (10 mL×3). The combined organic layer was washed with brine, dried and concentrated in vacuum to give the residue, which was purified by preparative HPLC on a GILSON 281 instrument fitted with a YMC-Actus Triart C18 (150*30 mm*5 um) using water and acetonitrile as the eluents. Mobile phase A: water (containing 0.1% TFA, v/v), mobile phase B:acetonitrile. Gradient: 39-59% B, 0-10 min; 100% B, 10.5-12.5 min; 5% B, 13-15 min to give compound two enantiomers, it was separated by SFC (AS-H_S_5_5_40_3ML_8 MIN) to give the title compound and its isomer. MS m/z: 580 (M+H)$^+$ Isomer 1: $^1$HNMR (400 MHz, CDCl$_3$) δ: 7.35-7.43 (m, 2H), 7.20-7.25 (m, 2H), 7.10-7.19 (m, 1H), 6.75-6.81 (m, 2H), 6.62 (d, 1H, J=8.4 Hz), 5.12 (s, 2H), 4.49-4.61 (m, 2H), 3.72-3.73 (m, 4H), 3.12-3.48 (m, 2H), 2.93-3.73 (m, 5H), 2.48-2.49 (m, 2H), 2.07 (s, 5H), 2.11-2.20 (m, 1H), 1.78-2.19 (m, 5H), 1.49-1.62 (m, 3H), 1.23-1.46 (m, 3H), 1.11-1.22 (m, 1H).

Isomer 2: $^1$HNMR (400 MHz, CDCl$_3$) δ: 7.34-7.45 (m, 2H), 7.12-7.28 (m, 2H), 7.08-7.11 (m, 1H), 6.72-6.88 (m, 2H), 6.60 (d, 1H, J=8.4 Hz), 5.12 (s, 2H), 4.47-4.65 (m, 1H), 4.43-4.45 (m, 1H), 3.23-3.35 (m, 1H), 3.12-3.24 (m, 1H), 2.98-3.15 (m, 1H), 2.93 (s, 3H), 2.48-2.52 (m, 1H), 2.31 (s, 5H), 2.12-2.20 (m, 2H), 1.79-1.98 (m, 1H), 1.37-1.66 (m, 6H), 1.18-1.19 (m, 1H).

Example 26

(1S,1aS,6aR)-4-((5-(6-((1,2-dihydroxycyclohexyl)methoxy)-2-methylpyridin-3-yl)-2-fluorobenzyl)oxy)-1,1a,6,6a-tetrahydrocyclopropa[a]indene-1-carboxylic acid

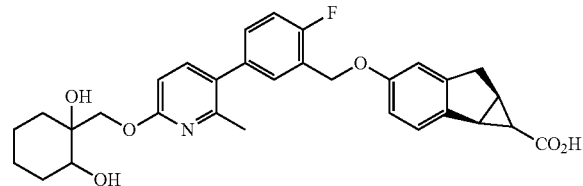 [SMILES: Cc1nc(OCC2(O)CCCCC2O)ccc1-c1ccc(F)c(COc2ccc3c(c2)C[C@H]2C(C(=O)O)[C@@H]32)c1]

Step A. 1-((5-bromo-6-methylpyridin-2-yloxy)methyl)cyclohexane-1,2-diol

To a solution of 3-bromo-2-methyl-6-((1-cyclohexenyl)methoxy)pyridine from Example 25, Step D (250 mg, 0.89 mmol) in acetone (5.0 mL) was added OsO$_4$ (124 mg, 1.06 mmol) and NMO (23 mg, 0.09 mmol) at 0° C. The resulting mixture was stirred at 0° C. for 1 hour. TLC showed 3-bromo-2-methyl-6-((1-cyclohexenyl)methoxy)pyridine was consumed completely.

The solution was quenched with EtOH (3 mL), concentrated in vacuo to give the residue, which was purified by prep.silica TLC (PE/EA=1/1) to give the title compound. $^1$HNMR (400 MHz, CDCl$_3$) δ: 7.68 (d, 1H, J=8.4 Hz), 6.53 (d, 1H, J=8.8 Hz), 4.60 (d, 1H, J=12.0 Hz), 3.95 (d, 1H, J=12.0 Hz), 3.38-3.41 (m, 1H), 3.20 (s, 1H), 2.54 (s, 3H), 1.69-1.82 (m, 4H), 1.58-1.62 (m, 3H), 1.41-1.52 (m, 2H).

Step B. (1S,1aS,6aR)-4-((5-(6-((1,2-dihydroxycyclohexyl)methoxy)-2-methylpyridin-3-yl)-2-fluorobenzyl)oxy)-1,1a,6,6a-tetrahydrocyclopropa[a]indene-1-carboxylic acid, ethyl ester To a solution of 1-((5-bromo-6-methylpyridin-2-yloxy)methyl)cyclohexane-1,2-diol (130 mg, 0.41 mmol) in THF (3.0 mL) and H$_2$O (1.0 mL) was added 4-[2-fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester from Reference Example 10, Step D (224 mg, 0.49 mmol), Na$_2$CO$_3$ (113 mg, 0.82 mmol) and Pd(dppf)$_2$Cl$_2$ (30 mg, 0.04 mmol) in N$_2$. The resulting mixture was stirred at 100° C. for 2 hours. The solution was filtered and the filtrate was concentrated in vacuo to give the title compound as the crude product. MS m/z: 562 (M+H)$^+$.

Step C. (1S,1aS,6aR)-4-((5-(6-((1,2-dihydroxycyclohexyl)methoxy)-2-methylpyridin-3-yl)-2-fluorobenzyl)oxy)-1,1a,6,6a-tetrahydrocyclopropa[a]indene-1-carboxylic acid To a solution of (1S,1aS,6aR)-4-((5-(6-((1,2-dihydroxycyclohexyl)methoxy)-2-methylpyridin-3-yl)-2-fluorobenzyl)oxy)-1,1a,6,6a-tetrahydrocyclopropa[a]indene-1-carboxylic acid, ethyl ester (120 mg, 0.21 mmol) in THF (3.0 mL), MeOH (1.0 mL), and H$_2$O (1.0 mL) was added LiOH.H$_2$O (36 mg, 0.85 mmol). The resulting mixture was stirred at rt. for 4 hours. LCMS showed (1S,1aS,6aR)-4-((5-(6-((1,2-dihydroxycyclohexyl)methoxy)-2-methylpyridin-3-yl)-2-fluorobenzyl)oxy)-1,1a,6,6a-tetrahydrocyclopropa[a]indene-1-carboxylic acid, ethyl ester was consumed completely. H$_2$O was added and the solution was acidified with HCl (1M) to pH=2.5, and extracted with EtOAc (10 mL×3). The combined organic layer was washed with brine, dried and concentrated in vacuo to give the residue, which was purified by preparative HPLC on a GILSON 281 instrument fitted with a YMC-pack ODS-AQ (150*30 mm*5 um) using water and acetonitrile as the eluents. Mobile phase A: water (containing 0.1% TFA, v/v), mobile phase B: acetonitrile. Gradient: 51-81% B, 0-10 min; 100% B, 10.5-12.5 min; 5% B, 13-15 min to give the title compound. MS m/z: 534 (M+H)$^+$; $^1$HNMR (400 MHz, CDCl$_3$) δ: 7.67 (d, 1H, J=8.0 Hz), 7.38 (s, 1H), 7.14-7.26 (m, 3H), 6.75-6.86 (m, 3H), 5.14 (s, 2H), 4.52-4.54 (m, 1H), 4.13-4.15 (m, 1H), 3.49-3.53 (m, 1H), 3.12-3.33 (m, 1H), 2.95-3.04 (m, 2H), 2.49 (s, 1H), 2.39 (d, 3H, J=4.8 Hz), 1.51-1.88 (m, 7H), 1.17-1.25 (m, 2H).

Example 27

(1S,1aS,6aR)-4-((5-(6-(((2R,3S)-2,3-dihydroxycyclohexyl)methoxy)-2-methylpyridin-3-yl)-2-fluorobenzyl)oxy)-1,1a,6,6a-tetrahydrocyclopropa[a]indene-1-carboxylic acid

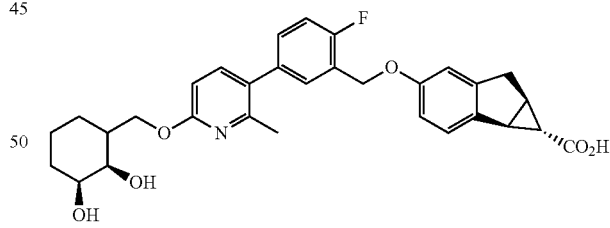

Step A. (1S,2R,3R)-3-((5-bromo-6-methylpyridin-2-yloxy)methyl)cyclohexane-1,2-diol A solution of AD-mix-α (Sigma-Aldrich catalogue #392758, 993 mg, 1.28 mmol) in t-BuOH (5.0 mL) and H$_2$O (5.0 mL) was stirred for 30 mins, then MeSO$_2$NH$_2$(68 mg, 0.71 mmol) was added at rt. and stirred for 10 mins. 3-bromo-2-methyl-6-((3-cyclohexenyl)methoxy)pyridine from Example 25, Step D (200 mg, 0.71 mmol) was added and the solution was stirred at rt. for 18 hours. TLC showed the 3-bromo-2-methyl-6-((3-cyclohexenyl)methoxy)pyridine was consumed completely. The solution was quenched with saturated Na₂SO₃, and extracted with EtOAc (10 mL×3). The combined organic layer was washed with brine, dried and concentrated in vacuo to give the residue, which was purified by prep.silica TLC (PE/EA=1/1) to give the title compound. ¹HNMR (400 MHz, CDCl₃) δ: 7.63 (d, 1H, J=8.4 Hz), 6.47-6.49 (m, 1H), 4.75-4.78 (m, 2H), 4.02-4.11 (m, 2H), 3.29 (d, 1H, J=10.4 Hz), 2.53 (s, 3H), 2.32 (s, 1H), 1.91-2.06 (m, 2H), 1.27-1.57 (m, 9H).

Step B. (1S,1aS,6aR)-4-((5-(6-(((1R,2R,3S)-2,3-dihydroxycyclohexyl)methoxy)-2-methylpyridin-3-yl)-2-fluorobenzyl)oxy)-1,1a,6,6a-tetrahydrocyclopropa[a]indene-1-carboxylic acid, ethyl ester To a solution of (1S,2R,3R)-3-((5-bromo-6-methylpyridin-2-yloxy)methyl)cyclohexane-1,2-diol (50 mg, 0.16 mmol) in THF (3.0 mL) and H₂O (1.0 mL) was added 4-[2-fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester (86 mg, 0.19 mmol), Na₂CO₃ (45 mg, 0.32 mmol) and Pd(dppf)₂Cl₂ (15 mg, 0.02 mmol) in N₂. The resulting mixture was stirred at 100° C. for 2 hours. TLC showed (1S,2R,3R)-3-((5-bromo-6-methylpyridin-2-yloxy)methyl)cyclohexane-1,2-diol was consumed completely. The solution was filtered and the filtrate was concentrated in vacuum to give the title compound (crude). MS m/z: 562 (M+H)⁺

Step C. (1S,1aS,6aR)-4-((5-(6-(((1R,2R,3S)-2,3-dihydroxycyclohexyl)methoxy)-2-methylpyridin-3-yl)-2-fluorobenzyl)oxy)-1,1a,6,6a-tetrahydrocyclopropa[a]indene-1-carboxylic acid To a solution of (1S,1 aS,6aR)-4-((5-(6-(((1R,2R,3S)-2,3-dihydroxycyclohexyl)methoxy)-2-methylpyridin-3-yl)-2-fluorobenzyl)oxy)-1,1a,6,6a-tetrahydrocyclopropa[a]indene-1-carboxylic acid, ethyl ester (70 mg, 0.12 mmol) in THF (3.0 mL), MeOH (1.0 mL), H₂O (1.0 mL) was added LiOH.H₂O (21 mg, 0.5 mmol). The resulting mixture was stirred at rt. for 4 hours. LCMS showed (1S,1aS,6aR)-4-((5-(6-(((1R,2R,3S)-2,3-dihydroxycyclohexyl)methoxy)-2-methylpyridin-3-yl)-2-fluorobenzyl)oxy)-1,1a,6,6a-tetrahydrocyclopropa[a]indene-1-carboxylic acid, ethyl ester was consumed completely. H₂O was added and the solution was acidified with HCl (1M) to pH=2.5, and extracted with EtOAc (10 mL×3). The combined organic layer was washed with brine, dried and concentrated in vacuo to give the residue, which was purified by preparative HPLC on a GILSON 281 instrument fitted with a YMC-Actus Triart C18 (150*30 mm*5 um) using water and acetonitrile as the eluents. Mobile phase A: water (containing 0.1% TFA, v/v), mobile phase B:acetonitrile. Gradient: 5-25% B, 0-10 min; 100% B, 10.5-12.5 min; 5% B, 13-15 min to give the title compound. MS m/z: 534 (M+H)⁺; ¹HNMR (400 MHz, CDCl₃) δ: 7.88 (d, 1H, J=8.4 Hz), 7.46 (d, 1H, J=6.8 Hz), 7.24-7.32 (m, 1H), 7.20-7.27 (m, 2H), 7.08 (d, 1H, J=8.8 Hz), 6.84 (s, 1H), 6.77 (d, 1H, J=10.0 Hz), 5.15 (s, 2H), 4.44-4.47 (m, 2H), 3.98 (s, 1H), 3.48 (d, 1H, J=9.6 Hz), 3.20-3.30 (m, 2H), 2.98-3.02 (m, 1H), 2.83-2.85 (m, 1H), 2.36-2.37 (m, 4H), 1.87-1.93 (m, 2H), 1.33-1.65 (m, 5H), 0.99-1.02 (m, 1H).

Example 28

(1S,1aS,6aR)-4-((2-fluoro-5-(2-methyl-6-((tetrahydro-2H-pyran-4-yl)methoxy)pyridin-3-yl)benzyl)oxy)-1,1a,6,6a-tetrahydrocyclopropa[a]indene-1-carboxylic acid

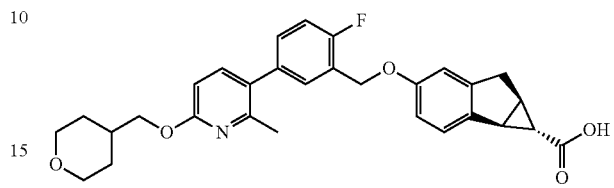

Step A. 5-bromo-6-methylpyridin-2-ol

3-Bromo-6-fluoro-2-methylpyridine (5 g, 0.021 mol) was added into HCl (6 mol/L, 40 mL), and the mixture was stirred, and refluxed for 2 hours. The product was detected by TLC. After the reaction was finished, the mixture was quenched with saturated aqueous NaHCO₃, filtered, and concentrated to afford the title compound.

Step B. 3-bromo-2-methyl-6-((tetrahydro-2H-pyran-4-yl)methoxy)pyridine

To a stirred solution of 5-bromo-6-methylpyridin-2-ol in toluene was added 4-bromomethyl-tetrahydro-[2H]-pyran (1 equivalent) and Ag₂CO₃ (2 equivalents). Then the mixture was heated to reflux overnight. TLC showed 5-bromo-6-methylpyridin-2-ol was consumed. The mixture was filtered and the filtrate was concentrated to afford crude product which was purified by preparative TLC (PE/EA=1/1) to give the title compound. MS m/z: 287 (M+H⁺).

Step C. (1S,1aS,6aR)-4-((2-fluoro-5-(2-methyl-6-((tetrahydro-2H-pyran-4-yl)methoxy)pyridin-3-yl)benzyl)oxy)-1,1a,6,6a-tetrahydrocyclopropa[a]indene-1-carboxylic acid, ethyl ester A microwave vessel charged with 3-bromo-2-methyl-6-((tetrahydro-2H-pyran-4-yl)methoxy)pyridine (1 mmol), 4-[2-fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester (1 mole-equivalent), PCy3 (0.1 mole-equivalent), Pd₂(dba)₃ (0.1 mole-equivalent) and K₂CO₃ (2.0 mole-equivalent) in dioxane (4 mL), H₂O (2 mL) was heated to 100° C. for 20 mins with microwave. LCMS showed the completion of the reaction. The vessel was cooled to 25° C. and the organic layer concentrated to afford a residue which was purified by Flash Chromatography on silica gel to give the title compound. MS m/z: 532 (M+H)⁺.

Step D. (1S,1aS,6aR)-4-((2-fluoro-5-(2-methyl-6-((tetrahydro-2H-pyran-4-yl)methoxy)pyridin-3-yl)benzyl)oxy)-1,1a,6,6a-tetrahydrocyclopropa[a]indene-1-carboxylic acid (1S,1aS,6aR)-4-((2-fluoro-5-(2-methyl-6-((tetrahydro-2H-pyran-4-yl)methoxy)pyridin-3-yl)benzyl)oxy)-1,1a,6,6a-tetrahydrocyclopropa[a]indene-1-carboxylic acid, ethyl ester was treated with aqueous lithium hydroxide according to the procedures described in Example 27, Step C to afford the title compound. MS m/z: 504 (M+H)+. ¹H NMR (400 MHz, CDCl₃) δ: 7.85-7.87 (d, 1H, J=8.8 Hz), 7.38-7.40 (d, 1H, J=6.8 Hz), 7.20-7.24 (m, 2H), 6.89-6.91 (d, 1H, J=8.8 Hz), 6.74-6.80 (m, 3H), 5.15 (s, 2H), 4.12-4.14 (d, 2H, J=6.4 Hz), 4.03-4.07 (dd, 2H, J₁=3.6 Hz, J₂=11.6 Hz), 3.44-3.50 (m, 2H), 3.24-3.30 (dd, 1H, J₁=6.4 Hz, J₂=18.4 Hz), 2.94-3.05 (m, 2H), 2.49-2.53 (m, 4H), 2.17-2.23 (m, 1H), 1.77-1.80 (d, 2H, J=11.2 Hz), 1.40-1.50 (m, 2H).

The following Examples 29 and 30 were prepared in a similar manner to Example 28 using the appropriate intermediates and commercially available starting materials.

Step B. (1S,1aS,6aR)-4-((2-fluoro-5-(6-(((3R,3aR, 6S,6aR)-6-hydroxyhexahydrofuro[3,2-b]furan-3-yl) oxy)-2-methylpyridin-3-yl)benzyl)oxy)-1,1a,6,6a-tetrahydrocyclopropa[a]indene-1-carboxylic acid, ethyl ester A solution of (3S,3aR,6R,6aR)-6-(5-bromo-6-methyl-pyridin-2-yloxy) hexahydrofuro[3,2-b]furan-3-ol (100 mg, 0.316 mmol), 4-[2-fluoro-5-(4,4,5,5-tetramethyl-[1,3,2]di-

| Ex. No. | Structure | Compound Name | MS observed [M + H]+ |
|---|---|---|---|
| 29 | 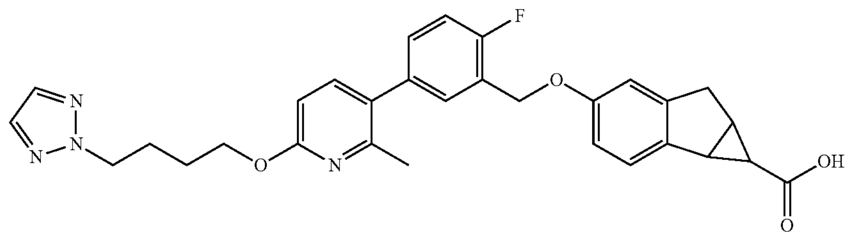 [SMILES: Cc1nc(OCCCCn2nccn2)ccc1-c1ccc(F)c(COc2ccc3c(c2)CC2C(C(=O)O)C32)c1] | 4-((5-(6-(4-(2H-1,2,3-triazol-2-yl)butoxy)-2-methyl-pyridin-3-yl)-2-fluorobenzyl)oxy)-1,1a,6,6a-tetrahydrocyclopropa[a]indene-1-carboxylic acid | 529 |
| 30 | 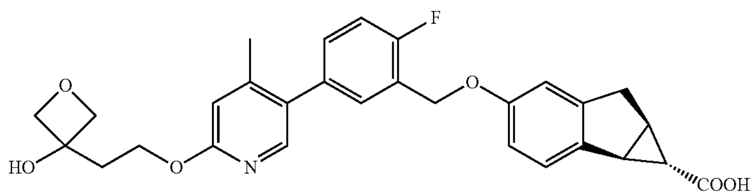 [SMILES: Cc1cc(OCCC2(O)COC2)ncc1-c1ccc(F)c(COc2ccc3c(c2)C[C@H]2[C@H](C(=O)O)[C@@H]32)c1] | (1S,1aS,6aR)-4-((2-fluoro-5-(6-(2-(3-hydroxyoxetan-3-yl)ethoxy)-4-methylpyridin-3-yl)benzyl)oxy)-1,1a,6,6a-tetrahydrocyclopropa[a]indene-1-carboxylic acid | 506 |

Example 31

(1S,1aS,6aR)-4-((2-fluoro-5-(6-(((3R,3aR,6S,6aR)-6-hydroxyhexahydrofuro[3,2-b]furan-3-yl)oxy)-2-methylpyridin-3-yl)benzyl)oxy)-1,1a,6,6a-tetrahydrocyclopropa[a]indene-1-carboxylic acid oxaborolan-2-yl)-benzyloxy]-1,1a,6,6a-tetrahydro-cyclo-propa[a]indene-1-carboxylic acid, ethyl ester from Example 10, Step D (171 mg, 0.38 mmol), Pd(dppf)Cl₂ (46 mg, 0.063 mmol) and K₂CO₃ (109 mg, 0.8 mmol) in HTF/H₂O (2 mL/0.4 mL) was heated to reflux for 11 h. The solvent was removed and the residue was purified to give the title compound. MS m/z: 562 (M+H)+.

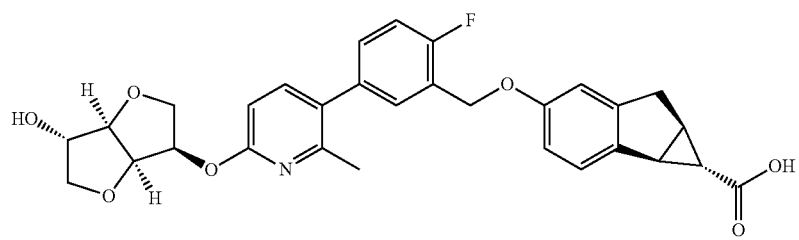 [SMILES: Cc1nc(O[C@@H]2CO[C@H]3[C@@H]2OC[C@@H]3O)ccc1-c1ccc(F)c(COc2ccc3c(c2)C[C@H]2[C@H](C(=O)O)[C@@H]32)c1]

Step A. (3S,3aR,6R,6aR)-6-(5-bromo-6-methylpyri-din-2-yloxy) hexahydrofuro[3,2-b]furan-3-ol To a solution of (3R,3aR,6S,6aR)-hexahydrofuro[3,2-b] furan-3,6-diol (also 1,4:3,6-dianhydro-D-glucitol) (200 mg, 1.37 mmol), and 3-bromo-6-fluoro-2-methylpyridine (312 mg, 1.64 mmol) in DMF (3 mL) was added NaH (110 mg, 2.74 mmol, 60% in mineral oil) and the reaction mixture was stirred at 25° C. for 1 h. The mixture was quenched with saturated NH₄Cl (3 mL), and extracted with EtOAc (3×30 mL). The organic phase was concentrated to give the title compound. MS m/z: 317 and 319 (M+H)+.

Step C. (1S,1aS,6aR)-4-((2-fluoro-5-(6-(((3R,3aR, 6S,6aR)-6-hydroxyhexahydrofuro[3,2-b]furan-3-yl) oxy)-2-methylpyridin-3-yl)benzyl)oxy)-1,1a,6,6a-tetrahydrocyclopropa[a]indene-1-carboxylic acid To a solution of (1S,1aS,6aR)-4-((2-fluoro-5-(6-(((3R, 3aR,6S,6aR)-6-hydroxyhexahydrofuro[3,2-b]furan-3-yl) oxy)-2-methylpyridin-3-yl)benzyl)oxy)-1,1a,6,6a-tetrahy-drocyclopropa[a]indene-1-carboxylic acid, ethyl ester (120 mg, 0.21 mmol) in CH₃OH and H₂O (2 mL/0.5 mL) was added LiOH.H₂O (25 mg, 0.6 mmol) and the mixture was heated to 40° C. for 2 h. The reaction mixture was concentrated in vacuo to give the residue, which was purified by prep-TLC to give the title compound. MS m/z: 534 (M+H)⁺; ¹H NMR (400 MHz, CDCl₃)¹H NMR (400 MHz, CDCl₃) δ: 7.30-7.45 (m, 2H), 7.18-7.30 (m, 2H), 7.06-7.03 (m, 1H), 6.77 (dd, 2H, J=2.4 and 14.0 Hz), 6.73 (d, 1H, J=8.4 Hz), 5.49 (dd, 1H, J=6.0 and 14.0 Hz), 5.03-5.12 (m, 3H), 4.54 (d, J=3.2 Hz), 4.37 (d, 1H, J=2.8 Hz), 4.16-4.23 (m, 1H), 3.97-4.06 (m, 1H), 3.86-3.93 (m, 1H), 3.73-3.85 (m, 1H), 3.20-3.30 (m, 1H), 2.94-3.05 (m, 2H), 2.46-2.50 (m, 1H), 2.32 (s, 3H), 1.18 (t, 1H, J=2.0 Hz).

Example 32

(1S,1aS,6aR)-4-((2-fluoro-5-(6-(3-(methylsulfonyl) propoxy)-4-(trifluoromethyl)pyridin-3-yl)benzyl) oxy)-1,1a,6,6a-tetrahydrocyclopropa[a]indene-1-carboxylic acid

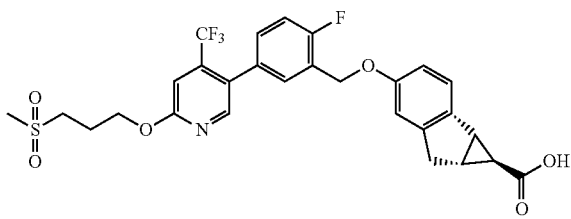

Step A. 2-(3-Methylsulfanyl-propoxy)-4-trifluoromethyl-pyridine

In a 250 mL round bottom flask, t-BuOK (9.3 g, 82.5 mmol) was added to a stirred mixture of 2-chloro-4-trifluoromethyl-pyridine (10 g, 55 mmol) and 3-methylsulfanyl-propan-1-ol (8.7 g, 82.5 mmol) in dry THF (80 mL). The mixture was allowed to stir at 100° C. overnight. After the mixture was cooled to room temperature. The mixture was filtered, and the filtrate was concentrated. The residue was purified by column chromatography on silica gel (PE/EA=5/1) to give the title compound. MS m/e (M+H⁺): 252.3.

Step B. 2-(3-Methanesulfonyl-propoxy)-4-trifluoromethyl-pyridine

In a 250 mL round bottom flask, m-CPBA (20 g, 93 mmol) was added portionwise to a stirred solution of 2-(3-methylsulfanyl-propoxy)-4-trifluoromethyl-pyridine (11.2 g, 44 mmol) in dry DCM (100 mL) at 0° C. The mixture was allowed to stir at r.t for 4 h. After being quenched by Na₂SO₃.aq, the mixture was extracted with ethyl acetate twice. The combined organic layer was washed with aq. Na₂CO₃, and brine, dried over anhydrous Na₂SO₄ and concentrated in vacuo. The residue was purified by column chromatography on silica gel (PE/EA=2/1) to afford the title compound. MS m/e (M+H⁺): 284.3.

Step C. 5-Bromo-2-(3-methanesulfonyl-propoxy)-4-trifluoromethyl-pyridine

In a 250 mL round bottom flask, Br₂ (18 mL, 0.35 mol) was added dropwise to a stirred solution of 2-(3-methanesulfonyl-propoxy)-4-trifluoromethyl-pyridine (5 g, 44 mmol) in AcOH (10 mL) at r.t. and the mixture was allowed to stir for 16 h at r.t. After being quenched by Na₂SO₃.aq and Na₂CO₃.aq, the mixture was extracted with ethyl acetate twice. The combined organic layer was washed with aq. Na₂CO₃, and brine, dried over anhydrous Na₂SO₄ and concentrated in vacuo. The residue was purified by column chromatography on silica gel (PE/EA=2/1) to afford the title compound.

Step D. 4-{2-Fluoro-5-[6-(3-methanesulfonyl-propoxy)-4-trifluoromethyl-pyridin-3-yl]-benzyloxy}-1,1a,6,6a-tetrahydro-cyclopropa[a]indene-1-carboxylic acid, ethyl ester A suspension of 5-bromo-2-(3-methanesulfonyl-propoxy)-4-trifluoromethyl-pyridine (500 g, 1.38 mmol), (1S,1aS,6aR)-4-hydroxy-1,1a,6,6a-tetrahydrocyclopropa[a]indene-1-carboxylic acid, ethyl ester from Reference Example 1 (686 g, 1.52 mmol), Pd(dppf)₂Cl₂ (100 mg, 0.138 mmol), K₃PO₄ (1.07 g, 4.14 mmol) and THF/H₂O (4:1, 15 mL) was heated at 100° C. for 30 min in a microwave system under N₂ protection. After that, the mixture was filtered; and the filtrate was partitioned with water (50 mL) and ethyl acetate (100 mL). The organic layer was washed with brine and dried over anhydrous sodium sulfate. After being concentrated in vacuo, the residue was purified by silica gel prep-TLC (DCM/MeOH=20/1) to afford the title compound. MS m/e (M+H⁺): 608.4.

Step E. (1S,1aS,6aR)-4-((2-fluoro-5-(6-(3-(methylsulfonyl)propoxy)-4-(trifluoromethyl)pyridin-3-yl) benzyl)oxy)-1,1a,6,6a-tetrahydrocyclopropa[a]indene-1-carboxylic acid The mixture of 4-{2-fluoro-5-[6-(3-methanesulfonyl-propoxy)-4-trifluoromethyl-pyridin-3-yl]-benzyloxy}-1,1a,6,6a-tetrahydro-cyclopropa[a]indene-1-carboxylic acid, ethyl ester (500 mg, 0.82 mmol) and LiOH (200 mg, 5.0 mmol) in THF/H₂O/MeOH (2:2:2 mL) was stirred at r.t for 2 hours; then the mixture was acidified to pH 5-6 by aq.HCl. The aqueous phase was twice extracted with ethyl acetate. The combined organic layers were washed with brine, dried over anhydrous Na₂SO₄ and concentrated in vacuo. The residue was purified by preparative HPLC to give the title compound. MS m/e (M+H⁺): 580.4; ¹HNMR (400 MHz, Methanol-d4) δ: 8.12 (s, 1H), 7.42~7.44 (d, 1H, J=6 Hz), 7.29~7.31 (m, 1H), 7.17~7.24 (m, 3H), 6.83 (s, 1H), 6.76~6.78 (d, 1H, J=8 Hz), 5.12 (s, 2H), 4.51~4.54 (t, 1H, J=6.4 Hz), 3.20~3.34 (m, 3H), 2.97~3.02 (t, 4H), 2.83~2.85 (d, 1H, J=5.6 Hz), 2.28~2.40 (m, 3H), 1.03~1.04 (t, 1H, J=2.4 Hz)

The following Examples 33-36 were prepared in a similar manner to Example 32 using the appropriate intermediates and commercially available starting materials.

| Ex. No. | Structure | Compound Name | MS observed [M + H]+ |
|---|---|---|---|
| 33 | 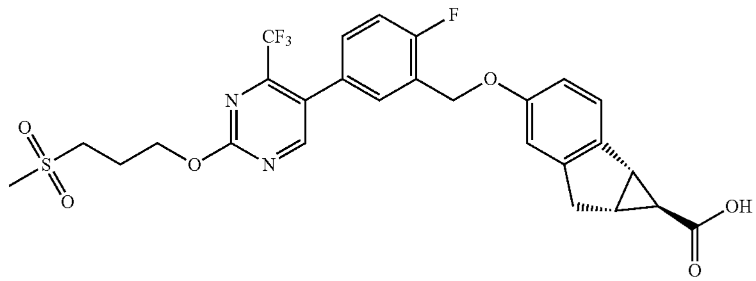 [SMILES: CS(=O)(=O)CCCOc1ncc(-c2ccc(F)c(COc3ccc4c(c3)C[C@H]3[C@H](C(=O)O)[C@@H]43)c2)c(C(F)(F)F)n1] | (1S,1aS,6aR)-4-((3-(2-methyl-6-(4-(methylsulfonyl)piperazin-1-yl)pyridin-3-yl)benzyl)oxy)-1,1a,6,6a-tetrahydrocyclopropa[a]indene-1-carboxylic acid | 581.3 |
| 34 | 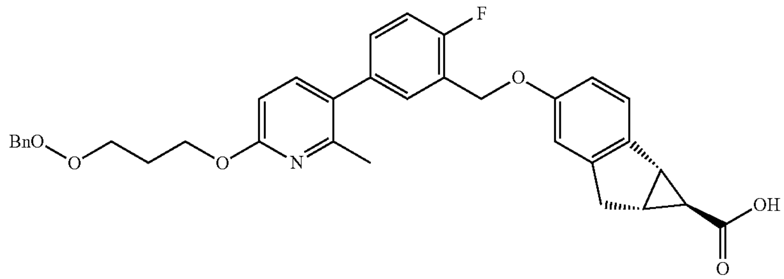 [SMILES: Cc1nc(OCCCOOCc2ccccc2)ccc1-c1ccc(F)c(COc2ccc3c(c2)C[C@H]2[C@H](C(=O)O)[C@@H]32)c1] | (1S,1aS,6aR)-4-((5-(6-(3-(benzyloxy)propoxy)-2-methylpyridin-3-yl)-2-fluorobenzyl)oxy)-1,1a,6,6a-tetrahydrocyclopropa[a]indene-1-carboxylic acid | 554.4 |
| 35 | 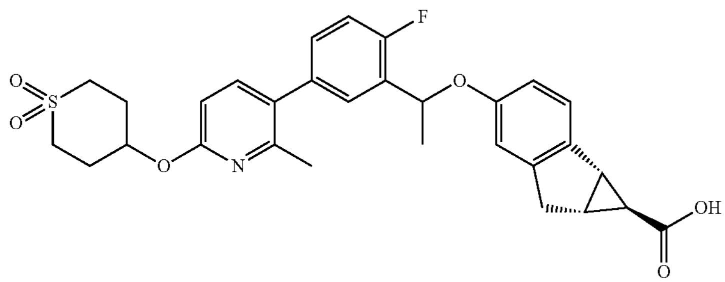 [SMILES: Cc1nc(OC2CCS(=O)(=O)CC2)ccc1-c1ccc(F)c(C(C)Oc2ccc3c(c2)C[C@H]2[C@H](C(=O)O)[C@@H]32)c1] | (1S,1aS,6aR)-4-(1-(5-(6-((1,1-dioxidotetrahydro-2H-thiopyran-4-yl)oxy)-2-methylpyridin-3-yl)-2-fluorophenyl)ethoxy)-1,1a,6,6a-tetrahydrocyclopropa[a]indene-1-carboxylic acid | 552.4 |
| 36 | 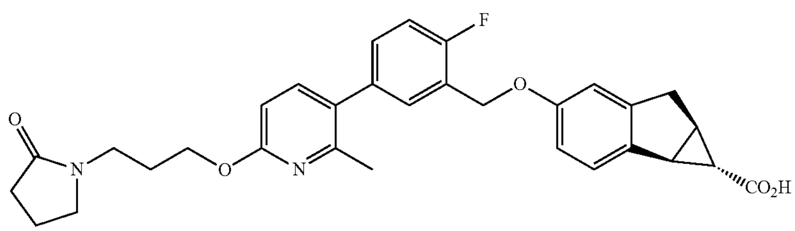 [SMILES: Cc1nc(OCCCN2CCCC2=O)ccc1-c1ccc(F)c(COc2ccc3c(c2)C[C@H]2[C@H](C(=O)O)[C@@H]32)c1] | (1S,1aS,6aR)-4-((2-fluoro-5-(2-methyl-6-(3-(2-oxopyrrolidin-1-yl)propoxy)pyridin-3-yl)benzyl)oxy)-1,1a,6,6a-tetrahydrocyclopropa[a]indene-1-carboxylic acid | 531.4 |

Example 37

(1S,1aS,6aR)-4-((2-fluoro-5-(6-(3-(1-hydroxycyclopropyl)propoxy)-2-methylpyridin-3-yl)benzyl)oxy)-1,1a,6,6a-tetrahydrocyclopropa[a]indene-1-carboxylic acid

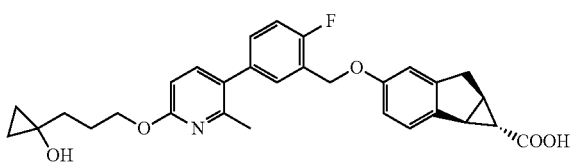 [SMILES: Cc1nc(OCCCC2(O)CC2)ccc1-c1ccc(F)c(COc2ccc3c(c2)C[C@H]2[C@H](C(=O)O)[C@@H]32)c1]

Step A. 5-Bromo-6-methyl-pyridin-2-ol

A solution of 3-bromo-6-fluoro-2-methyl-pyridine (4.3 g, 22.6 mmol) in HCl (20 mL)/H$_2$O (20 mL) was heated at 110° C. for 16 h. After cooling to room temperature, the resulting mixture was neutralized by aqueous solution of Na$_2$CO$_3$ to pH=7, and filtered to get the insoluble part, which was dried by an oven to give the title compound (crude).

Step B. 4-(5-Bromo-6-methyl-pyridin-2-yloxy)-butyric acid, ethyl ester

A mixture of 5-bromo-6-methyl-pyridin-2-ol (1.3 g, 6.9 mmol), 4-bromo-butyric acid ethyl ester (2.7 g, 13.8 mmol) and K$_2$CO$_3$ (2.8 g, 20.7 mmol) in DMF (20 mL) was heated at 110° C. under a dry N$_2$ atmosphere for 16 h. After cooling, the mixture was diluted with 200 mL of H$_2$O, and twice extracted with ethyl acetate. The combined organic phase was washed with brine, dried over anhydrous Na$_2$SO$_4$ and concentrated. The residue was purified by flash column chromatography on silica gel (EA/PE=1/10) to give the title compound.

Step C. 1-[3-(5-Bromo-6-methyl-pyridin-2-yloxy)-propyl]-cyclopropanol

To a solution of 4-(5-bromo-6-methyl-pyridin-2-yloxy)-butyric acid, ethyl ester (500 mg, 1.65 mmol) in dry THF (20 mL) was added Ti(OPr)$_4$ (468 mg, 3.3 mmol) at 0° C. and stirred under N$_2$ atmosphere for 20 min. EtMgBr was added dropwise and the mixture was allowed to stir at rt for 6 h.

was purified by preparative HPLC to afford the title compound. MS m/e (M+H$^+$): 504.2; $^1$H-NMR (400 MHz, Methanol-d4) δ: 7.78~7.80 (d, 1H, J=8.4 Hz), 7.43~7.44 (d, 1H, J=11.2 Hz), 7.32 (s, 1H), 7.20~7.25 (m, 2H), 6.96~6.98 (d, 1H, J=8.4 Hz), 6.83 (s, 1H), 6.76~6.78 (d, 1H, J=8 Hz), 5.14 (s, 2H), 4.33~4.36 (t, 1H, J=6.4 Hz), 3.01~3.23 (m, 1H), 2.97~3.01 (d, 1H, J=18.4 Hz), 2.83~2.84 (d, 1H, J=5.2 Hz), 2.65~2.69 (t, 2H, J=7.2 Hz), 2.47~2.53 (m, 2H), 2.34~2.37 (m, 4H), 2.05~2.1 (m, 2H), 1.01~1.04 (t, 1H, J=7.2 Hz)

The following Example 38 was prepared in a similar manner to Example 37 using the appropriate intermediates and commercially available starting materials.

| Ex. No. | Structure | Compound Name | MS observed [M + H]+ |
|---|---|---|---|
| 38 | 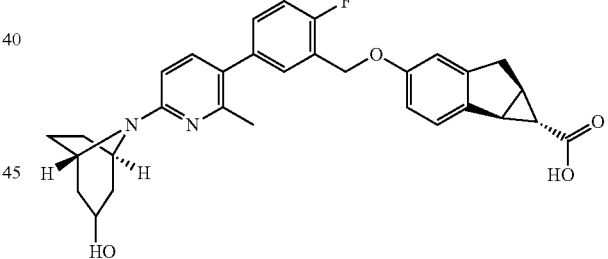 | (1S,1aS,6aR)-4-((2-fluoro-5-(6-((4-(2-hydroxypropan-2-yl)cyclohexyl)oxy)-2-methylpyridin-3-yl)benzyl)oxy)-1,1a,6,6a-tetrahydro-cyclopropa[a]indene-1-carboxylic acid | 546.4 |

After being quenched with HCl.aq (1 mol/L), the mixture was twice extracted with ethyl acetate. The combined organic phase was washed with brine, dried over anhydrous Na$_2$SO$_4$ and concentrated. The residue was purified by chromatography on silica gel (PE/EA=8/1) to give the title compound.

Step D. 4-(2-Fluoro-5-{6-[3-(1-hydroxy-cyclopropyl)-propoxy]-2-methyl-pyridin-3-yl}-benzyloxy)-1,1a,6,6a-tetrahydro-cyclopropa[a]indene-1-carboxylic acid, ethyl ester A mixture of 1-[3-(5-bromo-6-methyl-pyridin-2-yloxy)-propyl]-cyclopropanol (130 mg, 0.45 mmol), (1S,1aS,6aR)-4-hydroxy-1,1a,6,6a-tetrahydrocyclopropa[a]indene-1-carboxylic acid, ethyl ester from Reference Example 1 (205 mg, 0.45 mmol), K$_3$PO$_4$ (351 mg, 1.35 mmol) and Pd(dppf)Cl$_2$ (37 mg, 0.045 mmol) in THF (4 mL) and H$_2$O (1 mL) was heated at 100° C. in a microwave system under N$_2$ atmosphere for 30 min. After cooling, the mixture was twice extracted with ethyl acetate. The combined organic phase was washed with brine, dried over anhydrous Na$_2$SO$_4$ and concentrated to give the title compound as a crude product. MS m/e (M+H$^+$): 532.2

Step E. (1S,1aS,6aR)-4-((2-fluoro-5-(6-(3-(1-hydroxycyclopropyl)propoxy)-2-methylpyridin-3-yl)benzyl)oxy)-1,1a,6,6a-tetrahydrocyclopropa[a]indene-1-carboxylic acid The mixture of 4-(2-fluoro-5-{6-[3-(1-hydroxy-cyclopropyl)-propoxy]-2-methyl-pyridin-3-yl}-benzyloxy)-1,1a,6,6a-tetrahydro-cyclopropa[a]indene-1-carboxylic acid, ethyl ester (160 mg, 0.3 mmol) and LiOH (120 mg, 3 mmol) in THF/H$_2$O/MeOH (3:3:3 mL) was stirred at r.t for 2 hours. The mixture was acidified to pH 5-6 by aq. HCl. The aqueous phase was extracted with ethyl acetate twice. The combined organic layer was washed by brine, dried over anhydrous Na$_2$SO$_4$ and concentrated in vacuo. The residue Example 39

(1S,1aS,6aR)-4-((2-fluoro-5-(6-((1R,5S)-3-hydroxy-8-azabicyclo[3.2.1]octan-8-yl)-2-methylpyridin-3-yl)benzyl)oxy)-1,1a,6,6a-tetrahydrocyclopropa[a]indene-1-carboxylic acid Step A. 8-(5-Bromo-6-methyl-pyridin-2-yl)-8-aza-bicyclo[3.2.1]octan-3-ol The mixture of 3-bromo-6-fluoro-2-methyl-pyridine (1.35 g, 7 mmol), 8-aza-bicyclo[3.2.1]octan-3-ol (1.720 g, 1.5 eq) and K$_2$CO$_3$ (4 g, 4 eq) in NMP (20 mL) was heated at 150° C. for 3 h. After being cooled to rt, the mixture was diluted with H$_2$O, and extracted with ethyl acetate (15 ml×3). The combined extracts were washed with water and brine, dried (Na$_2$SO$_4$), filtered and evaporated. The residue was purified by flash chromatography on silica gel (EA/PE=10%) to afford the title compound. MS (ESI) m/e (M+H$^+$): 297.

Step B. 4-{2-Fluoro-5-[6-(3-hydroxy-8-aza-bicyclo[3.2.1]oct-8-yl)-2-methyl-pyridin-3-yl]-benzyloxy}-1,1a,6,6a-tetrahydro-cyclopropa[a]indene-1-carboxylic acid ethyl ester The mixture of 8-(5-bromo-6-methyl-pyridin-2-yl)-8-aza-bicyclo[3.2.1]octan-3-ol (300 mg, 1 mmol), 4-[2-fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester from Example 10, Step D (590 mg, 1.3 eq), Pd$_2$(dba)$_3$ (90 mg, 0.1 eq), S-Phos (80 mg, 0.2 eq) and K$_3$PO$_4$ (640 mg, 3 eq) in THF/H$_2$O (8 ml/2 ml) was heated at 100° C. overnight. The mixture was cooled to rt, and concentrated under reduced pressure. The residue was purified by flash chromatography on silica gel (EA/PE=30%) to afford the title compound. MS (ESI) m/e (M+H$^+$): 543.

Step C. (1S,1aS,6aR)-4-((2-fluoro-5-(6-((1R,5S)-3-hydroxy-8-azabicyclo[3.2.1]octan-8-yl)-2-methyl-pyridin-3-yl)benzyl)oxy)-1,1a,6,6a-tetrahydrocyclopropa[a]indene-1-carboxylic acid The mixture of 4-{2-fluoro-5-[6-(3-hydroxy-8-aza-bicyclo[3.2.1]oct-8-yl)-2-methyl-pyridin-3-yl]-benzyloxy}-1,1a,6,6a-tetrahydro-cyclopropa[a]indene-1-carboxylic acid, ethyl ester (54 mg, 0.1 mmol) and NaOH (23 mg, 1 mmol) in H$_2$O/MeOH (1:3 mL) was stirred at r.t for 2 hours. The mixture was acidified to pH 5-6 by aq.HCl. The aqueous phase was extracted with ethyl acetate twice. The combined organic layer was washed by brine, dried over anhydrous Na$_2$SO$_4$ and concentrated in vacuo. The residue was purified by prep.HPLC to yield the title compound. MS m/e (M+H$^+$): 514.4; $^1$H NMR (400 MHz, CDCl$_3$-d$_4$) δ=7.31 (d, J=1.6 HZ, 1H), 7.29-7.14 (m, 3H), 7.13 (t, J=2.8 HZ, 1H), 6.73 (s, 1H), 6.70 (d, J=4.0 HZ, 1H), 6.35 (d, J=8.0 HZ, 1H), 5.22 (s, 2H), 5.04 (s, 2H), 4.44 (s, 1H), 4.07-4.02 (m, 1H), 3.21-3.15 (m, 1H), 2.94 (d, J=15.6 HZ, 1H), 2.88 (d, J=6.0 HZ, 1H), 2.42-2.39 (m, 1H), 2.22 (s, 6H), 2.21-2.18 (m, 2H), 1.62 (d, J=14.4 HZ, 2H), 1.11 (s, 1H).

The following Examples 40-46 was prepared in a similar manner to Example 39 using the appropriate intermediates and commercially available starting materials.

| Ex. No. | Structure | Compound Name | MS observed [M + H]+ |
| --- | --- | --- | --- |
| 40 | 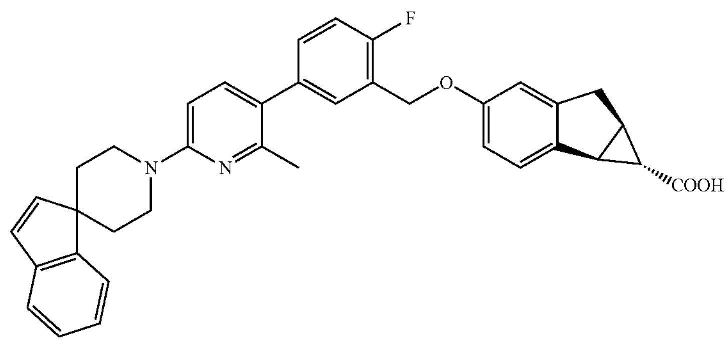 [SMILES: Cc1nc(N2CCC3(C=Cc4ccccc43)CC2)ccc1-c1ccc(F)c(COc2ccc3c(c2)C[C@H]2[C@H](C(=O)O)[C@@H]32)c1] | (1S,1aS,6aR)-4-((2,6-difluoro-3-(2-methyl-6-(spiro[indene-1,4'-piperidin]-1'-yl)pyridin-3-yl)benzyl)oxy)-1,1a,6,6a-tetrahydrocyclopropa[a]indene-1-carboxylic acid | 573.5 |
| 41 | 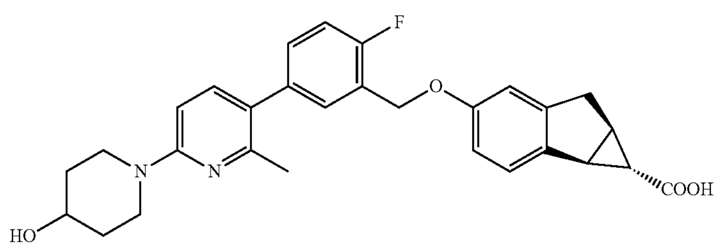 [SMILES: Cc1nc(N2CCC(O)CC2)ccc1-c1ccc(F)c(COc2ccc3c(c2)C[C@H]2[C@H](C(=O)O)[C@@H]32)c1] | (1S,1aS,6aR)-4-((2-fluoro-5-(6-(4-hydroxypiperidin-1-yl)-2-methylpyridin-3-yl)benzyl)oxy)-1,1a,6,6a-tetrahydrocyclopropa[a]indene-1-carboxylic acid | 489.4 |
| 42 | 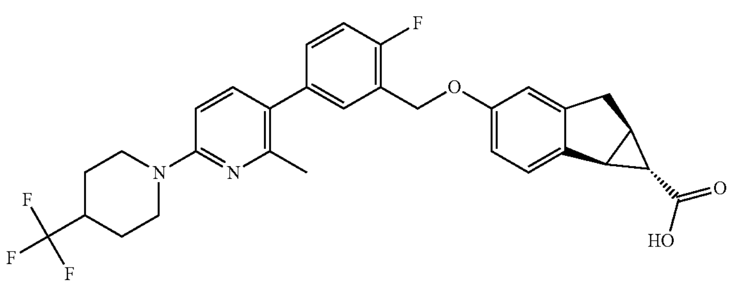 [SMILES: Cc1nc(N2CCC(C(F)(F)F)CC2)ccc1-c1ccc(F)c(COc2ccc3c(c2)C[C@H]2[C@H](C(=O)O)[C@@H]32)c1] | (1S,1aS,6aR)-4-((2-fluoro-5-(2-methyl-6-(4-(trifluoromethyl)piperidin-1-yl)pyridin-3-yl)benzyl)oxy)-1,1a,6,6a-tetrahydrocyclopropa[a]indene-1-carboxylic acid | 541.0 |

| Ex. No. | Structure | Compound Name | MS observed [M + H]+ |
|---|---|---|---|
| 43 | 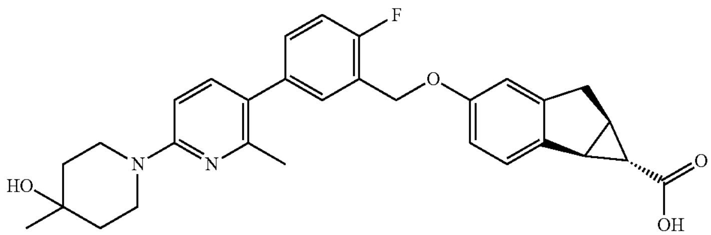 [SMILES: Cc1nc(N2CCC(C)(O)CC2)ccc1-c1ccc(F)c(COc2ccc3c(c2)C[C@H]2[C@H](C(=O)O)[C@@H]32)c1] | (1S,1aS,6aR)-4-((2-fluoro-5-(6-(4-hydroxy-4-methylpiperidin-1-yl)-2-methylpyridin-3-yl)benzyl)oxy)-1,1a,6,6a-tetrahydrocyclopropa[a]indene-1-carboxylic acid | 503.4 |
| 44 | 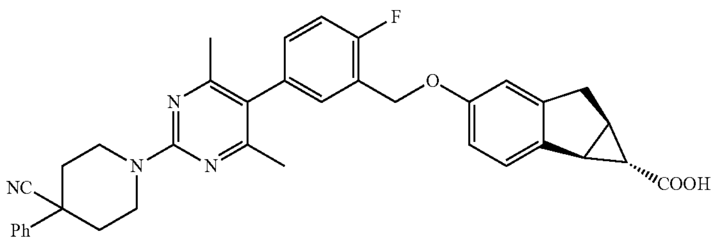 [SMILES: Cc1nc(N2CCC(C#N)(c3ccccc3)CC2)nc(C)c1-c1ccc(F)c(COc2ccc3c(c2)C[C@H]2[C@H](C(=O)O)[C@@H]32)c1] | (1S,1aS,6aR)-4-((5-(2-(4-cyano-4-phenylpiperidin-1-yl)-4,6-dimethylpyrimidin-5-yl)-2-fluorobenzyl)oxy)-1,1a,6,6a-tetrahydrocyclopropa[a]indene-1-carboxylic acid | 589.5 |
| 45 | 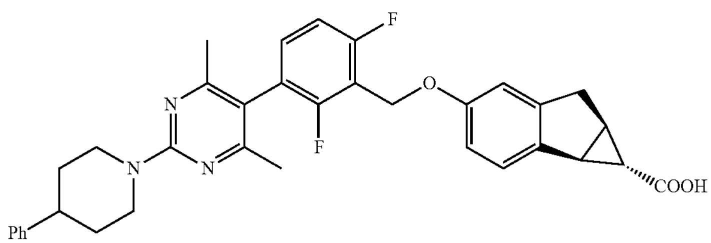 [SMILES: Cc1nc(N2CCC(c3ccccc3)CC2)nc(C)c1-c1ccc(F)c(COc2ccc3c(c2)C[C@H]2[C@H](C(=O)O)[C@@H]32)c1F] | (1S,1aS,6aR)-4-((3-(4,6-dimethyl-2-(4-phenylpiperidin-1-yl)pyrimidin-5-yl)-2,6-difluorobenzyl)oxy)-1,1a,6,6a-tetrahydrocyclopropa[a]indene-1-carboxylic acid | 582.5 |
| 46 | 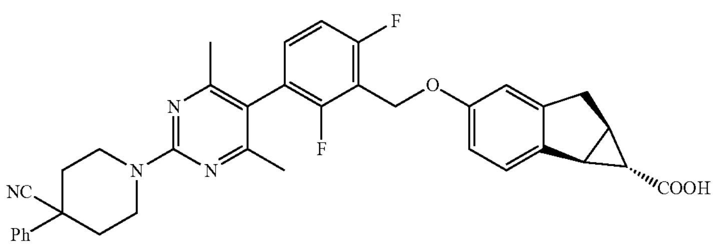 [SMILES: Cc1nc(N2CCC(C#N)(c3ccccc3)CC2)nc(C)c1-c1ccc(F)c(COc2ccc3c(c2)C[C@H]2[C@H](C(=O)O)[C@@H]32)c1F] | (1S,1aS,6aR)-4-((3-(2-(4-cyano-4-phenylpiperidin-1-yl)-4,6-dimethylpyrimidin-5-yl)-2,6-difluorobenzyl)oxy)-1,1a,6,6a-tetrahydrocyclopropa[a]indene-1-carboxylic acid | 607.5 |

Example 47

(1S,1aS,6aR)-4-((2-fluoro-5-(2-methyl-6-(3-(methylsulfonamidomethyl)pyrrolidin-1-yl)pyridin-3-yl)benzyl)oxy)-1,1a,6,6a-tetrahydrocyclopropa[a]indene-1-carboxylic acid

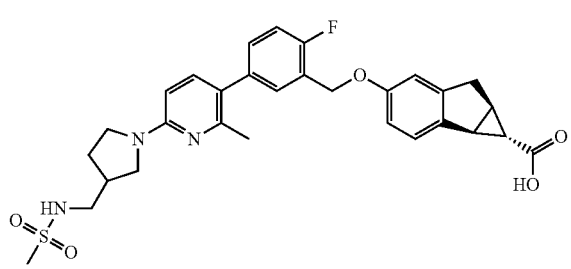 [SMILES: Cc1nc(N2CCC(CNS(C)(=O)=O)C2)ccc1-c1ccc(F)c(COc2ccc3c(c2)C[C@H]2[C@H](C(=O)O)[C@@H]32)c1]

Step A. [1-(5-Bromo-6-methyl-pyridin-2-yl)-pyrrolidin-3-ylmethyl]-carbamic acid tert-butyl ester To a solution of pyrrolidin-3-yl-methyl-carbamic acid, tert-butyl ester (500 mg, 2.63 mmol) and 3-bromo-6-fluoro-2-methyl-pyridine (790 mg, 3.95 mmol) in NMP (5 mL) was added $K_2CO_3$ (1.09 g, 7.89 mmol) and the mixture was stirred at 130° C. for 6 hrs. The mixture was filtered and partitioned between ethyl acetate and brine. The ethyl acetate layer was dried, then concentrated and the residue was purified by silica gel chromatography column (PE/EA=8/1) to give the title compound. MS m/e (M+H+): 370.1.

Step B. [1-(5-bromo-6-methyl-pyridin-2-yl)-pyrrolidin-3-yl]methylamine

To a solution of [1-(5-bromo-6-methyl-pyridin-2-yl)-pyrrolidin-3-ylmethyl]-carbamic acid, tert-butyl ester (0.6 mg, 1.63 mmol) in DCM (10 mL) was added TFA (5 mL) and the mixture was stirred at r.t. for 3 hrs. The mixture was concentrated and the residue was partitioned by DCM and Na₂CO₃aq. The DCM layer was concentrated to give the title compound. MS m/e (M+H⁺): 270.1.

Step C. N-[1-(5-Bromo-6-methyl-pyridin-2-yl)-pyrrolidin-3-ylmethyl]-methanesulfonamide To a solution of [1-(5-bromo-6-methyl-pyridin-2-yl)-pyrrolidin-3-yl]methylamine (600 mg, 2.00 mmol, crude) and MsCl (310 mg, 2.7 mmol) in DCM (10 mL) was added Et₃N (670 mg, 6.7 mmol). The mixture was then stirred at r.t overnight. The mixture was separated between ethyl acetate and brine and the ethyl acetate layer was washed with brine, dried over anhydrous Na₂SO₄, concentrated and the residue was purified by column chromatography on silica gel (PE/EA=8/1) to give the title compound. MS m/e (M+H⁺): 348.0.

Step D. 4-(2-Fluoro-5-{6-[3-(methanesulfonylamino-methyl)-pyrrolidin-1-yl]-2-methyl-pyridin-3-yl}-benzyloxy)-1,1a,6,6a-tetrahydro-cyclopropa[a]indene-1-carboxylic acid, ethyl ester To a solution of N-[1-(5-bromo-6-methyl-pyridin-2-yl)-pyrrolidin-3-ylmethyl]-methanesulfonamide (50 mg, 143 umol) and 4-[2-fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester from Example 10, Step D (71 mg, 157 umol) and S-phos (15 mg) in THF (3 mL) was added K₃PO₄ (91 mg, 0.43 mmol), Pd₂(dba)₃ (15 mg) and water (1 mL). The mixture was then stirred at 100° C. overnight under N₂ atmosphere. The mixture was filtered and concentrated to give the title compound (crude). MS m/e (M+H⁺): 594.2

Step E. (1S,1aS,6aR)-4-((2-fluoro-5-(2-methyl-6-(3-(methylsulfonamidomethyl)pyrrolidin-1-yl)pyridin-3-yl)benzyl)oxy)-1,1a,6,6a-tetrahydrocyclopropa[a]indene-1-carboxylic acid The mixture of 4-(2-fluoro-5-{6-[3-(methanesulfonylamino-methyl)-pyrrolidin-1-yl]-2-methyl-pyridin-3-yl}-benzyloxy)-1,1a,6,6a-tetrahydro-cyclopropa[a]indene-1-carboxylic acid, ethyl ester (50 mg, crude, 84 umol) and NaOH (1 mL, 1 N) in MeOH (3 mL) was stirred at r.t for 2 hours. Then the mixture was acidified to pH 5-6, extracted with ethyl acetate, washed with brine, dried over anhydrous Na₂SO₄ concentrated and then the residue was purified by preparative HPLC to afford the title compound. MS m/e (M+H⁺): 566.2; ¹H-NMR (400 MHz, methanol-d₄) δ: 7.81 (d, J=9.6 Hz, 1H), 7.45-7.43 (m, 1H), 7.37-7.33 (m, 1H), 7.28-7.22 (m, 2H), 6.96 (d, J=9.2 Hz, 1H), 6.84 (s, 1H), 6.76 (d, J=8.0 Hz, 1H), 5.15 (s, 2H), 3.82-3.74 (m, 2H), 3.67-3.65 (m, 1H), 3.54-3.50 (m, 1H), 3.25-3.16 (m, 3H), 3.01 (s, 1H), 3.00 (s, 3H), 2.83 (d, J=6.4 Hz, 1H), 2.41-2.28 (m, 5H), 2.02-1.97 (m, 1H), 1.03-1.02 (m, 1H).

The following Examples 48 and 49 were prepared in a similar manner to Example 47 using the appropriate intermediates and commercially available starting materials.

| Ex. No. | Structure | Compound Name | MS observed [M + H]+ |
|---|---|---|---|
| 48 | 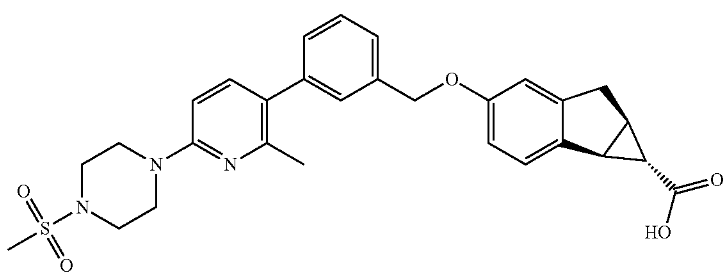 [SMILES: Cc1nc(N2CCN(S(C)(=O)=O)CC2)ccc1-c1cccc(COc2ccc3c(c2)C[C@H]2[C@H](C(=O)O)[C@@H]32)c1] | (1S,1aS,6aR)-4-((2-fluoro-5-(2-(3-(methylsulfonyl)propoxy)-4-(trifluoromethyl)pyrimidin-5-yl)benzyl)oxy)-1,1a,6,6a-tetrahydrocyclopropa[a]indene-1-carboxylic acid | 534.4 |
| 49 | 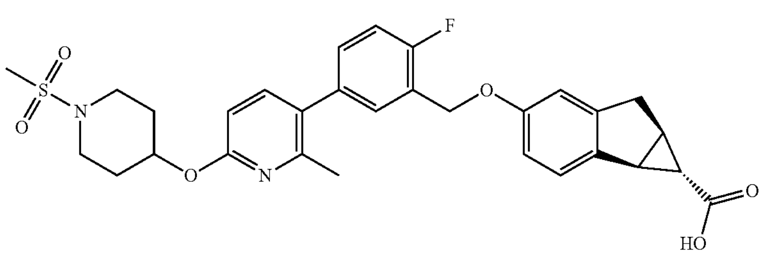 [SMILES: Cc1nc(OC2CCN(S(C)(=O)=O)CC2)ccc1-c1ccc(F)c(COc2ccc3c(c2)C[C@H]2[C@H](C(=O)O)[C@@H]32)c1] | (1S,1aS,6aR)-4-((2-fluoro-5-(2-methyl-6-((1-(methylsulfonyl)piperidin-4-yl)oxy)pyridin-3-yl)benzyl)oxy)-1,1a,6,6a-tetrahydrocyclopropa[a]indene-1-carboxylic acid | 567.4 |

Example 50

(1S,1aS,6aR)-4-((2-fluoro-5-(2-methyl-6-(4-((methylsulfonyl)methyl)piperidin-1-yl)pyridine-3-yl)benzyl)oxy)-1,1a,6,6a-tetrahydrocyclopropa[a]indene-1-carboxylic acid

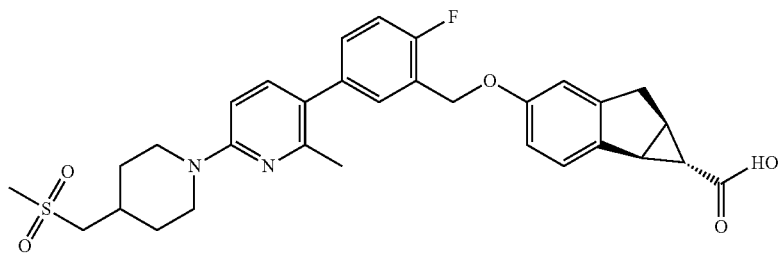 [SMILES: Cc1nc(N2CCC(CS(C)(=O)=O)CC2)ccc1-c1ccc(F)c(COc2ccc3c(c2)C[C@H]2[C@H](C(=O)O)[C@@H]32)c1]

Step A. 4-((methylsulfonyloxy)methyl)piperidine-1-carboxylic acid, tert-butyl ester To a stirred solution of 4-hydroxymethyl-piperidine-1-carboxylic acid, tert-butyl ester (500 mg, 2.32 mmol) in DCM (10 ml) was added triethylamine (352 mg, 3.48 mmol), and then methanesulfonyl chloride (319 mg, 215 mmol) was added dropwise at 0° C. The reaction mixture was stirred at RT for 1 h, and then diluted with DCM (50 mL). The organic layer was washed by water (20 mL), and diluted with HCl solution and brine, dried over Na$_2$SO$_4$, and concentrated to give the title compound (crude).

Step B. 4-(methylthiomethyl)piperidine-1-carboxylic acid, tert-butyl ester

To a stirred solution of 4-((methylsulfonyloxy)methyl)piperidine-1-carboxylic acid, tert-butyl ester (350 mg, 1.19 mmol) in MeOH (15 mL) was added sodium methanethiolate (209 mg, 2.98 mmol). The reaction mixture was stirred at 60° C. for 1 h. Then the reaction mixture was cooled to RT, diluted with ethyl acetate (100 mL). The organic phase was washed with water and brine, dried over Na$_2$SO$_4$, and concentrated to afford the title compound (crude).

Step C. 4-(methylsulfonylmethyl)piperidine-1-carboxylic acid, tert-butyl ester To a solution of 4-(methylthiomethyl)piperidine-1-carboxylic acid, tert-butyl ester (280 mg, 1.14 mmol) in dry DCM (10 mL) was added m-CPBA (85%, 463 mg, 2.28 mmol). The reaction mixture was stirred at RT for 2 h. The mixture was diluted with DCM (50 mL), washed with saturated Na$_2$SO$_3$ solution (20 mL), aq. NaHCO$_3$ (20 mL) solution, and brine (20 mL), and then dried over Na$_2$SO$_4$, concentrated to yield the title compound (crude).

Step D. 4-(methylsulfonylmethyl)piperidine

To a solution of 4-(methylsulfonylmethylmethylsulfonylmethyl)piperidine-1-carboxylic acid, tert-butyl ester (316 mg, 1.15 mmol) in DCM (2 mL) was added TFA (2 mL) and the reaction mixture was stirred at RT for 30 mins. The mixture was concentrated to give the title compound (crude).

Step E. 3-bromo-2-methyl-6-(4-(methylsulfonylmethyl)piperidin-1-yl)pyridine

To a solution of 4-(methylsulfonylmethyl)piperidine, TFA salt (150 mg, 515 μmop in NMP (2 mL) was added K$_2$CO$_3$ (213 mg, 1.54 mmol) and 3-bromo-6-fluoro-2-methylpyridine (98 mg, 515 μmol). The reaction mixture was stirred at 100° C. overnight. The reaction mixture was diluted with ethyl acetate (50 mL), washed with water (3×10 mL), and brine (20 mL), dried over Na$_2$SO$_4$, and concentrated to afford crude product. Purification by preparative TLC gave the title compound. MS m/e (M+H$^+$) 347, 349.

Step F. (1S,1aS,6aR)-4-((2-fluoro-5-(2-methyl-6-(4-((methylsulfonyl)methyl)piperidin-1-yl)pyridin-3-yl)benzyl)oxy)-1,1a,6,6a-tetrahydrocyclopropa[a]indene-1-carboxylic acid, ethyl ester A 40 mL bottle was charged with 3-bromo-2-methyl-6-(4-(methylsulfonylmethyl)piperidin-1-yl)pyridine (25 mg, 72 μmol), 4-[2-fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester from Example 10, Step D (32 mg, 72 μmol), Na$_2$CO$_3$ (15 mg, 144 μmol), dioxane (2 mL), H$_2$O (0.5 mL), and PdCl$_2$(dppf)CH$_2$Cl$_2$ (3 mg, 3.6 μmol). The bottle was placed on a 100° C. shaker overnight. After cooling to ambient temperature, the mixture was diluted with ethyl acetate. The organic layer was washed with brine and concentrated to yield the title compound (crude). MS (ESI) m/e (M+H$^+$) 593.2.

Step G. (1S,1aS,6aR)-4-((2-fluoro-5-(2-methyl-6-(4-((methylsulfonyl)methyl)piperidin-1-yl)pyridine-3-yl)benzyl)oxy)-1,1a,6,6a-tetrahydrocyclopropa[a]indene-1-carboxylic acid A mixture of (1S,1aS,6aR)-4-((2-fluoro-5-(2-methyl-6-(4-((methylsulfonyl)methyl)piperidin-1-yl)pyridin-3-yl)benzyl)oxy)-1,1a,6,6a-tetrahydrocyclopropa[a]indene-1-carboxylic acid, ethyl ester (40 mg, 67 μmol) in THF (2 mL) in EtOH (1 mL) was added water (1 mL), and LiOH (16 mg, 674 μmop. The reaction mixture was stirred at 50° C. for 4 h. After cooling to ambient temperature, the pH was adjusted to 4 with HCl (1N) and the reaction mixture was twice extracted by ethyl acetate. The combined organic layer was washed with brine, dried over Na$_2$SO$_4$, and concentrated; the residue was purified by prep-HPLC to give the title compound. MS m/e (M+H$^+$) 565.5; $^1$H NMR (400 MHz, methanol-d$_4$) δ: 7.83 (d, J=8.8 Hz, 1H), 7.44 (d, J=6.0 Hz, 1H), 7.34 (brs, 1H), 7.28-7.21 (m, 3H), 6.83 (s, 1H), 6.76 (d, J=8.0 Hz, 1H), 5.14 (s, 2H), 4.25 (d, J=12.4 Hz 2H), 3.35-3.33 (m, 5H), 3.00 (s, 3H), 2.98 (d, J=19.6 Hz, 1H), 2.83 (d, J=5.6 Hz, 1H), 2.40-2.37 (m, 5H), 2.15 (d, J=12.4 Hz, 2H), 1.58-1.55 (m, 2H), 1.02 (s, 1H).

Example 51

(1S,1aS,6aR)-4-((2-fluoro-5-(2-methyl-6-(3-(methylsulfonyl)azetidin-1-yl)pyridin-3-yl)benzyl)oxy)-1,1a,6,6a-tetrahydrocyclopropa[a]indene-1-carboxylic acid

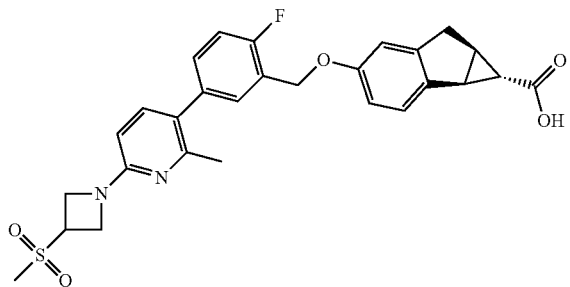 [SMILES: Cc1nc(N2CC(S(C)(=O)=O)C2)ccc1-c1ccc(F)c(COc2ccc3c(c2)C[C@H]2[C@H](C(=O)O)[C@@H]32)c1]

Step A.
3-(methylsulfonyloxy)azetidine-1-carboxylic acid, tert-butyl ester

To a stirred solution of 3-hydroxy-azetidine-1-carboxylic acid, tert-butyl ester (1.0 g, 5.77 mmol) in DCM (15 ml) was added triethylamine (876 mg, 8.66 mmol), and then methanesulfonyl chloride (793 mg, 6.93 mmol) was added dropwise at 0° C. The reaction mixture was stirred at RT overnight, and then diluted with DCM (50 mL). The organic layer was washed with water (20 mL), diluted HCl solution and brine, dried over Na$_2$SO$_4$, and concentrated to afford the title compound (crude).

Step B. 3-(methylthio)azetidine-1-carboxylic acid, tert-butyl ester

A 40 ml bottle was charged with 3-(methylsulfonyloxy)azetidine-1-carboxylic acid, tert-butyl ester (600 mg, 2.39 mmol), EtOH (3 mL), and sodium methanethiolate (251 mg, 3.58 mmol), the bottle was place on a 100° C. shaker for 1 h, monitored by TLC (PE/EA=2/1). Then the reaction mixture was cooled to RT, diluted with ethyl acetate (100 mL). The organic phase was washed with water and brine, dried over Na$_2$SO$_4$, concentrated to yield the title compound (crude).

Step C. 3-(methylthio)azetidine

To a solution of 3-(methylthio)azetidine-1-carboxylic acid, tert-butyl ester (500 mg, 2.46 mmol) in DCM (2 mL) was added TFA (2 mL), the reaction mixture was stirred at RT for 30 mins. The mixture was concentrated to afford crude 3-(methylthio)azetidine as a trifluoroacetic acid salt which was used to the next step without further purification.

Step D. 3-bromo-2-methyl-6-(3-(methylthio)azetidin-1-yl)pyridine

To a solution of 3-(methylthio)azetidine, TFA salt (548 mg, crude, 515 μmol) in NMP (4 mL) was added TEA (852 mg, 8.42 mmol), and 3-bromo-6-fluoro-2-methylpyridine (400 mg, 2.11 mmol). The reaction mixture was stirred at 120° C. under nitrogen atmosphere overnight. The reaction mixture was diluted with ethyl acetate (50 mL), washed with water (10 mL×3) and brine (20 mL), dried over Na$_2$SO$_4$, and concentrated to get the crude product which was purified by silica gel preparative TLC to give the title compound.

Step E. 3-bromo-2-methyl-6-(3-(methylsulfonyl)azetidin-1-yl)pyridine

To an ice cooled solution of 3-bromo-2-methyl-6-(3-(methylthio)azetidin-1-yl)pyridine (60 mg, 219.6 μmol) in dry DCM (3 mL) was added m-CPBA (85%, 89 mg, 439 μmol) in portions. The reaction mixture was stirred at 0° C. for 1 h. The mixture was diluted with DCM (50 mL), washed with saturated Na$_2$SO$_3$ solution (20 mL), aq.NaHCO$_3$ (20 mL) solution and brine (20 mL), dried over Na$_2$SO$_4$, and concentrated. The residue was purified by silica gel prep-TLC to give the title compound.

Step F. (1S,1aS,6aR)-4-((2-fluoro-5-(2-methyl-6-(3-(methylsulfonyl)azetidin-1-yl)pyridin-3-yl)benzyl)oxy)-1,1a,6,6a-tetrahydrocyclopropa[a]indene-1-carboxylic acid, ethyl ester A 40 mL bottle was charged with 3-bromo-2-methyl-6-(3-(methylsulfonyl)azetidin-1-yl)pyridine (30 mg, 98 μmol), 4-[2-fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester from Example 10, Step D (44 mg, 98 μmol), Na$_2$CO$_3$ (20 mg, 196 μmol), dioxane (2 mL), H$_2$O (0.5 mL), and PdCl$_2$dppfCH$_2$Cl$_2$ (5 mg). The bottle was placed on a 100° C. shaker overnight. After being cooled to ambient temperature, the mixture was diluted with ethyl acetate (30 mL), washed with brine, and concentrated to afford the title compound (crude). MS m/e (M+H$^+$) 551.4.

Step F. (1S,1aS,6aR)-4-((2-fluoro-5-(2-methyl-6-(3-(methylsulfonyl)azetidin-1-yl)pyridin-3-yl)benzyl)oxy)-1,1a,6,6a-tetrahydrocyclopropa[a]indene-1-carboxylic acid A mixture of (1S,1aS,6aR)-4-((2-fluoro-5-(2-methyl-6-(3-(methylsulfonyl)azetidin-1-yl)pyridin-3-yl)benzyl) oxy)-1,1a,6,6a-tetrahydrocyclopropa[a]indene-1-carboxylic acid, ethyl ester (50 mg, 91 μmol) in THF (2 mL) and EtOH (1 mL), was added H$_2$O (1 mL), and LiOH (21 mg, 908 μmol). The reaction mixture was stirred at ambient temperature overnight. The pH was adjusted to 4 by HCl (1N), and the reaction mixture was extracted by ethyl acetate twice. The combined organic layer was washed with brine, dried over Na$_2$SO$_4$, and concentrated. The residue was purified by preparative HPLC to give the title compound. MS m/e (M+H$^+$) 523.4; $^1$H NMR (400 MHz, METHANOL-d$_4$) δ: 7.85 (d, J=8.8 Hz, 1H), 7.44 (d, J=5.2 Hz, 1H), 7.34-7.32 (m, 1H), 7.27-7.21 (m, 2H), 6.82 (s, 1H), 6.81 (d, J=8.8 Hz, 1H), 6.75 (d, J=8.0 Hz, 1H), 5.13 (s, 2H), 4.72-4.68 (m, 2H), 4.62-4.60 (m, 2H), 4.62-4.60 (m, 2H), 4.52 (brs, 1H), 3.20 (d, J=6.4 Hz, 1H), 3.07 (s, 3H), 2.97 (d, J=17.6 Hz, 1H), 2.82 (d, J=6.4 Hz, 1H), 2.39 (s, 4H).

Example 52

(1S,1aS,6aR)-4-((2-fluoro-5-(7-methyl-2-(pyridin-4-yl)benzo[d]thiazol-6-yl)benzyl)oxy)-1,1a,6,6a-tetrahydrocyclopropa[a]indene-1-carboxylic acid

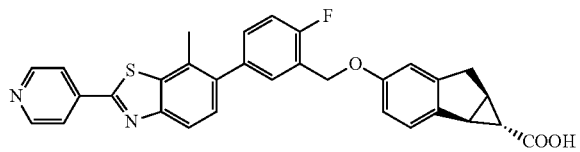 [SMILES: Cc1c(-c2ccc(F)c(COc3ccc4c(c3)C[C@H]3[C@H](C(=O)O)[C@@H]43)c2)ccc2nc(-c3ccncc3)sc12]

Step A. 6-bromo-7-methylbenzo[d]thiazol-2-amine and 6-bromo-5-methylbenzo[d]thiazol-2-amine To a solution of compound 3,4-dimethyl-aniline (7.1 g, 0.059 mol) in AcOH (110 mL), was added $Br_2$ (9.44 g, 0.059 mmol) and potassium thiocyanate (5.7 g, 0.059 mmol) accordingly. The reaction mixture is stirred for 18 hrs at 26° C. The mixture was filtered. The filtrate was concentrated and partitioned by DCM and aq. $Na_2CO_3$. The organic layer was washed with water and brine, dried over $Na_2SO_4$ and concentrated in vacuo to afford a crude mixture of two regioisomers: 6-bromo-7-methylbenzo[d]thiazol-2-amine and 6-bromo-5-methylbenzo[d]thiazol-2-amine which were separated by preparative HPLC to give the title compound.

Step B. 6-bromo-2-chloro-7-methylbenzo[d]thiazole

To a stirred solution of t-BuNO$_2$ (3 g, 0.03 mol) and CuCl$_2$ in ACN (30 mL), was added 6-bromo-7-methylbenzo[d]thiazol-2-amine (3.7 g, 0.015 mmol) in ACN (10 mL) at 0° C. The resulting mixture was stirred for 2 h at 26° C. and for 1 h at 60° C. LC-MS showed the reaction was completed. The mixture was cooled and the precipitates were filtered off. The filtrate was portioned by ethyl acetate and water. The organic layer was washed with water, brine, dried over Na$_2$SO$_4$ and concentrated in vacuo to afford crude product which was purified by column chromatography on silica gel (PE:EA=15:1) to give the title compound.

Step C. 6-bromo-7-methyl-2-(pyridin-4-yl)benzo[d]thiazol

To a stirred solution of 6-bromo-2-chloro-7-methylbenzo[d]thiazole (213 mg, 0.81 mmol) and pyridin-4-yl boronic acid (100 mg, 0.81 mmol) in dioxane (4 mL) was added pd(dppf)Cl$_2$ (20 mg), H$_2$O (2 mL) and Na$_2$CO$_3$(257.6 mg, 2.43 mmol). The resulting mixture was stirred at 100° C. for 16 h. The mixture was adjusted to pH7 by HCl (1N, aq) and extracted with EtOAc (20 mL×3). The combined organic phase was washed with brine, dried over Na$_2$SO$_4$, and concentrated. The residue was purified by silica gel prep-TLC (PE:EtOAc=3:1) to give the title compound. MS m/e (M+H$^+$) 306.2.

Step D. (1S,1aS,6aR)-4-((2-fluoro-5-(7-methyl-2-(pyridin-4-yl)benzo[d]thiazol-6-yl)benzyl)oxy)-1,1a,6,6a-tetrahydrocyclopropa[a]indene-1-carboxylic acid, ethyl ester To a stirred solution of 6-bromo-7-methyl-2-(pyridin-4-yl)benzo[d]thiazole (30 mg, 0.1 mmol) and 4-[2-fluoro-5-(4,4,5,5-tetramethyl-[1,3,2]dioxaborolan-2-yl)-benzyloxy]-1,1a,6,6a-tetrahydro-cyclopropa[a]indene-1-carboxylic acid, ethyl ester (52 mg, 0.12 mmol) in THF (1 mL) was added Pd(dppf)Cl$_2$ (10 mg), H$_2$O (1 mL) and Na$_2$CO$_3$ (30 mg, 0.3 mmol). The resulting mixture was stirred at 100° C. for 16 h. The mixture was adjusted to pH 7 by HCl (1N, aq) and extracted with EtOAc (3×10 mL). The combined organic phase was washed with brine, and dried over Na$_2$SO$_4$, concentrated. The residue was purified by silica gel preparative TLC (PE:EtOAc=3:1) to give the title compound. MS (ESI) m/e (M+H$^+$): 551.6.

Step E. (1S,1aS,6aR)-4-((2-fluoro-5-(7-methyl-2-(pyridin-4-yl)benzo[d]thiazol-6-yl)benzyl)oxy)-1,1a,6,6a-tetrahydrocyclopropa[a]indene-1-carboxylic acid To a stirred solution of (1S,1aS,6aR)-4-((2-fluoro-5-(7-methyl-2-(pyridin-4-yl)benzo[d]thiazol-6-yl)benzyl)oxy)-1,1a,6,6a-tetrahydrocyclopropa[a]indene-1-carboxylic acid, ethyl ester (38 mg, 0.07 mmol) and LiOH (15.6 mg, 0.7 mmol) in MeOH (2 mL), was added THF (2 mL) and H$_2$O (2 mL). The resulting mixture was stirred at room temperature for 3 hours. The mixture was adjusted to pH 6 by HCl (1 N, aq) and extracted with EtOAc (10 mL×3). The combined organic layer was washed with brine, dried over Na$_2$SO$_4$, and concentrated to afford crude product which was purified by preparative HPLC purification to yield the title compound. MS m/e (M+H$^+$): 523.4; $^1$H-NMR (400 MHz, methanol-d$_4$) δ: 8.95 (d, J=4.8 Hz, 1H), 8.47 (d, J=4.8 Hz, 1H), 8.11 (d, J=7.6 Hz, 1H), 7.45-7.52 (m, 2H), 7.37 (d, J=8.0 Hz, 1H), 7.25-7.32 (m, 2H), 6.86 (s, 1H), 6.68 (d, J=8.0 Hz, 1H), 5.18 (s, 2H), 3.32-3.38 (m, 1H), 2.91-2.99 (m, 1H), 2.75 (brs, 1H), 2.48 (s, 3H), 2.31-2.35 (m, 1H), 1.09 (brs, 1H).

Example 53

7-(3-((((1S,1aS,6aR)-1-carboxy-1,1a,6,6a-tetrahydrocyclopropa[a]inden-4-yl)oxy)methyl)-4-fluorophenyl)-1,5-dimethyl-1H-pyrazolo[4,3-b]pyridin-4-ium formate

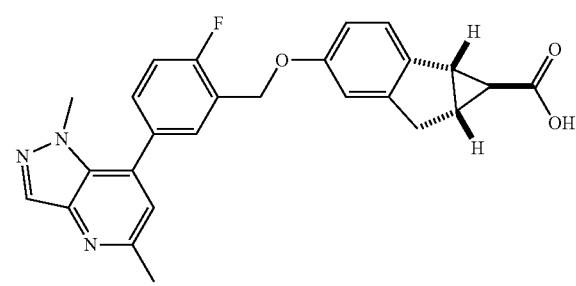

Step A. 7-(3-((((1S,1aS,6aR)-1-carboxy-1,1a,6,6a-tetrahydrocyclopropa[a]inden-4-yl)oxy)methyl)-4-fluorophenyl)-1,5-dimethyl-1H-pyrazolo[4,3-b]pyridine ethyl ester A 2-dram vial (equipped with stir bar) containing 7-chloro-1,5-dimethyl-1H-pyrazolo[4,3-b]pyridine (30 mg, 0.166 mmol) was charged with 4-[2-fluoro-5-(4,4,5,5-tetramethyl-[1,3,2]dioxaborolan-2-yl)-benzyloxy]-1,1a,6,6a- tetrahydro-cyclopropa[a]indene-1-carboxylic acid, ethyl ester from Example 10, Step D (25 mg, 0.055 mmol), and 1,1'-bis(di-tert-butylphosphino)ferrocene palladium dichloride (3.60 mg, 5.53 μmol). In a glove box, degassed THF (600 μL) and degassed 1M aq. potassium phosphate (111 μL, 0.111 mmol) were added into the vial which was capped and stirred overnight at 90° C. To remove the Pd catalyst, the reaction mixture was cooled to room temperature and 1 mL of EtOAc was added to the reaction mixture, followed by addition of SiliaMetS® dimercapto triazine metal scavenger (100 mg, 0.060 mmol, 0.60 mmol/g). The reaction mixture was stirred at r.t. for 4 hours. The mixture was filtered and filtrate was collected. To remove salts: 1 mL of saturated aq. $NaHCO_3$ was added into the above filtrate and extracted with EtOAc (2×2 mL). The combined organic layers were collected into a 2-dram vial and the volatiles were removed with a GENEVAC vacuum pump to afford the title compound (crude).

Step B: 7-(3-((((1S,1aS,6aR)-1-carboxy-1,1a,6,6a-tetrahydrocyclopropa[a]inden-4-yl)oxy)methyl)-4-fluorophenyl)-1,5-dimethyl-1H-pyrazolo[4,3-b]pyridin-4-ium formate The above vial containing 7-(3-((((1S,1aS,6aR)-1-carboxy-1,1a,6,6a-tetrahydrocyclopropa[a]inden-4-yl)oxy)methyl)-4-fluorophenyl)-1,5-dimethyl-1H-pyrazolo[4,3-b]pyridine, ethyl ester was charged with THF (220 μL), MeOH (110 μL) and saturated aqueous lithium hydroxide (220 μL, 0.055 mmol) and heated at 55° C. for 2 h with stirring. The reaction mixture was acidified with addition of 1N aq. HCl (480 μL, 0.055 mmol). Volatiles were removed with a GENEVAC vacuum pump. The residue was dissolved in DMSO (1.4 mL), purified with semi-preparative HPLC, and eluted with 0.1% formic acid in acetonitrile/$H_2O$ to afford the title compound. $^1$H NMR (500 MHz, DMSO-$d_6$) δ 8.18 (s, 1H), 7.74 (d, 1H), 7.60 (m, 1H), 7.42 (t, 1H), 7.28 (m, 1H), 7.14 (s, 1H), 6.88 (s, 1H), 6.78 (m, 1H), 5.14 (s, 1H), 3.16 (m, 1H), 2.94 (m, 1H), 2.76 (m, 1H), 2.59 (s, 3H), 2.48 (s, 3H), 2.28 (m, 1H). MS m/e (M+H$^+$): 444.

Example 54

(1S,1aS,6aR)-4-((2-Fluoro-5-(6-(3-(methylsulfonyl)propoxy)-5-(trifluoromethyl)pyridin-3-yl)benzyl)oxy)-1,1a,6,6a-tetrahydrocyclopropa[a]indene-1-carboxylic acid

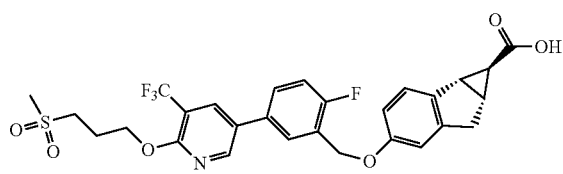 [SMILES: CS(=O)(=O)CCCOc1ncc(-c2ccc(F)c(COc3ccc4c(c3)C[C@H]3[C@H](C(=O)O)[C@@H]43)c2)cc1C(F)(F)F]

Step A. 5-Bromo-2-(3-(methylthio)propoxy)-3-(trifluoromethyl)pyridine

To 3-methylthiopropanol (0.917 g, 8.64 mmol) in dry THF (100 ml) at rt was added NaH (0.346 g, 8.64 mmol). The mixture was stirred at rt for 30 min. 5-bromo-2-chloro-3-(trifluoromethyl)pyridine (1.5 g, 5.76 mmol) was added. The resulting mixture was heated at 60° C. for 4 hours, diluted with $H_2O$, and extracted with EtOAc three times. The combined extracts were washed with brine, dried over $MgSO_4$, filtered, concentrated and purified by flash chromatography on silica gel (0-15% EtOAc/hexanes) to give the title compound. MS m/e (M+H$^+$): 330, 332.

Step B. 5-Bromo-2-(3-(methylsulfonyl)propoxy)-3-(trifluoromethyl)pyridine

To 5-bromo-2-(3-(methylthio)propoxy)-3-(trifluoromethyl)pyridine (1.33 g, 4.03 mmol) in $CH_2Cl_2$ (100 ml) at 0° C. was added mCPBA (1.986 g, 8.86 mmol) in $CH_2Cl_2$ (10 ml). The resulting mixture was stirred at 0° C. for 1 h, quenched with $Na_2S_2O_3$ aq. solution, and extracted with DCM three times. The combined extracts were washed with saturated $Na_2CO_3$, brine, dried over $MgSO_4$, filtered, concentrated and purified by flash chromatography on silica gel (0-60% EtOAc/hexanes) to give the title compound. MS m/e (M+H$^+$): 362, 363.

Step C. (2-Fluoro-5-(6-(3-(methylsulfonyl)propoxy)-5-(trifluoromethyl)pyridin-3-yl)phenyl)methanol The solution of 5-bromo-2-(3-(methylsulfonyl)propoxy)-3-(trifluoromethyl)pyridine (500 mg, 1.381 mmol), [4-fluoro-3-(hydroxymethyl)phenyl]boronic acid (352 mg, 2.071 mmol), PdOAc$_2$ (12.40 mg, 0.055 mmol), potassium carbonate (382 mg, 2.76 mmol) and 2-dicyclohexylphosphino-2',6'-dimethoxybiphenyl (34.0 mg, 0.083 mmol) in THF (4 ml)/Water (0.8 ml) was heated at 70° C. for 2 h. The reaction mixture was diluted with $H_2O$, and extracted with EtOAc three times. The combined extracts were washed with brine, dried over $MgSO_4$, filtered, concentrated and purified by flash chromatography on silica gel (0-60% EtOAc/hexanes) to give the title compound. MS m/e (M+H$^+$): 408.

Step D. (1S,1aS,6aR)-4-((2-fluoro-5-(6-(3-(methylsulfonyl)propoxy)-5-(trifluoromethyl)pyridin-3-yl)benzyl)oxy)-1,1a,6,6a-tetrahydrocyclopropa[a]indene-1-carboxylic acid, ethyl ester To a solution of (2-fluoro-5-(6-(3-(methylsulfonyl)propoxy)-5-(trifluoromethyl)pyridin-3-yl)phenyl)methanol (100 mg, 0.245 mmol) and (1S,1aS,6aR)-ethyl 4-hydroxy-1,1a,6,6a-tetrahydrocyclopropa[a]indene-1-carboxylate (64.3 mg, 0.295 mmol) in toluene (2 ml)/THF (2 ml) at rt was added triphenylphosphine resin (99 mg, 0.295 mmol) followed by DIAD (0.057 ml, 0.295 mmol). The reaction mixture was allowed to warmed up to rt and stirred at rt overnight. The reaction mixture was then concentrated to dryness and purified by flash chromatography on silica gel (0-30% EtOAc/hexanes) to give the title compound. MS m/e (M+H$^+$): 608.

Step E. (1S,1aS,6aR)-4-((2-Fluoro-5-(6-(3-(methylsulfonyl)propoxy)-5-(trifluoromethyl)pyridin-3-yl)benzyl)oxy)-1,1a,6,6a-tetrahydrocyclopropa[a]indene-1-carboxylic acid To (1S,1aS,6aR)-ethyl 4-((2-fluoro-5-(6-(3-(methylsulfonyl)propoxy)-5-(trifluoromethyl)pyridin-3-yl)benzyl)oxy)-1,1a,6,6a-tetrahydrocyclopropa[a]indene-1-carboxylate (70 mg, 0.115 mmol) in MeOH (2 ml)/THF (2 ml)/Water (1.3 ml) at rt was added lithiumhydroxide monohydrate (19.34 mg, 0.461 mmol). The resulting mixture was stirred at rt overnight, diluted with H$_2$O, acidified with 1N HCl to pH 4, and extracted with EtOAc three times. Combined extracts were washed with brine, dried over MgSO$_4$, filtered, concentrated and purified by HPLC (Waters SUNFIRE C18 column, 37-72% MeCN/H$_2$O) to afford the title compound. MS m/e (M+H$^+$): 580; $^+$$^1$H-NMR δ (ppm) (DMSO-d$_6$): 2.19 (2H, m), 2.30 (1H, m), 2.78 (1H, m), 2.96 (1H, m), 3.0 (3H, s), 3.22 (4H, m), 4.55 (2H, t, J=6.45 Hz), 5.10 (2H, s), 6.82 (1H, d, J=8.46 Hz), 6.91 (1H, s), 7.29 (1H, d, J=8.28 Hz), 7.37 (1H, t, J=9.16 Hz), 7.80 (1H, s), 7.94 (1H, d, J=6.76 Hz), 8.32 (1H, s), 8.73 (1H, s).

Example 55

(1S,1aS,6aR)-4-((2-fluoro-5-(6-(((tetrahydro-2H-pyran-4-yl)methyl)amino)-4-(trifluoromethyl)pyridin-3-yl)benzyl)oxy)-1,1a,6,6a-tetrahydrocyclopropa[a]indene-1-carboxylic acid

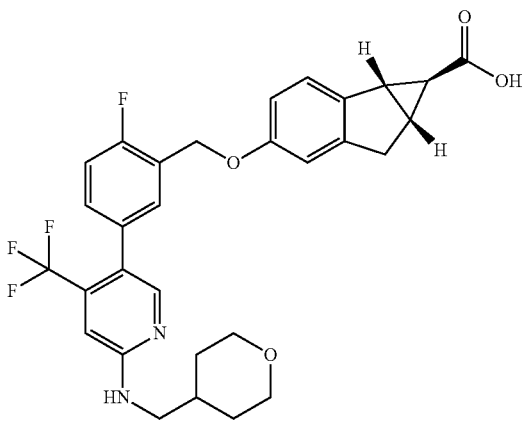 [SMILES: O=C(O)[C@H]1[C@@H]2Cc3cc(OCc4cc(-c5cnc(NCC6CCOCC6)cc5C(F)(F)F)ccc4F)ccc3[C@@H]21]

Step A. 2-(3-(bromomethyl)-4-fluorophenyl)-4,4,5,5-tetramethyl-1,3,2-dioxaborolane A methylene chloride solution of bromine (0.698 M, 3 ml, 2.094 mmol) was added slowly to a solution of (2-fluoro-5-(4,4,5,5-tetramethyl-1,3,2-dioxaborolan-2-yl)phenyl) methanol (250 mg, 0.992 mmol), triethylamine (0.15 ml, 1.076 mmol) and triphenylphosphine (547 mg, 2.086 mmol) in dichloromethane (2 ml) at 0° C. under N$_2$. The mixture was stirred at RT overnight. The solvent was evaporated. The residue was purified on silica gel using hexane and EtOAc to obtain the title compound. $^1$H-NMR (500 MHz, CDCl$_3$) δ: 7.84 (dd, 1H), 7.75 (ddd, 1H), 7.06 (dd, 1H), 4.5 (s, 3H), 1.34 (s, 12H).

Step B. (1S,1aS,6aR)-4-((2-fluoro-5-(4,4,5,5-tetramethyl-1,3,2-dioxaborolan-2-yl)benzyl)oxy)-1,1a,6,6a-tetrahydrocyclopropa[a]indene-1-carboxylic acid, ethyl ester Under a dry nitrogen atmosphere, cesium carbonate (82 mg, 0.252 mmol) was added to a solution of (1S,1aS,6aR)-4-hydroxy-1,1a,6,6a-tetrahydrocyclopropa[a]indene-1-carboxylic acid, ethyl ester from Reference Example 1(55 mg, 0.252 mmol) and 2-(3-(bromomethyl)-4-fluorophenyl)-4,4,5,5-tetramethyl-1,3,2-dioxaborolane (78 mg, 0.248 mmol) in DMF (1 ml) under N$_2$ at RT. After stirring at RT overnight, the reaction mixture was quenched by addition of saturated NH$_4$Cl solution and extracted with EtOAc (3×). The combined organic phase was washed with water (3×) and brine, dried (MgSO$_4$), filtered and the solvent evaporated. The residue was purified by preparative HPLC on silica gel eluted with hexane and EtOAc to give the title compound. MS m/e: (M+Na$^+$) 475 and (M+H)$^+$ 453.

Step C. (1S,1aS,6aR)-4-((5-(6-chloro-4-(trifluoromethyl)pyridin-3-yl)-2-fluorobenzyl)oxy-1,1a,6,6a-tetrahydrocyclopropa[a]indene-1-carboxylic acid, ethyl ester 5-Bromo-2-chloro-4-(trifluoromethyl)pyridine (974 mg, 3.74 mmol) was added to a solution of (1S,1aS,6aR)-4-((2-fluoro-5-(4,4,5,5-tetramethyl-1,3,2-dioxaborolan-2-yl)benzyl)oxy)-1,1a,6,6a-tetrahydrocyclopropa[a]indene-1-carboxylic acid, ethyl ester (1.583 g, 3.5 mmol) in DME (20 ml) under N$_2$, followed by potassium carbonate (2.43 g, 17.58 mmol) and 1,1'-bis(diphenylphosphino)ferrocene-palladium (ii)dichloride dichloromethane complex (35 mg, 0.043 mmol). The mixture was heated at 90° C. overnight. It was poured into saturated NH$_4$Cl solution and extracted with EtOAc (1×). The organic phase was washed with brine, dried (MgSO$_4$), filtered and the solvent evaporated. The residue was purified on silica gel using hexane and to give the title compound. MS m/e: (M+H)$^+$ 506, 508.

Step D. (1S,1aS,6aR)-4-((2-fluoro-5-(6-(((tetrahydro-2H-pyran-4-yl)methyl)amino)-4-(trifluoromethyl)pyridin-3-yl)benzyl)oxy)-1,1a,6,6a-tetrahydrocyclopropa[a]indene-1-carboxylic acid, ethyl ester Hunig's Base (0.12 ml, 0.687 mmol) was added to a solution of 4-aminomethyltetrahydro[2H]pyran (70 mg, 0.608 mmol) and (1S,1aS,6aR)-4-((5-(6-chloro-4-(trifluoromethyl)pyridin-3-yl)-2-fluorobenzyl)oxy)-1,1a,6,6a-tetrahydrocyclopropa[a]indene-1-carboxylic acid, ethyl ester (113 mg, 0.223 mmol) in acetonitrile (0.4 ml) under N$_2$. The solution was heated at 150° C. for 48 hours, diluted with EtOAc, washed with saturated NaHCO$_3$ solution and brine, dried (MgSO$_4$), filtered and the solvent evaporated. The residue was purified on silica gel using hexane for 1 minute and EtOAc to give the title compound. MS m/e: (M+H)$^+$ 585.

Step E. (1S,1aS,6aR)-4-((2-fluoro-5-(6-(((tetrahydro-2H-pyran-4-yl)methyl)amino)-4-(trifluoromethyl)pyridin-3-yl)benzyl)oxy)-1,1a,6,6a-tetrahydrocyclopropa[a]indene-1-carboxylic acid Sodium hydroxide (0.3 ml, 0.300 mmol) was added to a solution of (1S,1aS,6aR)-4-((2-fluoro-5-(6-(((tetrahydro-2H-pyran-4-yl)methyl)amino)-4-(trifluoromethyl)pyridin-3-yl)benzyl)oxy)-1,1a,6,6a-tetrahydrocyclopropa[a]indene-1-carboxylic acid, ethyl ester (91 mg, 0.156 mmol) in methanol (1 ml)/THF (0.5 ml) at RT under N$_2$. The mixture was heated at 60° C. for 3 hours. Most of the solvent was evaporated. The residue was dissolved in 2 ml water, neutralized by addition of hydrochloric acid (0.3 ml, 0.300 mmol), centrifuged and washed with water (2×1 ml) to give the title compound. MS m/e: (M+H)$^+$ 557 and (M−H)$^+$ at 555; $^1$H-NMR (500 MHz, CD$_3$OD) δ: 7.87 (s, 1H), 7.39 (d, 1H), 7.28-7.22 (m, 2H), 7.15 (t, 1H), 6.84 (d, 2H), 6.77 (dd, 1H), 5.11 (s, 2H), 3.95 (dd, 2H), 3.41 (dt, 2H), 3.32-3.20 (m, 4H), 3.0 (d, 1H), 2.84 (d, 1H), 2.41-2.36 (m, 1H), 1.95-1.86 (m, 1H), 1.72 (d, 2H), 1.38-1.27 (m, 3H), 1.04 (t, 1H).

Biological Assays

Generation of GPR40-Expressing Cells:

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine, LIFE TECHNOLOGIES (Carlsbad, Calif.), following manufacturer's instructions. Stable cell-lines were generated following drug selection.

FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 µL medium/well. The cells were incubated with 20 µl/well of the assay buffer (HBSS, 0.1% BSA, 20 mM HEPES, 2.5 mM probenecid, pH 7.4) containing 8 µM fluo-4, AM, 0.08% pluronic acid at room temperature for 100 minutes. Fluorescence output was measured using FLIPR. Compounds were dissolved in DMSO and diluted to desired concentrations with assay buffer. 13.3 µL/well of compound solution was added. The activities of the compounds in the examples have $EC_{50}$ (effective concentration of compound to afford 50% of the maximum observed fluorescence) values listed in Table I.

Inositol Phosphate Turnover Assay:

The assay is performed in a 96-well format. HEK cells stably expressing human GPR40 are plated to be 60-80% confluent within 72 h. After 72 h, the plates are aspirated and the cells washed with inositol-free DMEM (ICN). The wash media is replaced with 150 µL of 3H-inositol labeling media (inositol-free media containing 0.4% human albumin or 0.4% mouse albumin, 1× pen/strep antibiotics, glutamine, 25 mM HEPES to which is added 3H-myo-inositol NEN #NET114A 1 mCi/mL, 25 Ci/mmol diluted 1:150 in loading media with a final specific radioactivity of 1 µCi/150 µL). Alternatively, the human and mouse albumin can be added after the overnight labeling step before the addition of LiCl.

The assay is typically run the next day after 18 h labeling. On the day of the assay, 5 µL of 300 mM LiCl is added to all wells and incubated at 37 degrees for 20 min. 0.75 µL of 200× compounds are added and incubated with the cells for 60 min at 37 degrees. The media is then aspirated off and the assay terminated with the addition of 60 µL 10 mM formic acid. The cells are lysed for 60 min at room temperature. 15-30 µL of lysate is mixed with 70 µL/1 mg YSi SPA beads AMERSHAM (United Kingdom) in clear bottom Isoplates. The plates are shaken for 2 h at room temperature. Beads are allowed to settle and the plates are counted in the Wallac MICROBETA instrument. The activities of the compounds in the examples have $EC_{50}$ (effective concentration of compound to afford 50% of the maximum observed fluorescence) values listed in Table I.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

TABLE 1

Potency of Examples 1-55 in Human GPR40 FLIPR and IP1 Assays

| Ex. No. | Human GPR40, FLIPR, EC50, nM | Human GPR40 IP1, EC50, nM |
|---|---|---|
| 1 | 46.0 | 7.3 |
| 2 | 70.2 | 18.5 |
| 3 | 59.9 | nd |
| 4 | 89.1 | 15.0 |
| 5 | 58.5 | 30.8 |
| 6 | 57.4 | 22.3 |
| 7 | 98.0 | nd |
| 8 | 232.3 | nd |
| 9 | 99.0 | nd |
| 10 | 93.1 | nd |
| 11 | 55.9 | 43.5 |
| 12 | 122.7 | nd |
| 13 | 102.1 | nd |
| 14 | 144.8 | 83.5 |
| 15 | 316.6 | nd |
| 16 | 4283 | nd |
| 17 | 252.1 | nd |
| 18 | 206 | nd |
| 19 | 5.5 | nd |
| 20 | 178.6 | 51.5 |
| 21 | 47.4 | nd |
| 22 | 58.9 | nd |
| 23 | 74.2 | 84.5 |
| 24 | 73.3 | 304 |
| 25 | 67.9 | 39.0 |
| 26 | 83.8 | 25.5 |
| 27 | 48.9 | 10.0 |
| 28 | 18.5 | 8.0 |
| 29 | 16.1 | 26.5 |
| 30 | 49.2 | 30.0 |
| 31 | 30.9 | 14.0 |
| 32 | 20.6 | 5.0 |
| 33 | 30.7 | 6.5 |
| 34 | 75.1 | 889 |
| 35 | 77.8 | 1392 |
| 36 | 19.9 | 20.5 |
| 37 | 16.6 | 14.7 |
| 38 | 74.1 | 80.8 |
| 39 | 47.6 | 26.0 |
| 40 | 32.0 | 519.0 |
| 41 | 22.4 | 6.0 |
| 42 | 12.8 | 51.0 |
| 43 | 75.5 | 13.0 |
| 44 | 23.2 | 221.5 |
| 45 | 29.4 | 853.5 |
| 46 | 38.7 | 629 |
| 47 | 17.8 | 16 |
| 48 | 76.7 | 38.5 |
| 49 | 28.9 | 19.5 |
| 50 | 58.0 | 27.0 |
| 51 | 23.3 | 26.3 |
| 52 | 35.4 | 30.0 |
| 53 | 51.8 | 39.0 |
| 54 | 50.7 | 236 |
| 55 | 35.4 | 5.5 | nd = not determined

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

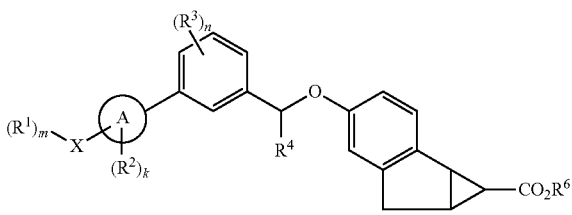

I or a pharmaceutically acceptable salt thereof, wherein ring A is a monocyclic heteroaryl containing 1 to 2 N heteroatoms;

X is
(1) bond,
(2) —O—,
(3) NH,
(4) —($C_{1-6}$)alkyl-O—, wherein the alkyl or oxygen attaches to ring A,
(5) —O—($C_{1-6}$)alkyl-O—, or
(6) —($C_{1-6}$)alkyl-N(H)—, wherein the alkyl or nitrogen attaches to ring A;

$R^1$ is
(1) ($C_{3-7}$)cycloalkyl,
(2) heterocycloalkyl containing 1 to 2 heteroatoms independently selected from the group consisting N, S, and O,
(3) heteroaryl containing 1 to 3 heteroatoms independently selected from the group consisting of N, O, and S,
(4) —S(O)$_2$($C_{1-3}$)alkyl, or
(6) —(CH$_2$)$_q$-aryl,
wherein each heterocycloalkyl, heteroaryl, aryl, or cycloalkyl groups are unsubstituted or substituted with 1 to 2 substitutents each independently $R^5$;

$R^2$ is
(1) ($C_{1-6}$)alkyl,
(2) halo($C_{1-6}$)alkyl,
(3) hydroxy($C_{1-6}$)alkyl, or
(4) halo;

$R^3$ is
(1) ($C_{1-6}$)alkyl, or
(2) halo;

$R^4$ is
(1) hydrogen, or
(2) ($C_{1-3}$)alkyl;

$R^5$ is
(1) oxo,
(2) hydroxy,
(3) ($C_{1-6}$)alkyl,
(4) halo($C_{1-6}$)alkyl,
(5) hydroxy($C_{1-6}$)alkyl,
(6) cyano,
(7) phenyl,
(8) —S(O)$_2$($C_{1-3}$)alkyl,
(9) —($C_{1-3}$)alkyl-S(O)$_2$($C_{1-3}$)alkyl, or
(10) —($C_{1-3}$)alkyl-N(H)—S(O)$_2$($C_{1-3}$)alkyl;

$R^6$ is
(1) hydrogen,
(2) ($C_{1-6}$)alkyl, or
(3) ($C_{3-7}$)cycloalkyl;

n is 0, 1, 2, or 3;
m is 0 or 1;
k is 0, 1, 2 or 3; and
q is 0,1,2, or 3.

2. The compound according to claim 1, or a pharmaceutically acceptable salt thereof, wherein X is a bond, —O—, —N(H)—, —(CH$_2$)$_3$—NH—, —(CH$_2$)$_2$—NH—, —CH$_2$—N(H)—, —(CH$_2$)$_4$—O—, —(CH$_2$)$_3$—O—, —(CH$_2$)$_2$—O—, —CH$_2$—O— or —O—(CH$_2$)$_3$—O—.

3. The compound of claim 2, or a pharmaceutically acceptable salt thereof, wherein ring A is pyridinyl or pyrimidinyl.

4. The compound of claim 1, or a pharmaceutically acceptable salt thereof, wherein $R^6$ is hydrogen.

5. A compound of structural formula I:

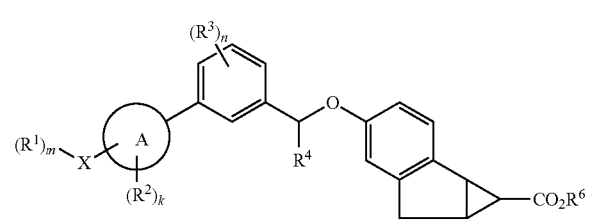

I or a pharmaceutically acceptable salt thereof, wherein ring A is a bicyclic heteroaryl containing 1 to 4 heteroatoms independently selected from the group consisting of N, O, and S;

X is
(1) bond,
(2) —O—,
(3) NH,
(4) —($C_{1-6}$)alkyl-O—, wherein the alkyl or oxygen attaches to ring A,
(5) —O—($C_{1-6}$)alkyl-O—, or
(6) —($C_{1-6}$)alkyl-N(H)—, wherein the alkyl or nitrogen attaches to ring A;

R¹ is
- (1) $(C_{3-7})$cycloalkyl,
- (2) heterocycloalkyl containing 1 to 2 heteroatoms independently selected from the group consisting N, S, and O,
- (3) heteroaryl containing 1 to 3 heteroatoms independently selected from the group consisting of N, O, and S,
- (4) —S(O)$_2$(C$_{1-3}$)alkyl, or
- (6) —(CH$_2$)$_q$-aryl, wherein each heterocycloalkyl, heteroaryl, aryl, or cycloalkyl groups are unsubstituted or substituted with 1 to 2 substitutents each independently R⁵;

R² is
- (1) (C$_{1-6}$)alkyl,
- (2) hydroxy(C$_{1-6}$)alkyl, or
- (3) halo;

R³ is
- (1) (C$_{1-6}$)alkyl, or
- (2) halo;

R⁴ is
- (1) hydrogen, or
- (2) (C$_{1-3}$)alkyl;

R⁵ is
- (7) oxo,
- (8) hydroxy,
- (9) (C$_{1-6}$)alkyl,
- (10) halo(C$_{1-6}$)alkyl,
- (11) hydroxy(C$_{1-6}$)alkyl,
- (12) cyano,
- (7) phenyl,
- (8) —S(O)$_2$(C$_{1-3}$)alkyl,
- (9) —(C$_{1-3}$)alkyl-S(O)$_2$(C$_{1-3}$)alkyl, or
- (10) —(C$_{1-3}$)alkyl-N(H)—S(O)$_2$(C$_{1-3}$)alkyl;

R⁶ is
- (1) hydrogen,
- (2) (C$_{1-6}$)alkyl, or
- (3) (C$_{3-7}$)cycloalkyl;

n is 0, 1, 2, or 3;
m is 0 or 1;
k is 0, 1, 2 or 3; and
q is 0, 1, 2, or 3.

6. The compound according to claim 5, or a pharmaceutically acceptable salt thereof, wherein X is a bond, —O—, —N(H)—, —(CH$_2$)$_3$—NH—, —(CH$_2$)$_2$—NH—, —CH$_2$—N(H)—, —(CH$_2$)$_4$—O—, —(CH$_2$)$_3$—O—, —(CH$_2$)$_2$—O—, —CH$_2$—O— or —O—(CH$_2$)$_3$—O—.

7. The compound of claim 6, or a pharmaceutically acceptable salt thereof, wherein ring A is 1H-pyrazolo[4,3-b]pyridinyl, thiazolo[4,5-b]pyridinyl, or 1H-pyrrolo[2,3-b]pyridinyl.

8. The compound of claim 5, or a pharmaceutically acceptable salt thereof, wherein R⁶ is hydrogen.

9. A compound of structural formula I-A:

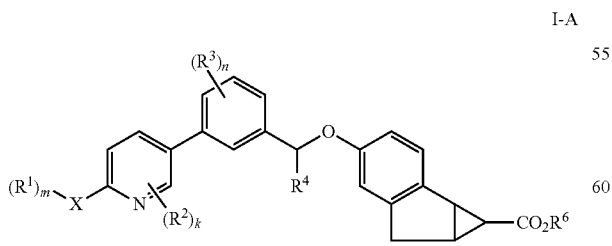

I-A or a pharmaceutically acceptable salt thereof, wherein
X is
- (1) a bond,
- (2) —O—,
- (3) —(C$_{1-6}$)alkyl-O—, wherein the alkyl or oxygen attaches to ring A
- (4) —O—(C$_{1-6}$)alkyl-O—, or
- (5) —(C$_{1-6}$)alkyl-N(H)—, wherein the alkyl or nitrogen attaches to ring A;

R¹ is
- (1) (C$_{3-7}$)cycloalkyl,
- (2) heterocycloalkyl containing 1 to 2 heteroatoms independently selected from the group consisting of N, S, and O,
- (3) heteroaryl containing 1 to 3 heteroatoms independently selected from the group consisting of N, O, and S,
- (4) —S(O)$_2$(C$_{1-3}$)alkyl, or
- (5) —(CH$_2$)q-aryl, wherein each heterocycloalkyl, heteroaryl, aryl, or cycloalkyl groups are unsubstituted or substituted with 1 to 2 substitutents each independently R⁵;

R² is
- (1) (C$_{1-6}$)alkyl,
- (2) halo(C$_{1-6}$)alkyl, or
- (3) hydroxy(C$_{1-6}$)alkyl;

R³ is
- (1) (C$_{1-6}$)alkyl, or
- (2) halo;

R⁴ is
- (1) hydrogen, or
- (2) (C$_{1-3}$)alkyl;

R⁵ is
- (1) oxo,
- (2) hydroxy,
- (3) (C$_{1-6}$)alkyl,
- (4) halo(C$_{1-6}$)alkyl,
- (5) hydroxy(C$_{1-6}$)alkyl,
- (6) cyano,
- (7) phenyl,
- (8) —S(O)$_2$(C$_{1-3}$)alkyl,
- (9) —(C$_{1-3}$)alkyl-S(O)$_2$(C$_{1-3}$)alkyl, or
- (10) —(C$_{1-3}$)alkyl-N(H)—S(O)$_2$(C$_{1-3}$)alkyl;

n is 0, 1, 2, or 3;
m is 0 or 1;
k is 0, 1, 2 or 3, and
q is 0, 1, 2, or 3.

10. A compound selected from
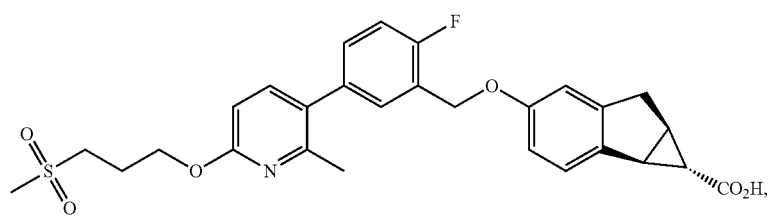
1
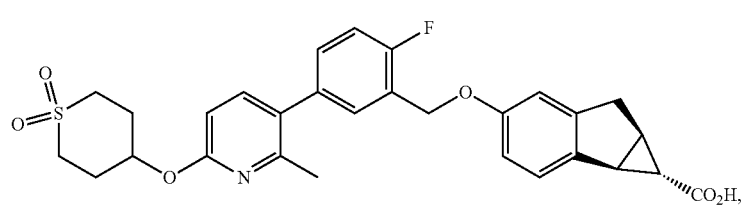
2
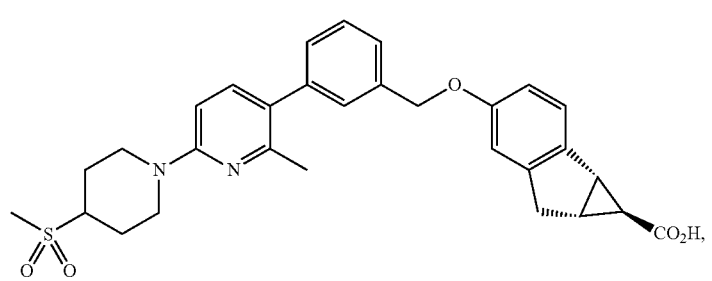
3
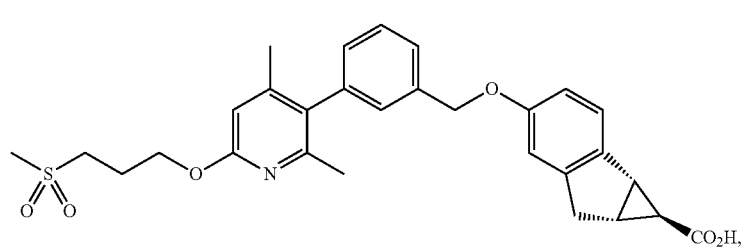
4
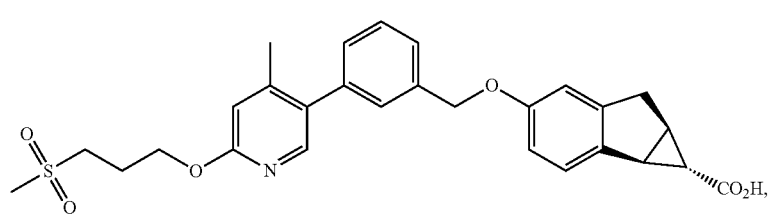
5
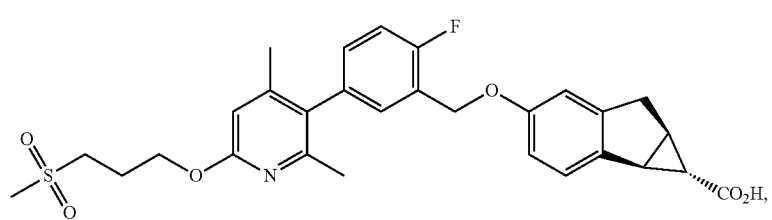
6
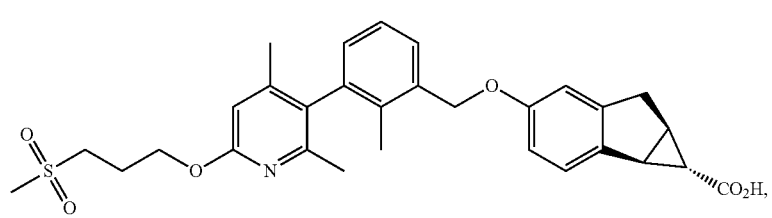
7

8
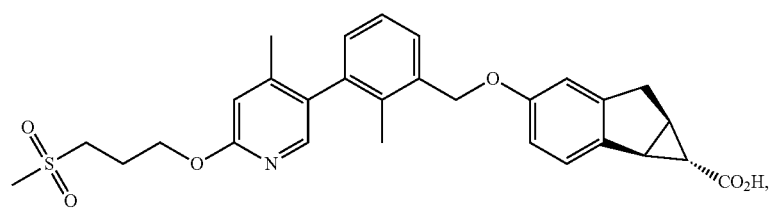
9
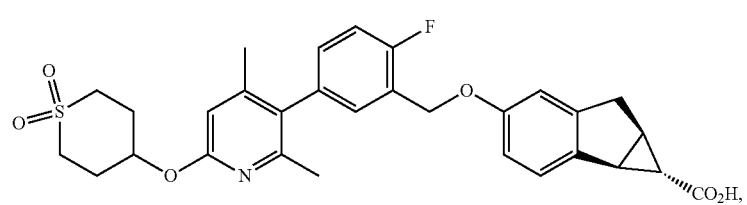
10
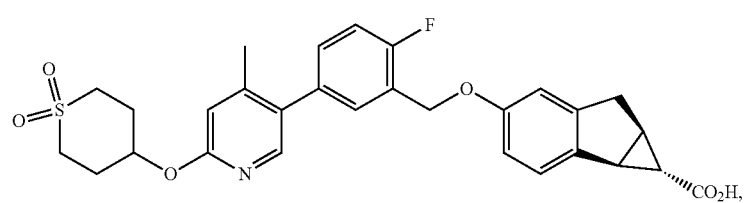
11
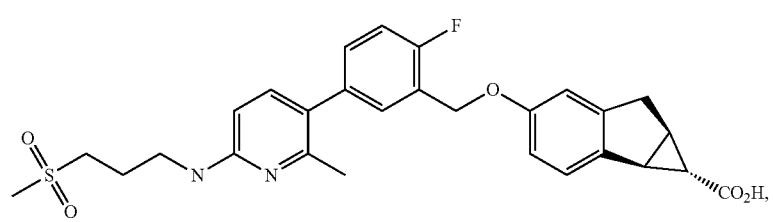
12
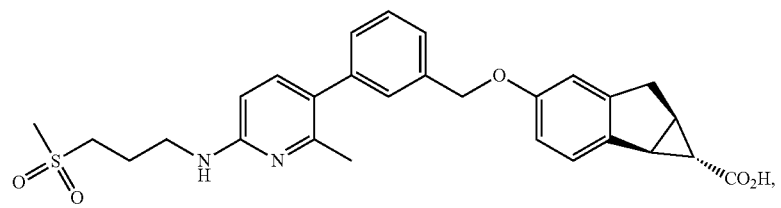
13
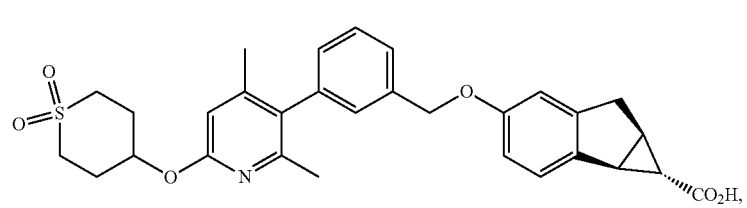
14
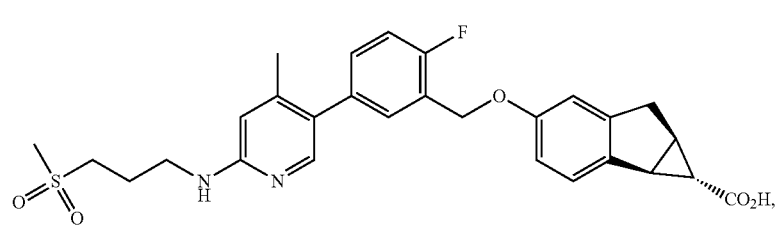

15
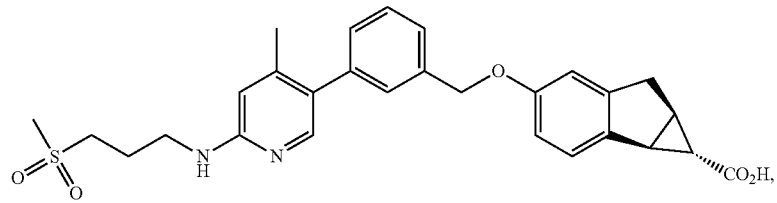
16
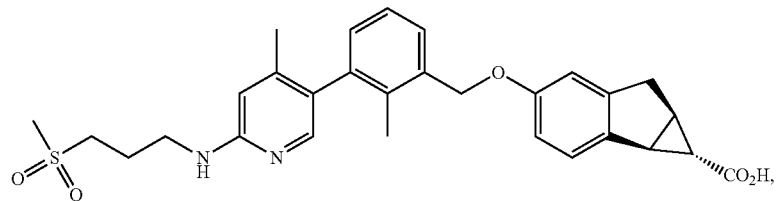
17
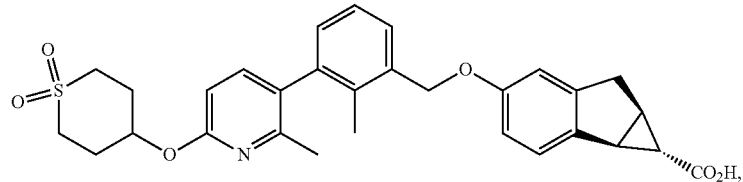
18
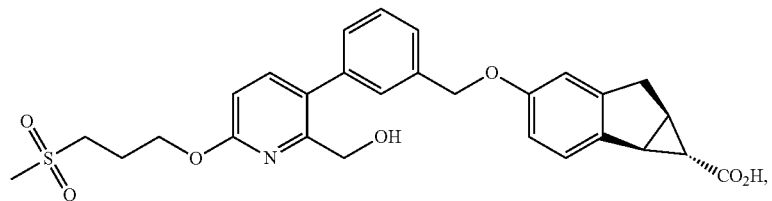
19
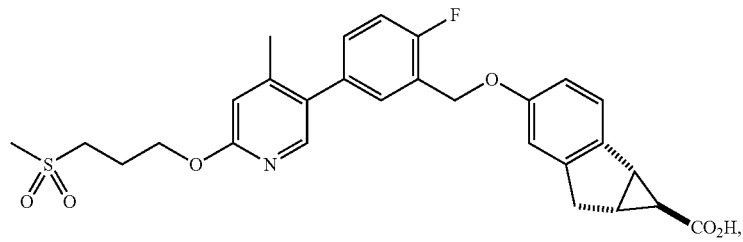
20
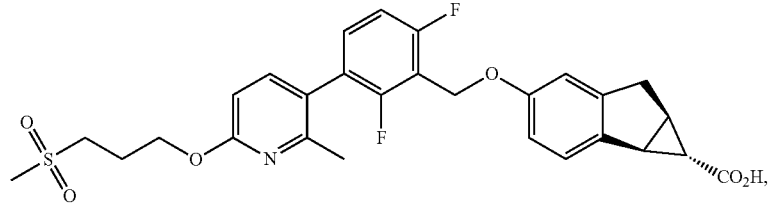
21
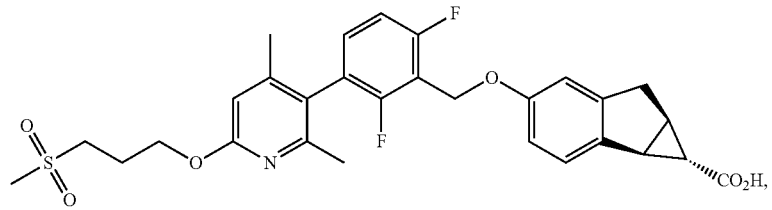

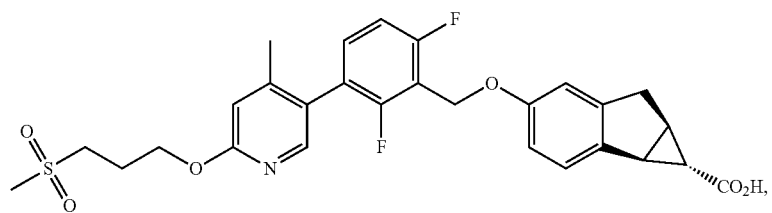
22
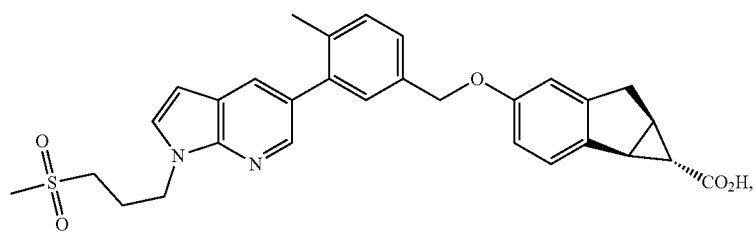
23
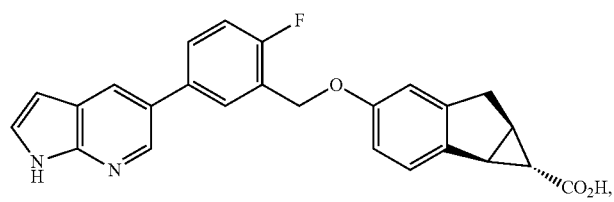
24
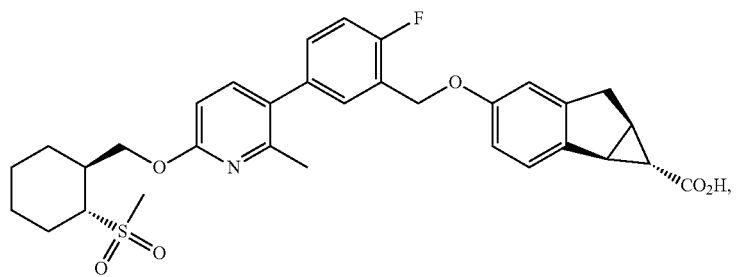
25
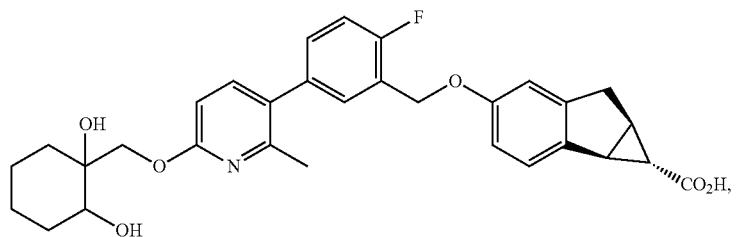
26
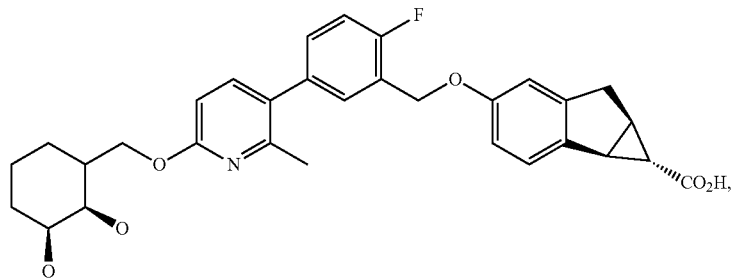
27

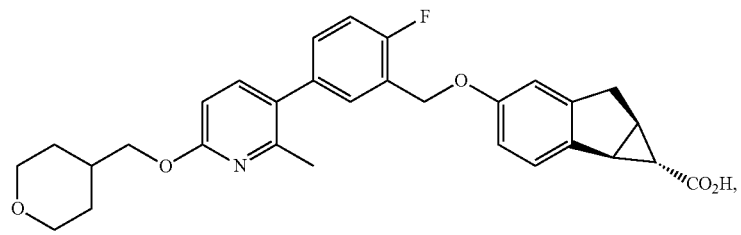
28
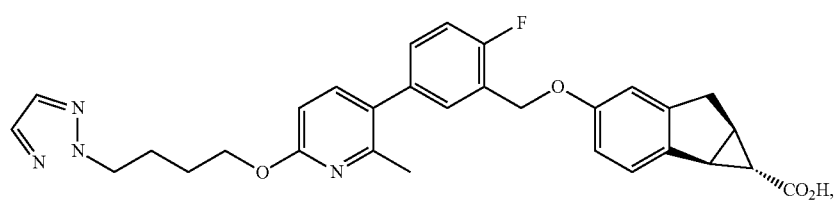
29
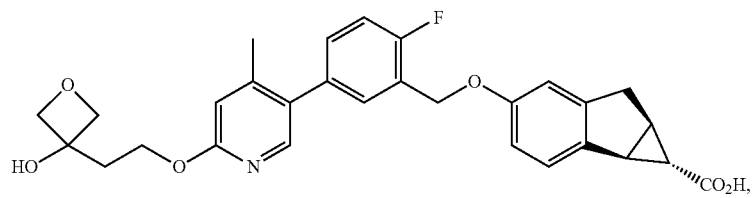
30
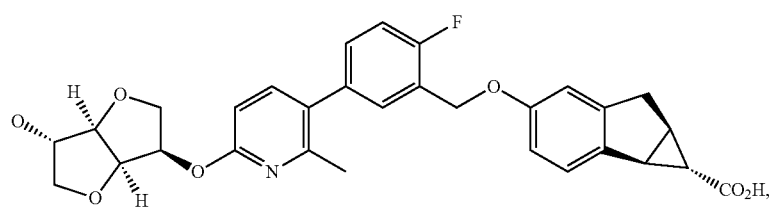
31
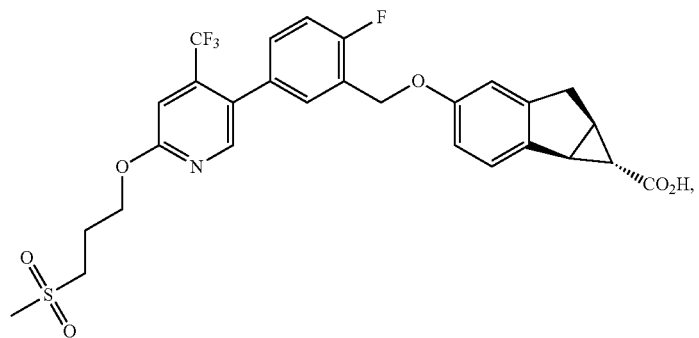
32
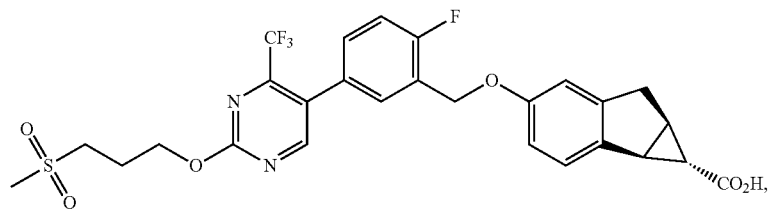
33

34
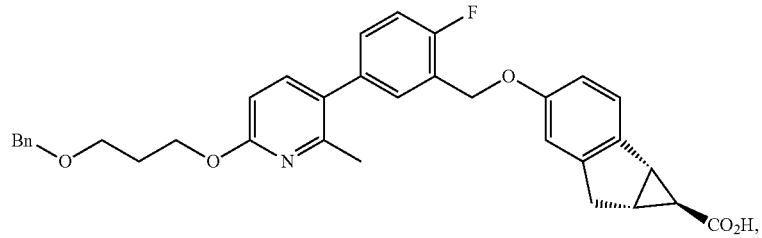
35
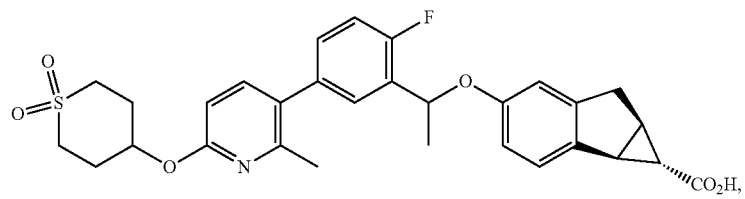
36
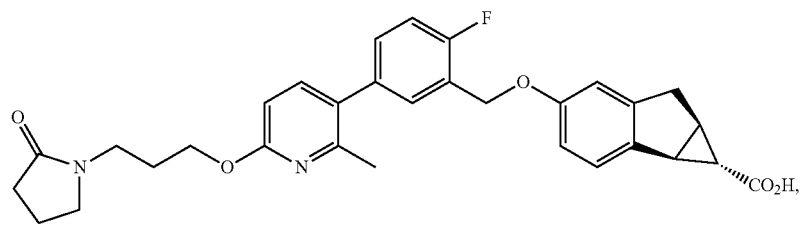
37
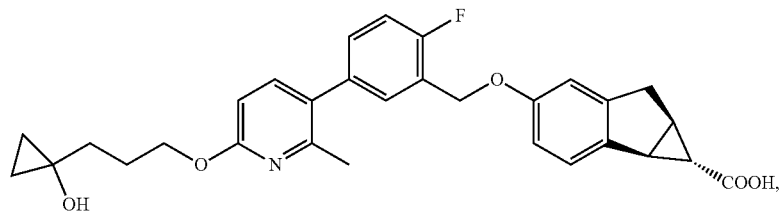
38
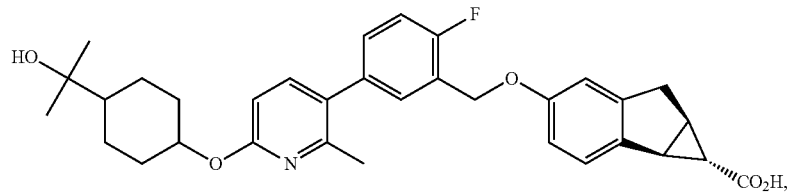
39
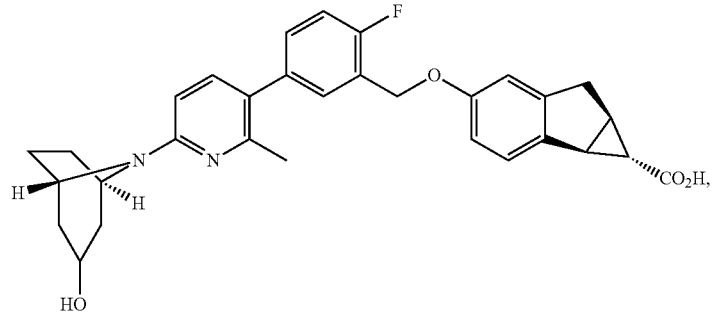

-continued
| | |
|---|---|
| 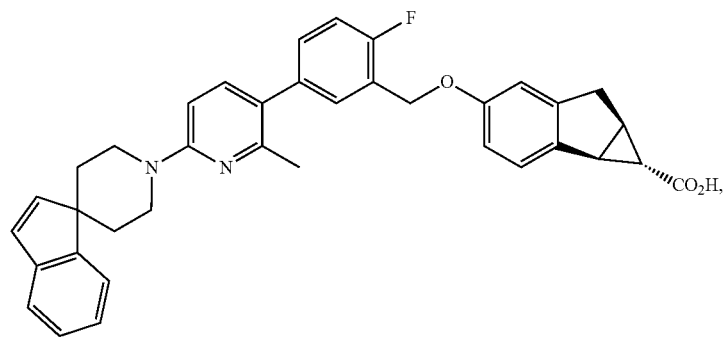 | 40 |
| 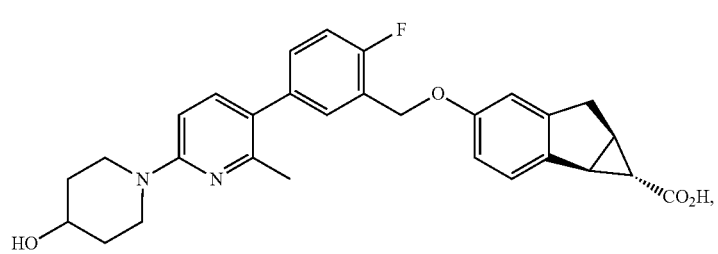 | 41 |
| 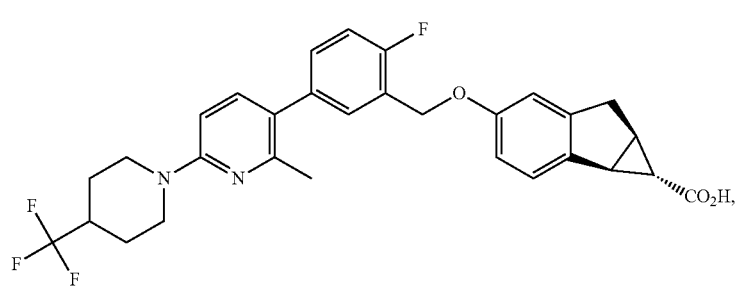 | 42 |
| 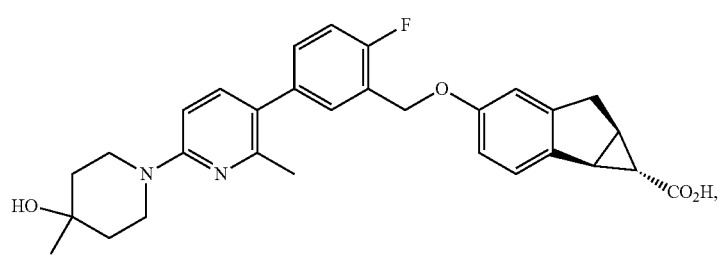 | 43 |
| 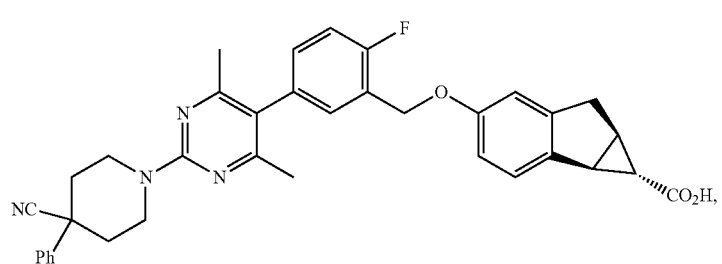 | 44 |
| 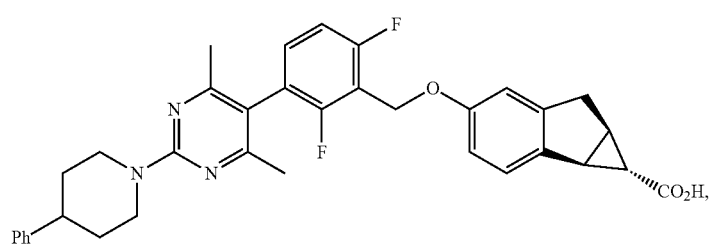 | 45 |

46
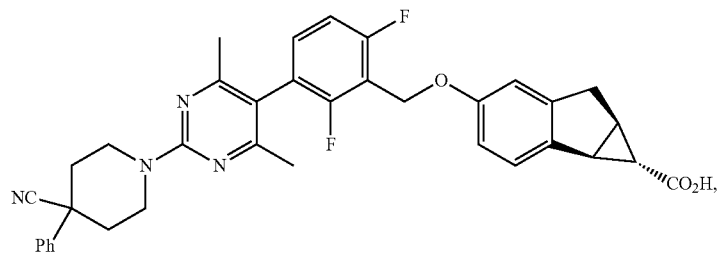
47
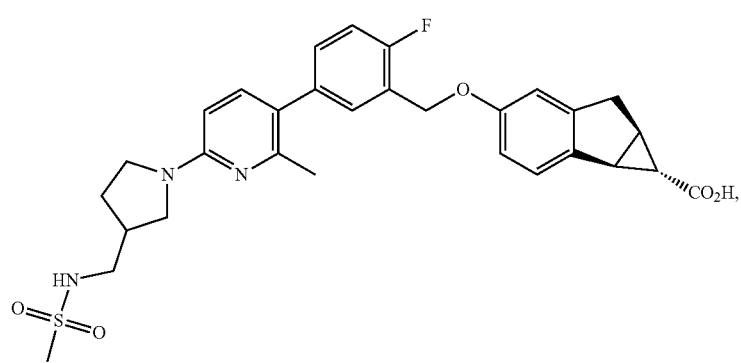
48
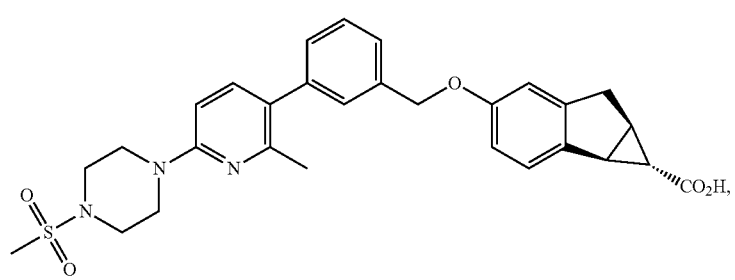
49
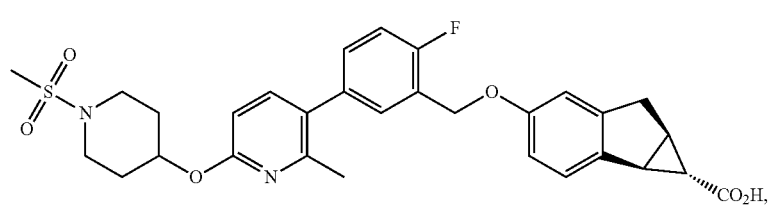
50
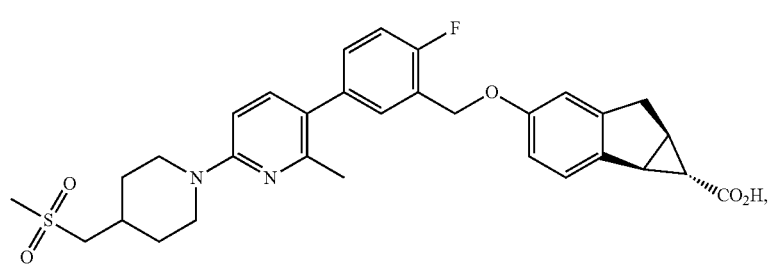
51
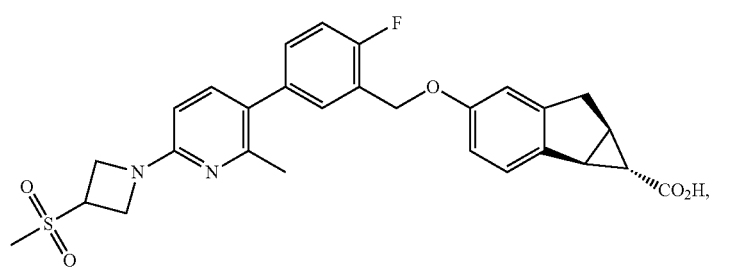

or a pharmaceutically acceptable salt, thereof.

11. A pharmaceutical composition comprising a compound of claim 1, or a pharmaceutically acceptable salt thereof, and a pharmaceutically acceptable carrier.

12. A method of treating type 2 diabetes mellitus in a patient in need of treatment comprising the administration to the patient of a therapeutically effective amount of a compound of claim 1, or a pharmaceutically acceptable salt thereof.

13. A pharmaceutical composition comprising
 (1) a compound of claim 1 or a pharmaceutically acceptable salt thereof;
 (2) one or more compounds selected from the group consisting of:
  (a) PPAR gamma agonists and partial agonists;
  (b) biguanides;
  (c) protein tyrosine phosphatase-1B (PTP-1B) inhibitors;
  (d) dipeptidyl peptidase IV (DP-IV) inhibitors;
  (e) insulin or an insulin mimetic;
  (f) sulfonylureas;
  (g) α-glucosidase inhibitors;
  (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA:cholesterol acyltransferase (ACAT) inhibitors, (vii) CETP inhibitors, and (viii) phenolic anti-oxidants;
  (i) PPARα/γ dual agonists,
  (j) PPARδ agonists,
  (k) antiobesity compounds,
  (l) ileal bile acid transporter inhibitors;
  (m) anti-inflammatory agents;
  (n) glucagon receptor antagonists;
  (o) GLP-1;
  (p) GIP-1;

(q) GLP-1 analogs;
(r) HSD-1 inhibitors;
(s) SGLT 1 inhibitors; and
(t) SGLT 2 inhibitors; and
(3) a pharmaceutically acceptable carrier.

* * * * *